United States Patent
Jang et al.

(10) Patent No.: US 9,598,362 B2
(45) Date of Patent: Mar. 21, 2017

(54) BENZIDINE DERIVATIVE, METHOD FOR PREPARING SAME, AND PHARMACEUTICAL COMPOSITION CONTAINING BENZIDINE DERIVATIVE FOR TREATING LIVER DISEASE CAUSED BY HEPATITIS C VIRUS

(71) Applicants: SEOUL NATIONAL UNIVERSITY R&DB FOUNDATION, Seoul (KR); POSTECH ACADEMY-INDUSTRY FOUNDATION, Pohang-si (KR)

(72) Inventors: Sung Key Jang, Pohang-si (KR); Byeong Moon Kim, Seoul (KR); Il Hak Bae, Daegu (KR); Jin Kyu Choi, Pohang-si (KR); Sun Ju Keum, Seongnam-si (KR); Seung Gi Lee, Changwon-si (KR); Hee Sun Kim, Naju-si (KR)

(73) Assignees: Seoul National University R&DB Foundation, Seoul (KR); POSTECH ACADEMY-INDUSTRY FOUNDATION, Gyeongsangbuk-do (KR)

( * ) Notice: Subject to any disclaimer, the term of this patent is extended or adjusted under 35 U.S.C. 154(b) by 8 days.

(21) Appl. No.: 14/884,356

(22) Filed: Oct. 15, 2015

(65) Prior Publication Data

US 2016/0031810 A1  Feb. 4, 2016

Related U.S. Application Data

(63) Continuation of application No. PCT/KR2014/003660, filed on Apr. 25, 2014.

(30) Foreign Application Priority Data

Apr. 26, 2013 (KR) .................. 10-2013-0046749
Dec. 3, 2013 (KR) .................. 10-2013-0148979

(51) Int. Cl.
| C07D 207/16 | (2006.01) |
| C07D 207/24 | (2006.01) |
| C07D 277/06 | (2006.01) |
| C07D 211/60 | (2006.01) |
| C07K 5/062 | (2006.01) |
| C07K 5/065 | (2006.01) |
| C07D 405/14 | (2006.01) |

(52) U.S. Cl.
CPC ............ *C07D 207/16* (2013.01); *A23L 33/10* (2016.08); *C07D 207/24* (2013.01); *C07D 211/60* (2013.01); *C07D 277/06* (2013.01); *C07D 405/14* (2013.01); *C07K 5/06026* (2013.01); *C07K 5/06034* (2013.01); *C07K 5/06078* (2013.01); *A23V 2002/00* (2013.01)

(58) Field of Classification Search
None
See application file for complete search history.

(56) References Cited

U.S. PATENT DOCUMENTS 8,329,159 B2  12/2012 Belema et al.

FOREIGN PATENT DOCUMENTS

| WO | WO 2006/093867 A1 | 9/2006 | |
| WO | WO 2006/133326 A1 | 12/2006 | |
| WO | WO 2006133326 A1 * | 12/2006 | ........... C07D 207/16 |
| WO | WO 2008/144380 A1 | 11/2008 | |

OTHER PUBLICATIONS

Qiu et al. "Proline derivative . . . " CA154:385618 (2011).*
Davis et al. "Treatment of Chronic Hepatitis C with Recombinant Interferon Alfa" *New England J. Med.* 321(22)1501-1506 (1989).
Harvey J. Alter "Chronic Consequences of Non-A, Non-B Hepatitis" *Current Perspectives in Hepatology, Plenum Publishing, NY* 1st edition 83-97 (1989).
Kronenberger et al. "Novel Hepatitis C Drugs in Current Trials" *Clinics in Liver Disease* 12(3)529-555 (2008).
Davis et al. "Treatment of Chronic Hepatitis C with Recombinant Interferon Alfa" *New England J. Med.* 321(22)1501-1506 (1989) *abstract.
Harvey J. Alter "Chronic Consequences of Non-A, Non-B Hepatitis" *Current Perspectives in Hepatology, Plenum Publishing, NY* 1st edition 83-98 (1989) *p. 83.
Kim et al. "Hepatocellular carcinoma metastasizing to the skull base involving multiple cranial nerves" *World J. of Gastroenterology* 12(41)6727-6729 (2006).
Manns et al. "The way forward in HCV treatment-find the right path" *Nature Reviews* 6:991-1000 (2007).
Kronenberger et al. "Novel Hepatitis C Drugs in Current Trials" *Clinics in Liver Disease* 12(3)529-555 (2008) *abstract.

* cited by examiner

*Primary Examiner* — Heidi Reese
(74) *Attorney, Agent, or Firm* — Klarquist Sparkman, LLP

(57) ABSTRACT

The disclosed compounds have antiviral activity against C-type virus, an optical isomer thereof, a pharmaceutically acceptable salt thereof, a method for preparing the same, and a pharmaceutical composition containing the same as an active ingredient for preventing or treating liver disease caused by hepatitis C virus. The benzidine derivative according to the present invention has excellent antiviral activity against hepatitis C virus and exhibits excellent medicinal activity in the living body, and thus the pharmaceutical composition containing the same as an active ingredient can be useful as a pharmaceutical composition for preventing or treating liver disease, such as acute hepatitis C, chronic hepatitis C, cirrhosis, or hepatocellular carcinoma, caused by C-type virus.

10 Claims, 2 Drawing Sheets

BENZIDINE DERIVATIVE, METHOD FOR PREPARING SAME, AND PHARMACEUTICAL COMPOSITION CONTAINING BENZIDINE DERIVATIVE FOR TREATING LIVER DISEASE CAUSED BY HEPATITIS C VIRUS

CROSS-REFERENCE TO RELATED APPLICATIONS

This patent application is a continuation of PCT/KR2014/003660, filed Apr. 25, 2014, which claims the benefit of both Korean Patent Application No. 10-2013-0046749, filed on Apr. 26, 2013, and Korean Patent Application No. 10-2013-0148979, filed on Dec. 3, 2013. The contents of all three of these patent applications is incorporated herein by reference.

BACKGROUND OF THE INVENTION

1. Field of the Invention

The present invention relates to a compound having the antiviral activity against C-type virus, an optical isomer thereof, a pharmaceutically acceptable salt thereof, a method for preparing the same, and a pharmaceutical composition containing the same as an active ingredient for preventing or treating liver disease caused by hepatitis C virus.

2. Description of the Related Art

Hepatitis C virus (HCV) is a RNA virus belonging to hepacivirus genus of Flaviviridae. This virus was first found in 1989 in USA.

Hepatitis C virus infection is developed by blood transfusion or is community-acquired. In particular, approximately 70% of its infection is caused by kidney dialysis according to the previous report. Once infected with hepatitis C virus, about 20% of the infected people develop acute hepatitis accompanied by liver cirrhosis within 5 years, which would be developed to liver cancer (Davis et al, New. Engl. J. Med., 321 (1989) 1501/Alter et al, Leonard et al., Current Perspective in Hepatology, (1989) p. 83). The high chronic infection rate is rare among RNA virus infections, and therefore such high rate indicates the hepatitis C virus is one of key mediators causing liver cancer. Recently, hepatitis C can be tested with almost every blood sample, so that the infection by blood transfusion has been significantly reduced. However, community-acquired hepatitis C infection has not been efficiently controlled, so its infection rate is very high, making it a world-wide issue.

In the meantime, unlike HBV, HCV is world-widely distributed and 1.5~2% of the total world population are infected, according to the recent report. Once infected with HCV, it is most likely developed into chronic hepatitis. In particular, the chance of progressing to liver cirrhosis and liver cancer is significantly higher than HBV infection. HCV is a taxonomically different virus from HBV, and it belongs to a different virus family, so HCV cannot be prevented with HBV vaccine. Recently, interferon and ribavirin (anti-viral agent) are co-administered to treat HCV infection (Hayashi N., et al., J. Gastroenterol., 41, (2006), 17). However, response to these drugs are different according to the genotype and their medicinal effects are not so great. In addition, the side effects carried by the co-administration of both drugs are severe and the price of them is also very high. Therefore, it is requested to develop a novel and more efficient anti-HCV agent.

The anti-HCV agents, that have been developed to overcome the above disadvantages, display their pharmaceutical activities as the anti-HCV agents by blocking a specific stage of the life cycle of HCV.

The life cycle of HCV is as follows. Once HCV is adhered on the surface of the host cell, HCV invades in the host cell by endocytosis. HCV, invaded in the host cell, produces the precursor protein composed of approximately 3000 amino acid residues from its genomic RNA. Then, HCV reacts to NS3 encoded by the virus genome or signal peptidase of the host cell and NS4 protease to produce about 10 kinds of viral proteins such as capsid protein, envelope protein, NS3/NS4 protease, and NS 5B RNA polymerase, etc. The genomic RNA duplicated by NS 2B polymerase binds to capsid protein and envelope protein mediated by a-glucosidase to produce virus particles. The assembled HCV particles are released from the host cell (Manns M P., et al., Nat. Rev. Drug. Discov., 6, (2007), 991).

The anti-HCV agent is to inhibit the activity of HCV by blocking a certain stage of HCV life cycle, so that the agent is classified based on the life cycle of HCV, as RNA polymerase inhibitor type, protease inhibitor type, a-glucosidase inhibitor type, and other types. For example, the agents based on the activity to inhibit RNA polymerase such as MK-7009 (Merck) and R7128 (Pharmasset/Roche) are now in a phase I clinical trial, and such drugs as VCH-759 (Virochem), R1626 (Roche), and valopicitabine (Idenix) are in a phase II clinical trial. Among the protease inhibitors, ITMN-191 (R-7227, InterMune/Roche) is in a phase I clinical trial, TMC435350 (Medivir/Tibotec) is in a phase II clinical trial, and Boceprevir (SCH 503034, Schering) and Telaprevir (Vertex) are in a phase III clinical trial. In addition, the cyclophilin inhibitor DEBIO-025 (DEBIO) and the glucosidase I inhibitor celgosivir (MIGEBIX) are in a phase II clinical trial (Kronenberger B., et al., Clin Liver Dis., 12, (2008), 529).

However, the resistant virus that showed the resistance against the anti-HCV agents in clinical trial has already been reported. Thus, it is urgently requested to develop a novel anti-HCV agent having the activity to inhibit HCV with totally different mechanism from the conventional anti-HCV mechanism.

Thus, the present inventors studied on an anti-HCV agent that has less cytotoxicity but has excellent anti-viral activity against HCV. As a result, the inventors confirmed that the benzidine derivative had excellent anti-viral activity against HCV but hardly had cytotoxicity, leading to the completion of this invention.

SUMMARY

It is an object of the present invention to provide a compound having the antiviral activity against HCV, an optical isomer thereof, or a pharmaceutically acceptable salt thereof.

It is another object of the present invention to provide a method for preparing the said composition.

It is also an object of the present invention to provide a pharmaceutical composition comprising the said compound as an active ingredient for preventing or treating liver disease caused by hepatitis C virus.

It is further an object of the present invention to provide a health food composition comprising the said compound as an active ingredient for preventing or improving liver disease caused by hepatitis C virus.

To achieve the above objects, the present invention provides a compound represented by the following formula 1, an optical isomer thereof, or a pharmaceutically acceptable salt thereof.

[Formula 1]

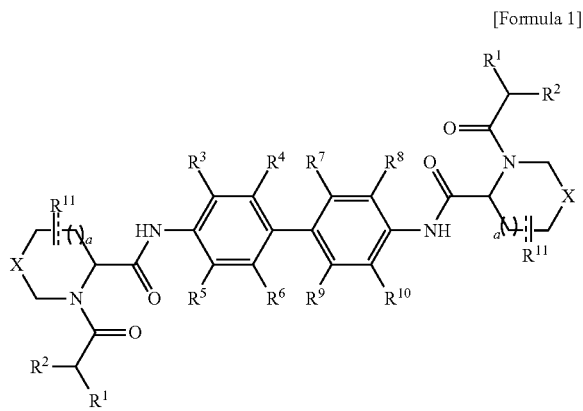

In formula 1, $R^1$ and $R^2$ are independently —H, —OH, halogen, $C_{1-10}$ straight or branched alkyl, $C_{1-10}$ straight or branched alkoxy, unsubstituted or substituted $C_{6-10}$ aryl, —$NR^{12}R^{13}$, or —NHC(=O)$R^{14}$, In the said substituted $C_{6-10}$ aryl, one or more substituents selected from the group consisting of $C_{1-5}$ straight or branched alkyl, $C_{1-5}$ straight or branched alkoxy, and halogen can be substituted, $R^{12}$ and $R^{13}$ are —H, or $C_{1-5}$ straight or branched alkyl, $R^{14}$ is H, or $C_{1-5}$ straight or branched alkoxy;

$R^1$ and $R^2$ can form $C_{5-10}$ heterocycloalkyl containing one or more hetero atoms selected from the group consisting of N, O and S along with carbon atoms which are conjugated to the same;

$R^3$, $R^4$, $R^5$, $R^6$, $R^7$, $R^8$, $R^9$, and $R^{10}$ are independently —H, halogen, or unsubstituted or substituted $C_{1-5}$ straight or branched alkyl in which one or more halogens are substituted, Wherein, $R^4$ and $R^7$, or $R^6$ and $R^9$ can form $C_{5-6}$ ring along with carbon atoms which are conjugated to the same, and the $C_{5-6}$ ring can contain one or more substituents selected from the group consisting of halogen, $C_{1-5}$ straight or branched alkyl, and =O;

X is —O—, —S—, or —$CH_2$—;

$R^{11}$ is —H, —OH, halogen, $C_{1-10}$ straight or branched alkyl, $C_{1-10}$ straight or branched alkyl alkoxy, or =O;

═ is single bond or double bond; and a is an integer of 0-3.

As presented in the following reaction formula 1, the present invention provides a method for preparing the compound represented by formula 1 comprising the following steps:

preparing the compound represented by formula 4 by reacting the compound represented by formula 2 and the compound represented by formula 3 in an organic solvent (step 1);

preparing the compound represented by formula 5 by eliminating the protection group of the compound represented by formula 4 prepared in step 1 (step 2); and preparing the compound represented by formula 1 by reacting the compound represented by formula 5 prepared in step 2 and the compound represented by formula 6 (step 3).

[Reaction Formula 1]

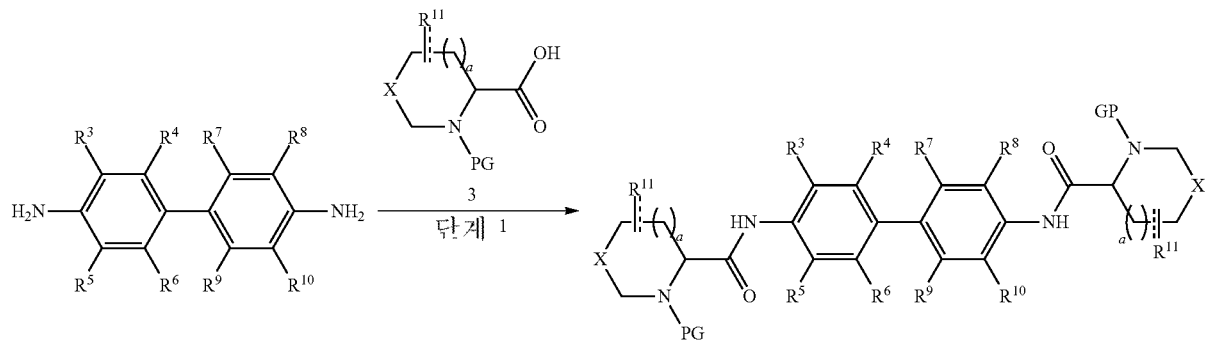

-continued

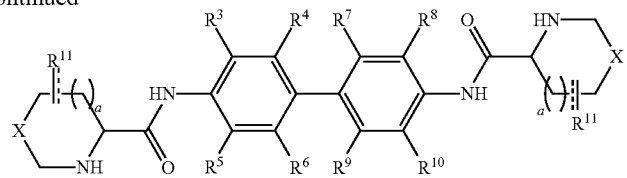

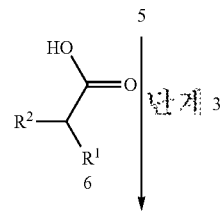

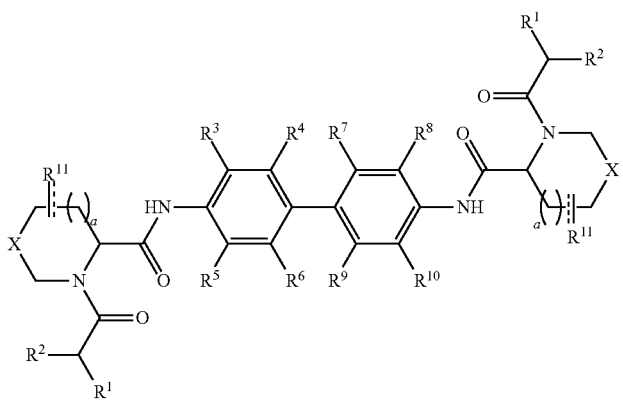

(In reaction formula 1,
R$^1$, R$^2$, R$^3$, R$^4$, R$^5$, R$^6$, R$^7$, R$^8$, R$^9$, R$^{10}$, X, a, and ═ are as defined in formula 1; and PG indicates protecting group).

The present invention also provides a pharmaceutical composition comprising the compound represented by formula 1, the optical isomer thereof, or the pharmaceutically acceptable salt thereof as an active ingredient for the prevention or treatment of liver disease caused by hepatitis C virus.

In addition, the present invention provides a health food composition comprising the compound represented by formula 1, the optical isomer thereof, or the pharmaceutically acceptable salt thereof as an active ingredient for the prevention or improvement of liver disease caused by hepatitis C virus.

Advantageous Effect

The benzidine derivative of the present invention demonstrates excellent antiviral activity including anti-virus duplication activity to suppress HCV but has no cytotoxicity, in addition to have excellent pharmaceutical activity in vivo without causing toxicity in the heart and plasma. Therefore, a pharmaceutical composition comprising the benzidine derivative as an active ingredient can be effectively used as a pharmaceutical composition for the prevention or treatment of liver disease caused by HCV such as acute hepatitis C, chronic hepatitis C, liver cirrhosis, and hepatocellular carcinoma.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
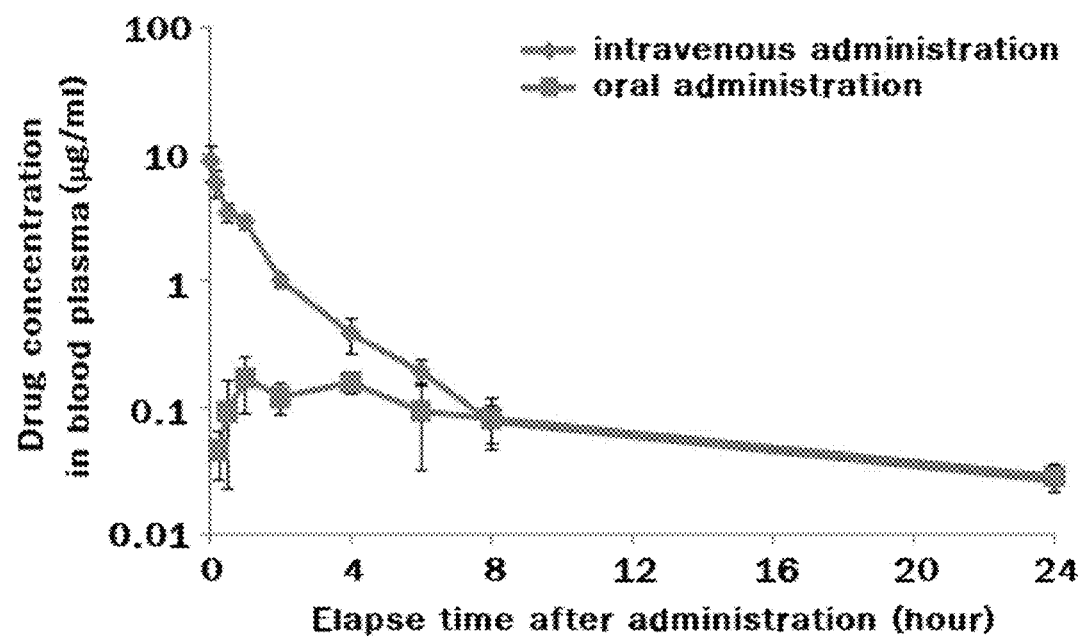
FIG. 1 is a graph illustrating the concentration of the composition of the invention in blood plasma over the treatment time, measured after the oral administration and intravenous administration of the compound of Example 4 in Experimental Example 4.

Hereinafter, the present invention is described in detail.

The present invention provides a compound represented by the following formula 1, an optical isomer thereof, or a pharmaceutically acceptable salt thereof.

[Formula 1]

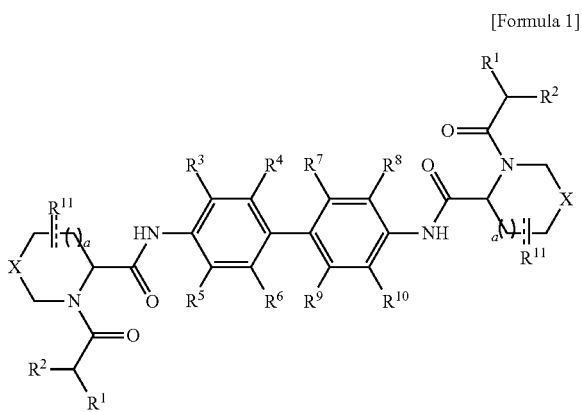

In formula 1, $R^1$ and $R^2$ are independently —H, —OH, halogen, $C_{1-10}$ straight or branched alkyl, $C_{1-10}$ straight or branched alkoxy, unsubstituted or substituted $C_{6-10}$ aryl, —$NR^{12}R^{13}$, or —NHC(=O)$R^{14}$, In the said substituted $C_{6-10}$ aryl, one or more substituents selected from the group consisting of $C_{1-5}$ straight or branched alkyl, $C_{1-5}$ straight or branched alkoxy, and halogen can be substituted, $R^{12}$ and $R^{13}$ are —H, or $C_{1-5}$ straight or branched alkyl, R14 is or $C_{1-5}$ straight or branched alkoxy;

$R^1$ and $R^2$ can form $C_{5-10}$ heterocycloalkyl containing one or more hetero atoms selected from the group consisting of N, O and S along with carbon atoms which are conjugated to the same;

$R^3$, $R^4$, $R^5$, $R^6$, $R^7$, $R^8$, $R^9$, and $R^{10}$ are independently —H, halogen, or unsubstituted or substituted $C_{1-5}$ straight or branched alkyl in which one or more halogens are substituted, Wherein, $R^4$ and $R^7$, or $R^6$ and $R^9$ can form $C_{5-6}$ ring along with carbon atoms which are conjugated to the same, and the $C_{5-6}$ ring can contain one or more substituents selected from the group consisting of halogen, $C_{1-5}$ straight or branched alkyl, and =O;

X is —O—, —S—, or —$CH_2$—;

$R^{11}$ is —H, —OH, halogen, $C_{1-10}$ straight or branched alkyl, $C_{1-10}$ straight or branched alkyl alkoxy, or =O;

═ is single bond or double bond;

a is an integer of 0-3.

Preferably, $R^1$ and $R^2$ are independently —H, —OH, halogen, $C_{1-5}$ straight or branched alkyl, $C_{1-5}$ straight or branched alkoxy, unsubstituted or substituted $C_{6-8}$ aryl, —$NR^{12}R^{13}$, or —NHC(=O)$R^{14}$, In the said substituted $C_{6-8}$ aryl, one or more substituents selected from the group consisting of $C_{1-5}$ straight or branched alkyl, $C_{1-5}$ straight or branched alkoxy, and halogen can be substituted, $R^{12}$ and $R^{13}$ are —H, or $C_{1-3}$ straight or branched alkyl, $R^{14}$ is —H, or $C_{1-3}$ straight or branched alkoxy;

$R^1$ and $R^2$ can form $C_{5-8}$ heterocycloalkyl containing one or more hetero atoms selected from the group consisting of N, O and S along with carbon atoms which are conjugated to the same;

$R^3$, $R^4$, $R^5$, $R^6$, $R^7$, $R^8$, $R^9$, and $R^{10}$ are independently —H, halogen, or unsubstituted or substituted $C_{1-5}$ straight or branched alkyl in which one or more halogens are substituted, Wherein, $R^4$ and $R^7$, or $R^6$ and $R^9$ can form $C_{5-6}$ ring along with carbon atoms which are conjugated to the same, and the $C_{5-6}$ ring can contain one or more substituents selected from the group consisting of halogen, $C_{1-5}$ straight or branched alkyl, and =O;

X is —S—, or —$CH_2$—;

$R^{11}$ is —H, —OH, $C_{1-5}$ straight or branched alkyl, $C_{1-5}$ straight or branched alkyl alkoxy, or =O;

═ is single bond or double bond;

a is an integer of 0-2.

More preferably, $R^1$ and $R^2$ are independently methyl, isopropyl, tert-butyl, phenyl, dimethylamino, diethylamino, or methoxycarbonylamino, $R^1$ and $R^2$ can form tetrahydrofuran along with carbon atoms which are conjugated to the same;

$R^3$, $R^4$, $R^5$, $R^6$, $R^7$, $R^8$, $R^9$, and $R^{10}$ are independently —H, —F, —Cl, —Br, —$CF_3$, or methyl, Wherein, $R^4$ and $R^7$, or $R^6$ and $R^9$ can form $C_5$ ring along with carbon atoms which are conjugated to the same, and the $C_5$ ring can contain one or more substituents selected from the group consisting of —F, =O, and methyl;

X is —S—, or —$CH_2$—;

$R^{11}$ is —H, or =O;

═ is single bond or double bond; and a is an integer of 0-1.

The compound represented by formula 1 can be selected from the group consisting of the following compounds.

(1) dimethyl((1R,1'R)-((2S,2'S)-2,2'-(((3,3'-dimethyl-[1,1'-biphenyl]-4,4'-diyl)bis(azandiyl))bis(carbonyl))bis(pyrrolidine-2,1-diyl))bis(2-oxo-1-phenylethane-2,1-diyl))dicarbamate;

(2) dimethyl((1R,1'R)-((2S,2'S)-2,2'-(((2,2'-bis(trifluoromethyl)-[1,1'-biphenyl]-4,4'-diyl)bis(azandiyl))bis(carbonyl))bis(pyrrolidine-2,1-diyl))bis(2-oxo-1-phenylethane-2,1-diyl))dicarbamate;

(3) dimethyl((1R,1'R)-((2S,2'S)-2,2'-(((2,2'-dimethyl-[1,1'-biphenyl]-4,4'-diyl)bis(azandiyl))bis(carbonyl))bis(pyrrolidine-2,1-diyl))bis(2-oxo-1-phenylethane-2,1-diyl))dicarbamate;

(4) dimethyl((1R,1'R)-((2S,2'S)-2,2'-(((9H-fluorene-2,7-diyl)bis(azandiyl))bis(carbonyl))bis(pyrrolidine-2,1-diyl))bis(2-oxo-1-phenylethane-2,1-diyl))dicarbamate;

(5) dimethyl((1R,1'R)-((2S,2'S)-2,2'-(((2,2'-difluoro-[1,1'-biphenyl]-4,4'-diyl)bis(azandiyl))bis(carbonyl))bis(pyrrolidine-2,1-diyl))bis(2-oxo-1-phenylethane-2,1-diyl))dicarbamate;

(6) dimethyl((1R,1'R)-((2S,2'S)-2,2'-(((2,2'-dichloro-[1,1'-biphenyl]-4,4'-diyl)bis(azandiyl))bis(carbonyl))bis(pyrrolidine-2,1-diyl))bis(2-oxo-1-phenylethane-2,1-diyl))dicarbamate;

(7) dimethyl((1R,1'R)-((2S,2'S)-2,2'-(((2,2'-dibromo-[1,1'-biphenyl]-4,4'-diyl)bis(azandiyl))bis(carbonyl))bis(pyrrolidine-2,1-diyl))bis(2-oxo-1-phenylethane-2,1-diyl))dicarbamate;

(8) dimethyl((1R,1'R)-((2R,2'R)-2,2'-(([1,1'-biphenyl]-4,4'-diylbis(azandiyl))bis(carbonyl))bis(pyrrolidine-2,1-diyl))bis(2-oxo-1-phenylethane-2,1-diyl))dicarbamate;

(9) dimethyl((1R,1'R)-((5S,5'S)-5,5'-(([1,1'-biphenyl]-4,4'-diylbis(azandiyl))bis(carbonyl))bis(3-oxopyrrolidine-5,1-diyl))bis(2-oxo-1-phenylethane-2,1-diyl))dicarbamate;

(10) dimethyl((1R,1'R)-((2S,2'S)-2,2'-(([1,1'-biphenyl]-4,4'-diylbis(azandiyl))bis(carbonyl))bis(piperidine-2,1-diyl))bis(2-oxo-1-phenylethane-2,1-diyl))dicarbamate;

(11) dimethyl((1R,1'R)-((2R,2'R)-2,2'-(((1,1'-biphenyl]-4,4'-diylbis(azandiyl))bis(carbonyl))bis(piperidine-2,1-diyl))bis(2-oxo-1-phenylethane-2,1-diyl))dicarbamate;

(12) dimethyl((1R,1'R)-((2S,2'S)-2,2'-(([1,1'-biphenyl]-4,4'-diylbis(azandiyl))bis(carbonyl))bis(2-methylpyrrolidine-2,1-diyl))bis(2-oxo-1-phenylethane-2,1-diyl))dicarbamate;
(13) dimethyl(2R,2'R)-1,1'-((2S,2'S)-2,2'-(biphenyl-4,4'-diylbis(azandiyl))bis(oxomethylene)bis(pyrrolidine-2,1-diyl))bis(3-methyl-1-oxobutane-2,1-diyl)dicarbamate;
(14) (S,2S,2'S)—N,N'-(biphenyl-4,4'-diyl)bis(1-((S)-2-(dimethylamino)-2-phenylacetyl)pyrrolidine-2-carboxamide);
(15) (S,2S,2'S)—N,N'-(biphenyl-4,4'-diyl)bis(1-((S)-2-(diethylamino)-2-phenylacetyl)pyrrolidine-2-carboxamide);
(16) dimethyl(1S,1'S)-2,2'-((2S,2S')-2,2'-(biphenyl-4,4'-diylbis(azandiyl))bis(oxomethylene)bis(pyrrolidine-2,1-diyl))bis(2-oxo-1-phenylethane-2,1-diyl)dicarbamate
(17) (R,2S,2'S)—N,N'-(biphenyl-4,4'-diyl)bis(1-((R)-tetrahydrofuran-2-carbonyl)pyrrolidine-2-carboxamide;
(18) dimethyl(2S,2'S)-1,1'-((2S,2R')-2,2'-(biphenyl-4,4'-diylbis(azandiyl))bis(oxomethylene)bis(pyrrolidine-2,1-diyl))bis(1-oxopropane-2,1-diyl)dicarbamate;
(19) dimethyl(2S,2S')-1,1'-((2S,2R')-2,2'-(biphenyl-4,4'-diylbis(azandiyl))bis(oxomethylene)bis(pyrrolidine-2,1-diyl))bis(3,3-dimethyl-1-oxobutane-2,1-diyl)dicarbamate;
(20) dimethyl(2S,2'S)-1,1'-((2S,2'R)-2,2'-(biphenyl-4,4'-diylbis(azandiyl))bis(oxomethylene)bis(pyrrolidine-2,1-diyl))bis(3-methyl-1-oxobutane-2,1-diyl)dicarbamate;
(21) dimethyl(1S,1S')-2,2'-((4R,4'R)-4,4'-(biphenyl-4,4'-diylbis(azandiyl))bis(oxomethylene)bis(thiazolidine-4,3-diyl))bis(2-oxo-1-phenylethane-2,1-diyl)bicarbamate;
(22) dimethyl((1R,1'R)-((2S,2'S)-2,2'-(((9,9-difluoro-9H-fluorene-2,7-diyl)bis(azandiyl))bis(carbonyl))bis(pyrrolidine-2,1-diyl))bis(2-oxo-1-phenylethane-2,1-diyl))dicarbamate;
(23) dimethyl((1R,1'R)-((2S,2'S)-2,2'-(((9,9-dimethyl-9H-fluorene-2,7-diyl)bis(azandiyl))bis(carbonyl))bis(pyrrolidine-2,1-diyl))bis(2-oxo-1-phenylethane-2,1-diyl))dicarbamate; and
(24) dimethyl((1R,1'R)-((2S,2'S)-2,2'-(((9-oxo-9H-fluorene-2,7-diyl)bis(azandiyl))bis(carbonyl))bis(pyrrolidine-2,1-diyl))bis(2-oxo-1-phenylethane-2,1-diyl))dicarbamate.

The compound represented by formula 1 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydriodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate and mandelate.

The acid addition salt in this invention can be prepared by the conventional method known to those in the art. For example, the compound represented by formula 1 is dissolved in an organic solvent such as methanol, ethanol, acetone, methylenechloride, or acetonitrile, to which organic acid or inorganic acid is added to induce precipitation. Then, the precipitate is filtered and dried to give the salt. Or the solvent and the excessive acid are distillated under reduced pressure, and dried to give the salt. Or the precipitate is crystallized in an organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

The present invention includes not only the compound represented by formula 1 but also a pharmaceutically acceptable salt thereof, and a solvate, a hydrate, or an optical isomer possibly produced from the same.

The compound represented by formula 1 of the present invention has excellent antiviral activity against HCV, so the pharmaceutical composition comprising the said compound as an active ingredient can be efficiently used as a pharmaceutical composition for the prevention or treatment of liver disease caused by HCV such as acute hepatitis C, chronic hepatitis C, liver cirrhosis, and hepatocellular carcinoma.

As presented in the following reaction formula 1,
the present invention provides a method for preparing the compound represented by formula 1 comprising the following steps:
preparing the compound represented by formula 4 by reacting the compound represented by formula 2 and the compound represented by formula 3 in an organic solvent (step 1);
preparing the compound represented by formula 5 by eliminating the protection group of the compound represented by formula 4 prepared in step 1 (step 2); and
preparing the compound represented by formula 1 by reacting the compound represented by formula 5 prepared in step 2 and the compound represented by formula 6 (step 3).

[Reaction Formula 1]

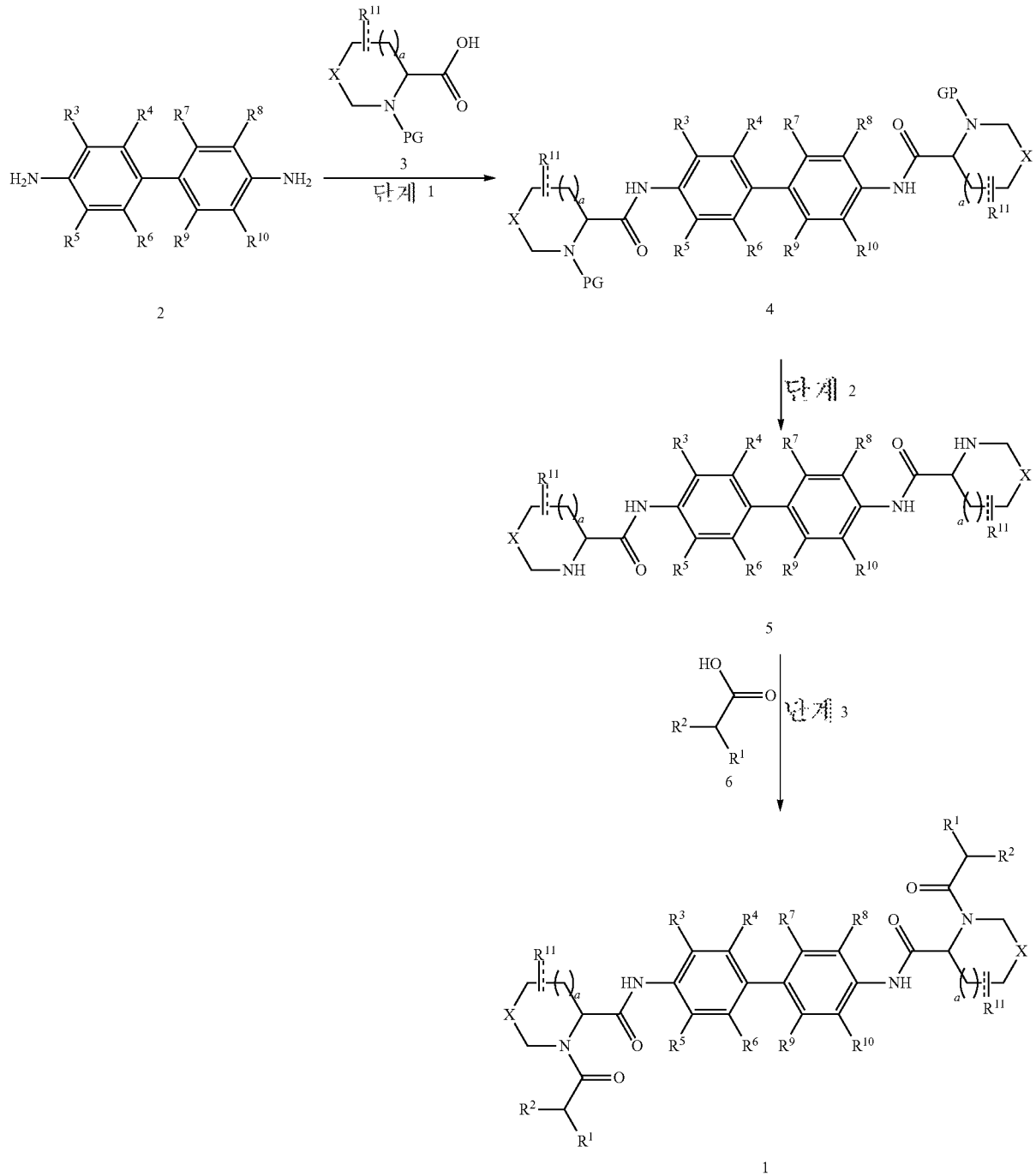

(In reaction formula 1,
$R^1$, $R^2$, $R^3$, $R^4$, $R^5$, $R^6$, $R^7$, $R^8$, $R^9$, $R^{10}$, X, a, and ═ are as defined in formula 1; and PG indicates protecting group.)

Hereinafter, the method for preparing the compound represented by formula 1 is illustrated in more detail, step by step.

In the method for preparing the compound represented by formula 1 of the present invention, step 1 is to prepare the compound represented by formula 4 by reacting the compound represented by formula 2 and the compound represented by formula 3 in the presence of an amide reagent in an organic solvent. More precisely, this step is to prepare the compound represented by formula 4, the coupling product, by inducing amidation between the amine group of the compound represented by formula 2 and the carboxyl group of the compound represented by formula 3 in the presence of an amide reagent.

At this time, the usable amide reagent is diisopropylethylamine (DIPEA), triethylamine (TEA), or dimethylaminopyridine (DMAP) along with benzotriazole-1-yl-oxy-tris (dimethylamino)-phosphoniumhexafluorophosphate (PyBOP), O-benzotriazole-N,N,N,N-tetramethyl-uronium-hexafluoro-phosphate (HBTU), 2-(7-aza-1H-benzotriazole-1-yl)-1,1,3,3-tetramethyluroniumhexafluorophosphate (HATU), hydroxybenzotriazole (HOBt), dicyclohexylcarbodiimide (DCC), 1-ethyl-3-(3-dimethylaminopropyl)carbodiimide (EDC), or carbonyldiimidazole (CDI), and preferably 1-ethyl-3-(3-dimethylaminopropyl)carbodiimide (EDC).

The organic solvent herein is exemplified by methanol, dimethylformamide, tetrahydrofuran, dichloromethane, and toluene, which can be used independently or together as a mixed solvent, and more preferably exemplified by dichloromethane.

Further, the reaction temperature is preferably 0° C.~the boiling point of a solvent, and the reaction time is not limited but preferably 0.5~10 hours.

In the method for preparing the compound represented by formula 1 of the present invention, step 2 is to prepare the compound represented by formula 5 by eliminating the protecting group from the compound represented by formula 4 prepared in step 1. More precisely, this step is to prepare the compound represented by formula 5 by deprotecting the amine protecting group (PG) included in the compound represented by formula 4 prepared in step 1 using a deprotecting agent.

At this time, the amine protecting group (PG) included in the compound represented by formula 4 is exemplified by t-butoxycarbonyl (Boc), 9H-fluorene-9-ylmethoxycarbonyl (Fmoc), trityl, benzyl, chloroacetyl, benzyloxycarbonyl, p-methoxybenzyloxycarbonyl, formyl, trifluoroacetyl, p-toluenesulfonyl, benzenesulfonyl, methanesulfonyl, p-nitrobenzyloxycarbonyl, 2,2,2-trichloroethoxycarbonyl, and allyloxycarbonyl (Alloc), and more preferably t-butoxycarbonyl (Boc).

The deprotecting condition in step 2 of the method is same as the deprotecting condition generally used according to the protecting group.

The reaction temperature herein is preferably 0° C.~the boiling point of a solvent, and the reaction time is not limited but preferably 0.5~10 hours.

In the method for preparing the compound represented by formula 1 of the present invention, step 3 is to prepare the compound represented by formula 1 by reacting the compound represented by formula 5 prepared in step 2 and the compound represented by formula 6 in the presence of an amide reagent. More precisely, this step is to prepare the compound represented by formula 1 via amidation between the amine group included in the compound represented by formula 5 and the carboxyl group included in the compound represented by formula 6.

At this time, the usable amide reagent is diisopropylethylamine (DIPEA), triethylamine (TEA), or dimethylaminopyridine (DMAP) along with benzotriazole-1-yl-oxy-tris (dimethylamino)-phosphoniumhexafluorophosphate (PyBOP), O-benzotriazole-N,N,N,N-tetramethyl-uronium-hexafluoro-phosphate (HBTU), 2-(7-aza-1H-benzotriazole-1-yl)-1,1,3,3-tetramethyluroniumhexafluorophosphate (HATU), hydroxybenzotriazole (HOBt), dicyclohexylcarbodiimide (DCC), 1-ethyl-3-(3-dimethylaminopropyl)carbodiimide (EDC), or carbonyldiimidazole (CDI), and preferably 1-ethyl-3-(3-dimethylaminopropyl)carbodiimide (EDC).

The organic solvent herein is exemplified by methanol, dimethylformamide, tetrahydrofuran, dichloromethane, and toluene, which can be used independently or together as a mixed solvent, and more preferably exemplified by dichloromethane.

Further, the reaction temperature is preferably 0° C.~the boiling point of a solvent, and the reaction time is not limited but preferably 0.5~10 hours.

The present invention also provides a pharmaceutical composition comprising the compound represented by formula 1, the optical isomer thereof, or the pharmaceutically acceptable salt thereof as an active ingredient for the prevention or treatment of liver disease caused by hepatitis C virus.

In the pharmaceutical composition of the present invention, the liver disease caused by HCV is exemplified by acute hepatitis C, chronic hepatitis C, liver cirrhosis, and hepatocellular carcinoma.

The present inventors evaluated the anti-HCV activity of the compound represented by formula 1. Particularly, the liver cancer cells inoculated with HCV containing luciferase gene were treated with 1 μM of the compound represented by formula 1. As a result, HCV was suppressed by a low concentration of the compound of formula 1 (see Experimental Example 1).

When the duplicated HCV was treated with the compound represented by formula 1 of the invention, $EC_{50}$ indicating the concentration that demonstrates the antiviral activity was low, and particularly $EC_{50}$ of each of those compounds prepared in Examples 2, 3, 4, 5, 6, 7, 9, 16, 21, 22, 23, and 24 was significantly low (see Experimental Example 2). Therefore, it was confirmed that the antiviral activity particularly against HCV of the compound represented by formula 1 of the invention was excellent.

Particularly, the compound represented by formula 1 of the present invention takes NS5A (nonstructural protein 5A) known as a necessary factor for RNA replication in virus as a target. The said NS5A is a phosphorylated viral protein in the size of 56 kDa which is involved in HCV replication. This protein has the amphipathic alpha helix structure that catalyzes the adherence to host cell membrane, and is composed of 1~3 domains which are responsible for virus RNA replication, work as zinc binding motif (Cys 39, 57, 59, and 80), bind to PI3K, PKR, and NS5B, and are involved in virus assembly.

The known NS5A inhibitors are ACH-2928, AZD-7295, PPI-461, BMS B24393, GS-5885, and Vertex, etc.

Since NS5A has a unique zinc binding site, it is expected that when the compound represented by formula 1 of the invention is bound thereto, it could play as a NS5A inhibitor with displaying the antiviral activity against HCV as well. It can provide a reason for the further study on that.

The present inventors further studied cytotoxicity of the compounds of Example 1~Example 21 according to the present invention. As a result, these compounds did not display cytotoxicity at the concentration of 1 μM. This result indicates that the compound represented by formula 1 of the invention has a very low cytotoxicity (see Experimental Example 3).

Pharmacodynamics experiment was performed with the compound represented by formula 1 of the present invention. As a result, the maximum concentration in blood was detected within 2 hours and bioavailability was 20%. Therefore, it was confirmed that the compound of the invention had excellent physiological effect (see Experimental Example 4, and FIGS. 1 and 2).

Binding capacity of the compound represented by formula 1 of the invention to hERG (human Ether-a-go-go-Related Gene) ligand was investigated. As a result, the effective dosage of the compound of Example 16 to inhibit hERG, measured by polarization degree, was 9.8 μM. In the meantime, the effective dosage of Astemizole, which has been known as a hERG inhibitor and used herein as the control, was 0.00019 μM, suggesting that the control had approximately 5160 times higher hERG inhibitory activity than the compound of Example 16.

Since the compound of Example 16 of the present invention showed a significantly low hERG inhibitory activity, it can be expected that the compound hardly has any side effect such as cardiotoxicity that can induce sudden death (see Experimental Example 5).

Plasma stability (in vivo cytotoxicity) of the compound represented by formula 1 of the present invention was evaluated. As a result, the plasma survival rate in the mouse treated with the compound of Example 16 was at least 99% even 4 hours after the treatment. This result suggests that the compound of Example 16 of the invention has no in vivo cytotoxicity (see Experimental Example 6).

The compound represented by formula 1 of the present invention has excellent antiviral activity against HCV but has no cytotoxicity in cells and in the heart, suggesting that the compound is safe in human body, and also displays excellent physiological activity in vivo and can be co-administered with other drugs, suggesting the high chance of application to various treatment methods. Therefore, the pharmaceutical composition comprising the said compound as an active ingredient can be efficiently used as a pharmaceutical composition for the prevention or treatment of liver disease caused by HCV, such as acute hepatitis C, chronic hepatitis C, cirrhosis, and hepatocellular carcinoma.

The pharmaceutical composition of the present invention comprising the compound represented by formula 1 or the pharmaceutically acceptable salt thereof as an active ingredient can be administered orally or parenterally and be used in general forms of pharmaceutical formulation, but not always limited thereto.

The formulations for oral administration are exemplified by tablets, pills, hard/soft capsules, solutions, suspensions, emulsions, syrups, granules, elixirs, and troches, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrrolidone, and if necessary disintegrating agents such as starch, agarose, alginic acid or its sodium salt or azeotropic mixtures and/or absorbents, coloring agents, flavors, and sweeteners can be additionally included thereto.

The pharmaceutical composition of the present invention comprising the compound represented by formula 1 as an active ingredient can be administered by parenterally and the parenteral administration includes subcutaneous injection, intravenous injection, intramuscular injection and intrathoracic injection.

To prepare the composition as a formulation for parenteral administration, the compound represented by formula 1 or the pharmaceutically acceptable salts thereof of the present invention are mixed with a stabilizer or a buffering agent to produce a solution or suspension, which is then formulated as ampoules or vials. The composition herein can be sterilized and additionally contains preservatives, stabilizers, wettable powders or emulsifiers, salts and/or buffers for the regulation of osmotic pressure, and other therapeutically useful materials, and the composition can be formulated by the conventional mixing, granulating or coating method.

The effective dosage of the pharmaceutical composition comprising the compound represented by formula 1 as an active ingredient of the present invention can be adjusted according to the age, weight, and gender of patient, administration pathway, health condition, severity of disease, etc. For example, the preferable dosage is 0.01~200 mg/kg/day, which can be administered 1~3 times a day or the dosage can be divided and administered several times a day at a regular interval according to the judgment of a doctor or a pharmacist.

The present invention also provides a health food composition comprising the compound represented by formula 1, the optical isomer thereof, or the pharmaceutically acceptable salt thereof as an active ingredient for the prevention or improvement of liver disease caused by hepatitis C virus.

In the health food composition of the invention, the liver disease caused by HCV is exemplified by acute hepatitis C, chronic hepatitis C, cirrhosis, and hepatocellular carcinoma.

The health food composition comprising the compound represented by formula 1 of the present invention can be applied to any heath functional food or beverage for the purpose of preventing or improving liver disease caused by HCV.

The food herein is not limited. For example, the composition of the present invention can be added to drinks, meats, sausages, breads, biscuits, rice cakes, chocolates, candies, snacks, cookies, pizza, ramyuns, flour products, gums, dairy products including ice cream, soups, beverages, alcohol drinks and vitamin complex, etc, and in a wide sense, almost every food applicable in the production of health food can be included.

The compound represented by formula 1 of the present invention can be used as a food additive. In that case, the compound can be added as it is or as mixed with other food components according to the conventional method. The mixing ratio of active ingredients can be regulated according to the purpose of use (prevention or improvement). In general, to produce health food or beverages, the compound represented by formula 1 of the present invention is added preferably by 0.1~90 weight part. However, if long term administration is required for health and hygiene or regulating health condition, the content can be lower than the above but higher content can be accepted as well since the compound of the present invention has been proved to be very safe.

The health beverages containing the composition of the present invention can additionally include various flavors or natural carbohydrates, etc, like other beverages. The natural carbohydrates above can be one of monosaccharides such as glucose and fructose, disaccharides such as maltose and sucrose, polysaccharides such as dextrin and cyclodextrin, and sugar alcohols such as xilytole, sorbitol and erythritol. Besides, natural sweetening agents (for example, thaumatin, *stevia* extract, etc.) and synthetic sweetening agents (for example, saccharin, aspartame, etc.) can be included as a sweetening agent. The content of the natural carbohydrate is preferably 1~20 g and more preferably 5~12 g in 100 ml of the health beverages of the invention.

In addition to the ingredients mentioned above, the health food composition comprising the compound represented by formula 1 of the present invention can include in variety of nutrients, vitamins, minerals (electrolytes), flavors including natural flavors and synthetic flavors, coloring agents and extenders (for example, cheese, chocolate, etc.), pectic acid and its salts, alginic acid and its salts, organic acid, protective colloidal viscosifiers, pH regulators, stabilizers, antiseptics, glycerin, alcohols, carbonators which used to be added to soda, etc. The health food composition of the present invention can also include natural fruit juice, fruit beverages and fruit flesh addable to fruit/vegetable beverages.

All the mentioned ingredients can be added singly or together. The mixing ratio of those ingredients does not matter in fact, but in general, each can be added by 0.1~20 weight part per 100 weight part of the health food composition of the invention.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Preparative Example 1

Preparation of (S)-2-(methoxycarbonylamino)-3-methylbutanoic acid

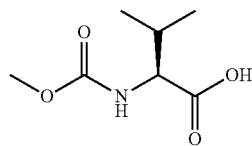

Sodium carbonate (1.83 g, 17.2 mmol) was added to 1 M sodium hydroxide solution (33 ml, 33 mmol) containing L-valine (3.9 g, 33.29 mmol) dissolved therein, which was cooled down by using ice water. Methyl chloroformate (2.8 ml, 36.1 mmol) was slowly added to the cooled reaction mixture. Once the loading was completed, the iced water was eliminated and the temperature of the mixture was raised to room temperature, followed by stirring for 3.25 hours. Then, the reaction product was washed with ether (17 ml) three times. The water later was cooled down with ice water and then acidized with HCl (conc. HCl) to pH 1~pH 2. The acidized water layer was extracted with dichloromethane (17 ml) three times, and the extracted organic was dried over $MgSO_4$ and filtered. The filtered organic layer was concentrated under reduced pressure and as a result the target compound was obtained as a white solid (5 g, yield: 86%) without any additional purification procedure.

$^1$H NMR (400 MHz, DMSO-$d_6$, δ=2.5 ppm): 12.51 (br s, 1H), 7.32 (d, 1H), 3.84 (t, 1H), 3.54 (s, 3H), 2.03 (m, 1H), 0.88 (d, J=12, 6H).

Preparative Example 2

Preparation of (R)-2-(methoxycarbonylamino)-3-methylbutanoic acid

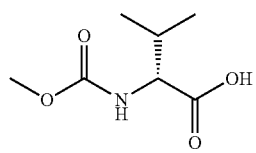

The target compound was obtained as a white solid (760 mg, yield: 87%) by the same manner as described in Preparative Example 1 except that D-valine (586 mg, 5 mmol) was used instead of L-valine (3.9 g, 33.29 mmol).

$^1$H NMR (400 MHz, DMSO-$d_6$, δ=2.5 ppm): 12.54 (s, 1H), 7.32 (d, 1H), 3.84 (t, 1H), 3.54 (s, 3H), 2.03 (m, 1H), 0.87 (d, 6H).

Preparative Example 3

Preparation of (R)-2-(dimethylamino)-2-phenylacetic acid

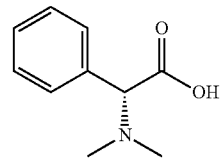

D-phenylglycine (1.51 g, 10 mmol), formaldehyde (5 ml, 37 weigh % aqueous solution), and 1 N HCl (4.5 ml) were mixed in methanol (4.5 ml). This mixture was added to methanol (1.5 ml) containing 10% Pd/C (310 mg, 0.3 mmol), to which hydrogen gas ($H_2$) was injected, followed by stirring overnight. Then, the reaction mixture was filtered with celite and the filtrate was concentrated under reduced pressure. The concentrated mixture was re-crystallized with isopropanol to give the target compound as a white acicular hydrochloride (1.84 g, yield: 89%).

$^1$H NMR (600 MHz, DMSO-$d_6$, δ=2.5 ppm): 7.43-7.39 (m, 5H), 4.47 (s, 1H), 2.43 (s, 6H).

Preparative Example 4

Preparation of (R)-2-(diethylamino)-2-phenylacetic acid

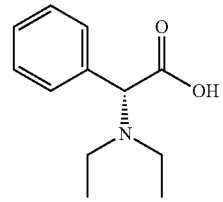

The mixture of D-phenylglycine (756 mg, 5 mmol) dissolved in methanol (13 ml) was cooled down with ice water, to which sodiumcyanoborohydride (786 mg, 12.5 mmol) was added for several minutes not all at once but many times spread over the time, followed by stirring for 5 minutes. Acetaldehyde (1.3 ml, 22.5 mmol) was slowly added to the reaction mixture, which was stirred for 45 minutes, during which a low temperature was maintained. The temperature was raised to room temperature, followed by stirring for 6.5 hours. While stirring, the mixture was cooled down again with ice water, to which HCl (conc. HCl) was loaded to acidize the reaction mixture to be pH 1.5~2.0. The temperature of the acidized reaction mixture was slowly raised to room temperature, followed by stirring overnight. The reaction was terminated and then the reaction product was filtered to remove floating materials. The filtrate was concentrated under reduced pressure. The concentrated mixture was re-crystallized with ethanol to give the target compound as a white hydrochloride (625 mg, yield: 60%).

¹H NMR (600 MHz, DMSO-d₆, δ=2.5 ppm): 10.77 (br s, 1H), 7.72 (m, 2H), 7.51 (m, 3H), 5.33 (s, 1H), 3.17 (app br s, 2H), 3.01 (app br s, 2H), 1.20 (app br s, 6H).

Preparative Example 5

Preparation of (R)-2-(methoxycarbonylamino)-2-phenylacetic acid

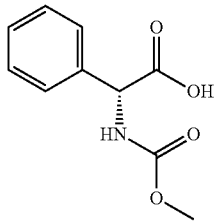

The target compound was obtained as a white solid (760 mg, yield: 87%) by the same manner as described in Preparative Example 1 except that D-phenylglycine (1.5 g, 10 mmol) was used instead of L-valine (3.9 g, 33.29 mmol).

¹H NMR (600 MHz, DMSO-d₆, δ=2.5 ppm): 12.79 (br s, 1H), 7.96 (d, J=12, 1H), 7.40-7.29 (m, 5H), 5.13 (d, J=12, 1H), 3.55 (s, 3H).

Preparative Example 6

Preparation of (S)-2-(methoxycarbonylamino)propanoic acid

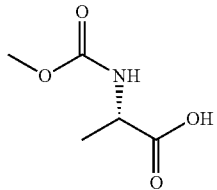

The target compound was obtained as a colorless oil (0.83 g, yield: 56%) by the same manner as described in Preparative Example 1 except that L-alanine (0.89 g, 10 mmol) was used instead of L-valine (3.9 g, 33.29 mmol).

¹H NMR (600 MHz, δ=7.26 ppm, CDCl₃): 10.00 (br s, 1H), 5.49 (d, J=12, 1H), 4.38 (m, 1H), 3.69 (s, 3H), 1.45 (d, J=12, 3H).

Preparative Example 7

Preparation of (S)-2-(2-methoxy-2-oxoethyl)-3,3-dimethylbutanoic acid

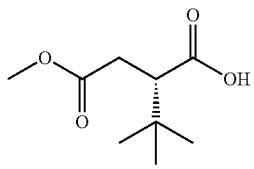

The target compound was obtained as a white solid (0.67 g, yield: 71%) by the same manner as described in Preparative Example 1 except that L-tert-leucine (0.656 g, 5 mmol) was used instead of L-valine (3.9 g, 33.29 mmol).

¹H NMR (600 MHz, δ=7.26 ppm, CDCl₃): 9.57 (br s, 1H), 5.31 (d, 1H), 4.20 (d, 1H), 3.70 (s, 3H), 1.03 (s, 9H).

Preparative Example 8

Preparation of (S)-3-(tert-butoxycarbonyl)thiazolidine-4-carboxylic acid

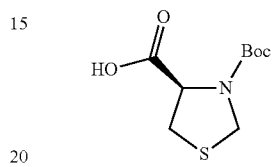

Acetonitrile (50 ml), triethylamine (26 ml), and distilled water (50 ml) were mixed, to which L-thioproline (10 g, 75 mmol) was added. The mixed solution was cooled down to 0° C., to which di-tert-butyldicarbonate (21.3 g, 98 mmol) was added. The temperature of the mixture was slowly raised to room temperature with stirring for 18 hours. Then, the reaction product was distilled to eliminate acetonitrile and the mixture was acidized with 1 N HCl to make pH 2. The acidized reaction product was extracted with ethylacetate. The extracted organic layer was washed with brine, and then dried over MgSO₄. The dried organic layer was filtered and the filtered organic layer was distilled under reduced pressure to give the target compound (17 g, yield: 97%).

¹H NMR (600 MHz, DMSO-d₆, δ=2.5 ppm): 12.87 (s, 1H), 4.62-4.52 (m, 1H), 4.87 (d, 1H), 4.29 (m, 1H), 3.36 (m, 1H), 3.10 (m, 1H), 1.38-1.34 (app br s, 9H);

¹³C NMR (600 MHz, DMSO-d₆, δ=39.52 ppm): 171.85, 152.59, 79.94, 61.01, 48.56, 33.95, 27.85.

Preparative Example 9

Preparation of (R)-2-(methoxycarbonylamino)-2-phenylacetic acid

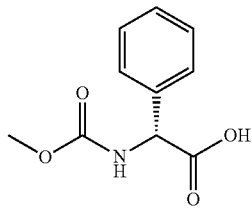

D-phenylglycine (1.5 g, 10 mmol) was dissolved in sodium hydroxide solution (10 ml, 10 mmol), to which sodium carbonate (0.55 g, 5.2 mmol) was added. The mixture was cooled down with ice water. The cooled reaction mixture was slowly added with methylchloroformate (0.85 ml, 11.0 mmol). Then, ice water was eliminated and the temperature of the mixture was raided to room temperature with stirring for 3.25 hours. The reaction product was washed with ether (18 ml) three times, followed by cooling down in ice water bath. The mixture was acidized with HCl (conc. HCl) to make pH 1~2. The acidized water layer was extracted with dichloromethane (18 ml) three times, and the extracted organic layer was dried over MgSO₄ and filtered.

The filtered organic layer was concentrated under reduced pressure. The remaining oil residue was treated with diethylether/hexane (~5:4; 10 ml) to obtain a precipitate. The obtained precipitate was washed with diethylether/hexane (~1:3), and vacuum-dried to give the target product as a white solid (1.4 g, yield: 67%).

$^1$H NMR (DMSO-$d_6$, δ=2.5 ppm, 500 MHz): 12.79 (br s, 1H), 7.96 (d, J=12, 1H), 7.40-7.29 (m, 5H), 5.13 (d, J=12, 1H), 3.55 (s, 3H).

Preparative Example 10

Preparation of 9,9-dimethyl-9H-fluorene-2,7-diamine

1: Preparation of 9,9-dimethyl-2,7-dinitro-9H-fluorene

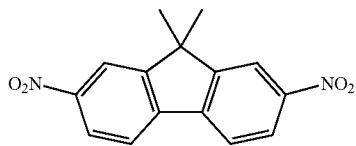 [SMILES: CC1(C)c2cc([N+](=O)[O-])ccc2-c2ccc([N+](=O)[O-])cc21]

The mixture of 2,7-nitro-9H-fluorene (100 mg, 0.39 mmol) and NaOt-Bu (75 mg, 0.78 mmol) was dissolved in DMF in an ice water bath in nitrogen atmosphere. Iodomethane (49 mL, 0.78 mmol) was slowly added to the mixture, followed by well-mixing for 2 hours. Water was added to the mixture to obtain a precipitate. The precipitate was filtered and washed with water and dried. Without any purification process, the target compound was obtained as a yellow solid (89 mg, yield: 80%).

$^1$H NMR (DMSO-$d_6$, δ=2.5 ppm, 400 MHz): 8.59 (d, 2H), 8.33 (m, 4H), 1.60 (s, 6H).

$^{13}$C NMR (DMSO-$d_6$, δ=39.52 ppm, 100 MHz): 156.2, 148.1, 142.7, 123.6, 122.9, 118.7, 47.9, 25.6.

Step 2: Preparation of 9,9-dimethyl-9H-fluorene-2,7-diamine

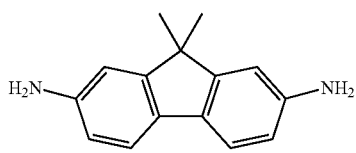

Fe$_3$O$_4$ (15 mg, 0.063 mmol) and DMF (1.9 mL) were loaded in the oven-dried Schlenk tube, followed by sonication for 1 minute in the ultrasound bath in argon atmosphere. The 9,9-diethyl-2,7-dinitro-9H-fluorene (90 mg, 0.32 mmol) obtained in step 1 and hydrazine monohydrate (123 mL, 2.52 mmol) were added to the mixture. The reaction mixture was well-mixed at 80° C. in argon atmosphere until the reaction was completed. Magnetic separation was performed by using a catalyst. The organic layer was vacuum-concentrated. The residue was separated with CH$_2$Cl$_2$ and H$_2$O. The organic layer was washed with brine, dried over MgSO$_4$, filtered, and vacuum-concentrated. Without any purification process, the target compound was obtained as a yellow solid (69 mg, yield: 98%).

$^1$H NMR (DMSO-$d_6$, δ=2.5 ppm, 400 MHz): 7.21 (s, 1H), 7.19 (s, 1H), 6.6 (d, 2H), 6.47 (d, 1H), 6.45 (d, 1H), 4.9 (s, 4H), 1.3 (s, 6H).

$^{13}$C NMR (DMSO-$d_6$, δ=39.52 ppm, 100 MHz): 153.5, 146.7, 128.4, 118.6, 112.6, 108.5, 45.6, 27.7.

$^{19}$F NMR (DMSO-$d_6$, 377 MHz,): δ–106.7. LC/MS: Anal. Calcd.

For [M+H]$^+$ C$_{15}$H$_{16}$N$_2$: 225.1386. found 225.1383.

Preparative Example 11

Preparation of 9,9-difluoro-9H-fluorene-2,7-diamine

Step 1: Preparation of 9,9-difluoro-2,7-dinitro-9H-fluorene

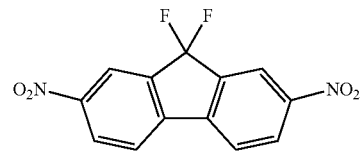 [SMILES: O=[N+]([O-])c1ccc2c(c1)C(F)(F)c1cc([N+](=O)[O-])ccc1-2]

2,7-Nitro-9H-fluorene (100 mg, 0.39 mmol) and N-fluorobenzenesulfonimide (NFSI) (369 mg, 1.17 mmol) were dissolved in DMF, which was frozen at −20° C. NaHMDS (1.0 M in THF, 1.17 mL, 1.17 mmol) was added thereto for 5 minutes drop by drop. The mixture stood at 0° C. for 2 hours. When the termination of the reaction was confirmed by TLC, MeOH was added to quench excessive base. The suspension was filtered with celite, followed by vacuum-concentration. The residue was obtained on silica gel mesh, followed by flash chromatography (silica gel: EtOAc/hexane as eluent) to give the target compound as a yellow solid (22 mg, yield: 19%).

$^1$H NMR (DMSO-$d_6$, δ=2.5 ppm, 400 MHz): 8.63 (d, 2H), 8.53 (d, 1H), 8.56 (d, 1H), 8.36 (s, 1H), 8.34 (s, 1H).

$^{13}$C NMR (DMSO-$d_6$, δ=39.52 ppm, 100 MHz): 149.1, 142.5, 138.5, 129.2, 144.3, 120.8, 119.6.

$^{19}$F NMR (DMSO-$d_6$, 377 MHz,): δ–110.3.

Step 2: Preparation of 9,9-difluoro-9H-fluorene-2,7-diamine

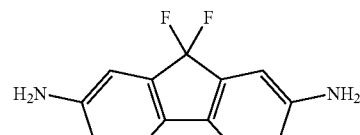

Fe$_3$O$_4$ (4 mg, 0.015 mmol) and DMF (0.5 mL) were loaded in the oven-dried Schlenk tube, followed by sonication for 1 minute in the ultrasound bath in argon atmosphere. The 9,9-difluoro-2,7-dinitro-9H-fluorene (22 mg, 0.075 mmol) obtained in step 1 and hydrazine monohydrate (29 µl, 0.60 mmol) were added to the mixture. The reaction mixture was well-mixed at 80° C. in argon atmosphere until the reaction was completed. Magnetic separation was performed by using a catalyst. The organic layer was vacuum-concentrated. The residue was separated with CH$_2$Cl$_2$ and H$_2$O. The organic layer was washed with brine, dried over MgSO$_4$, filtered, and vacuum-concentrated. Without any purification process, the target compound was obtained as a yellow solid (17 mg, yield: 98%).

$^1$H NMR (DMSO-d$_6$, δ=2.5 ppm, 400 MHz): 7.19 (s, 1H), 7.17 (s, 1H), 6.8 (d, 2H), 6.61 (d, 1H), 6.59 (d, 1H), 5.3 (s, 4H).

$^{13}$C NMR (DMSO-d$_6$, δ=39.52 ppm, 100 MHz): 148.0, 137.3, 137.1, 127.7, 123.7, 119.8, 116.45, 109.1.

$^{19}$F NMR (DMSO-d$_6$, 377 MHz,): δ–106.7.

LC/MS: Anal. Calcd. For [M+H]$^+$ C$_{13}$H$_{10}$F$_2$N$_2$: 233.0885. found 233.0885.

Preparative Example 12

Preparation of 2,7-diamino-9H-fluorene-9-one

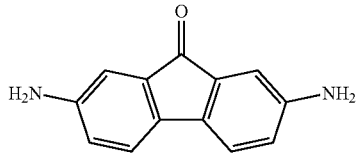 [SMILES: Nc1ccc2c(c1)C(=O)c1cc(N)ccc1-2]

The mixture of 9H-fluorene-2,7-diamine (294 mg, 1.5 mmol) and Cs$_2$CO$_3$ (1.5 g, 4.5 mmol) were dissolved in DMSO (7 mL), followed by mixing under an atmosphere of air. When the termination of the reaction was confirmed by TLC, water was added to the mixture to obtain a precipitate. The precipitate was filtered and washed with water and dried. Without any purification process, the target compound was obtained as a solid (239 mg, yield: 76%).

$^1$H NMR (DMSO-d$_6$, δ=2.5 ppm, 400 MHz): 7.10 (s, 1H), 7.08 (s, 1H), 6.70 (d, 2H), 6.57 (d, 1H), 6.57 (d, 1H) 5.30 (s, 4H).

$^{13}$C NMR (DMSO-d$_6$, δ=39.52 ppm, 100 MHz): 194.9, 148.2, 134.6, 133.3, 119.9, 118.6, 109.7.

LC/MS: Anal. Calcd. For [M+H]$^+$ C$_{13}$H$_{10}$N$_2$O: 211.0866. found 211.0867.

Example 1

Preparation of dimethyl((1R,1'R)-((2S,2'S)-2,2'-(((3,3'-dimethyl-[1,1'-biphenyl]-4,4'-diyl)bis(azandiyl))bis(carbonyl))bis(pyrrolidine-2,1-diyl))bis(2-oxo-1-phenylethane-2,1-diyl))dicarbamate N-Boc-L-proline (9.47 g, 44.0 mmol), EDC (9.97 g, 52.0 mmol), and ortho-tolidine (4.25 g, 20.0 mmol) were mixed in CH$_2$Cl$_2$ (30 mL), followed by stirring at room temperature for 2 hours.

Then, the obtained mixture was fractionated with CH$_2$Cl$_2$ and H$_2$O. The organic layer was washed with 1 N HCl aqueous solution and brine, dried over MgSO$_4$, filtered, and concentrated under reduced pressure. Without any additional purification process, 2,2'-(((3,3'-dimethyl-[1,1'-biphenyl]-4,4'-diyl)bis(azandiyl))bis(carbonyl))bis(pyrrolidine-1-carboxylate), the target compound, was obtained as a solid (11.3 g, yield: 93%).

The obtained mixture (144 mg, 0.238 mmol) was loaded in the mixed solvent of CF$_3$CO$_2$H (1 mL) and CH$_2$Cl$_2$ (1 mL), followed by stirring at room temperature for 5 hours. The volatile components were eliminated under reduced pressure and CH$_2$Cl$_2$ (1 mL) solution containing i-Pr$_2$NEt (208 µl, 1.192 mmol) dissolved in there was loaded thereto for 4 minutes. EDC (119 mg, 0.620 mmol) and the compound (100 mg, 0.572 mmol) prepared in Preparative Example 9 were additionally added to the reaction mixture, followed by stirring at room temperature for 75 minutes. The residue was fractionated with CH$_2$Cl$_2$ and H$_2$O. The organic layer was washed with H$_2$O and brine, dried over MgSO$_4$, filtered, and concentrated under reduced pressure. The residue proceeded to silica gel mesh, followed by flash chromatography (eluent: EtOAc/hexane mixture) to give the target compound as a white solid (77 mg, yield: 41%).

$^1$H NMR (DMSO-d$_6$, δ=2.5 ppm, 400 MHz): 9.31 (s, 2H), 7.74 (d, 2H), 7.54-7.23 (m, 16H), 5.52 (d, 2H), 4.52 (m, 2H), 3.85 (m, 2H), 3.52 (s, 6H), 3.18 (m, 2H), 2.28 (s, 6H), 2.00-1.82 (m, 8H);

$^{13}$C NMR (DMSO-d$_6$, δ=39.52 ppm, 100 MHz): 170.1, 168.8, 156.1, 137.1, 136.5, 135.4, 132.2, 128.6, 128.2, 128.1, 128.0, 125.2, 123.9, 60.6, 56.8, 51.6, 46.9, 29.1, 24.3, 17.9;

LC/MS: Anal. Calcd. For [M+H]$^+$ C$_{44}$H$_{48}$N$_6$O$_8$: 789.3606. found 789.3597.

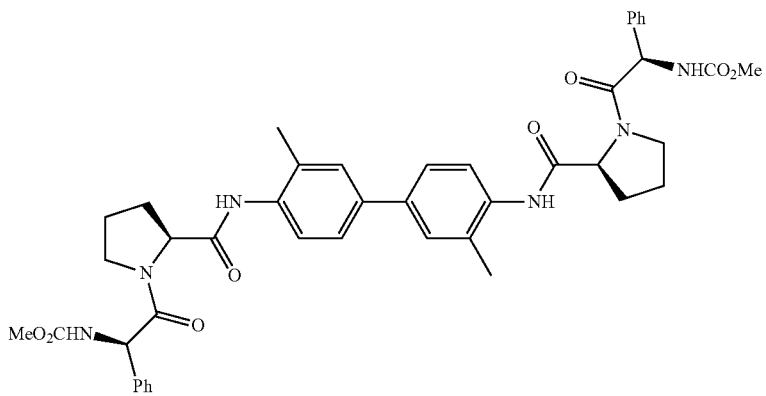

Example 2

Preparation of dimethyl((1R,1'R)-((2S,2'S)-2,2'-(((2,2'-bis(trifluoromethyl)-[1,1'-biphenyl]-4,4'-diyl)bis(azandiyl))bis(carbonyl))bis(pyrrolidine-2,1-diyl))bis(2-oxo-1-phenylethane-2,1-diyl))dicarbamate

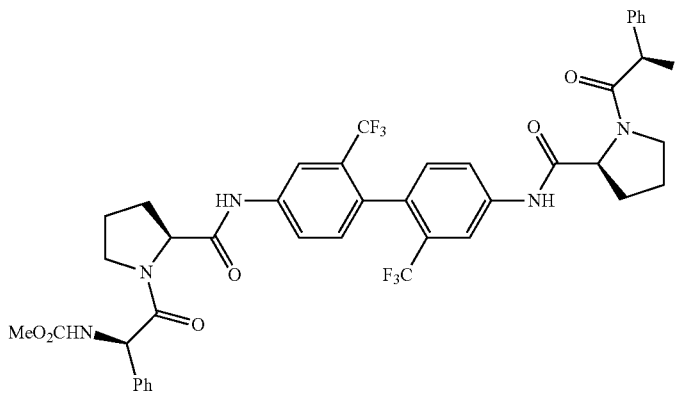

N-Boc-L-proline (3.23 g, 15.0 mmol), EDC (3.12 g, 16.3 mmol), and 2,2'-bis(trifluoromethyl)benzidine (2.00 g, 6.3 mmol) were mixed in $CH_2Cl_2$ (20 mL), followed by stirring at room temperature for 2 hours.

Then, the obtained mixture was fractionated with $CH_2Cl_2$ and $H_2O$. The organic layer was washed with 1 N HCl aqueous solution and brine, dried over $MgSO_4$, filtered, and concentrated under reduced pressure. Without any additional purification process, (2S,2'S)-di-tert-butyl 2,2'-(((2,2'-bis(trifluoromethyl)-[1,1'-biphenyl]-4,4'-diyl)bis(azandiyl))bis(carbonyl))bis(pyrrolidine-1-carboxylate), the target compound, was obtained as a solid (4.3 g, yield: 96%).

The compound (357 mg, 0.5 mmol) obtained above was loaded in the mixed solvent of $CF_3CO_2H$ (2 mL) and $CH_2Cl_2$ (2 mL), followed by stirring at room temperature for 5 hours. The volatile components were eliminated under reduced pressure and $CH_2Cl_2$ (2 mL) solution containing i-$Pr_2NEt$ (434 μl, 2.5 mmol) dissolved in there was loaded thereto for 4 minutes. EDC (249 mg, 1.3 mmol) and the compound (251 mg, 1.2 mmol) prepared in Preparative Example 9 were additionally added to the reaction mixture, followed by stirring at room temperature for 75 minutes. The residue was fractionated with $CH_2Cl_2$ and $H_2O$. The organic layer was washed with $H_2O$ and brine, dried over $MgSO_4$, filtered, and concentrated under reduced pressure. The residue proceeded to silica gel mesh, followed by flash chromatography (eluent: EtOAc/hexane mixture) to give the target compound as a white solid (145 mg, yield: 32%).

$^1H$ NMR (DMSO-$d_6$, δ=2.5 ppm, 400 MHz): 10.29 (s, 2H), 8.21 (d, 2H), 7.83 (m, 2H), 7.75 (d, 2H), 7.43-7.05 (m, 12H), 5.51 (d, 2H), 4.41 (m, 2H), 3.85 (app br s, 2H), 3.54 (s, 6H), 3.20 (app br d, 2H), 2.06-1.82 (m, 8H);

$^{13}C$ NMR (DMSO-$d_6$, δ=39.52 ppm, 100 MHz): 171.26, 168.75, 156.42, 139.30, 137.16, 132.79, 131.36, 128.89, 128.35, 128.25, 125.07, 122.88, 121.81, 116.37, 61.05, 56.97, 51.87, 47.22, 29.45, 24.51;

$^{19}F$ NMR (DMSO-$d_6$, 377 MHz,): δ−57.28;

LC/MS: Anal. Calcd. For $[M+H]^+$ $C_{44}H_{42}F_6N_6O_8$: 897.3041. found 897.3046.

Example 3

Preparation of dimethyl((1R,1'R)-((2S,2'S)-2,2'-(((2,2'-dimethyl-[1,1'-biphenyl]-4,4'-diyl)bis(azandiyl))bis(carbonyl))bis(pyrrolidine-2,1-diyl))bis(2-oxo-1-phenylethane-2,1-diyl))dicarbamate

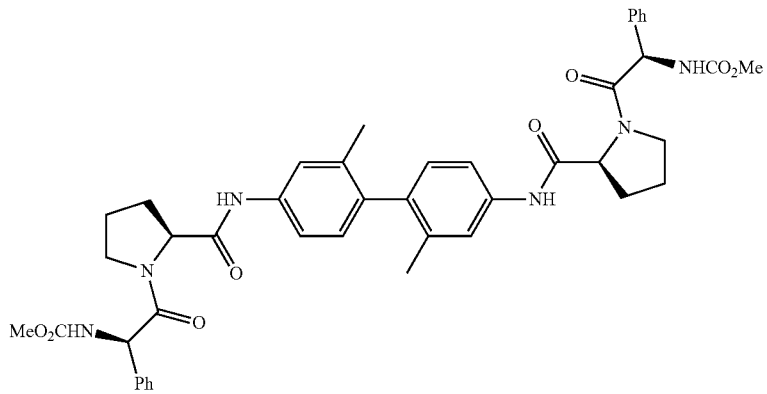

N-Boc-L-proline (2.23 g, 10.4 mmol), EDC (2.35 g, 12.3 mmol), and meta-tolidine (1.0 g, 4.7 mmol) were mixed in $CH_2Cl_2$ (10 mL), followed by stirring at room temperature for 2 hours.

Then, the compound obtained above was fractionated with CH$_2$Cl$_2$ and H$_2$O. The organic layer was washed with 1 N HCl aqueous solution and brine, dried over MgSO$_4$, filtered, and concentrated under reduced pressure. Without any additional purification process, (2S,2'S)-di-tert-butyl 2,2'-(((2,2'-dimethyl-[1,1'-biphenyl]-4,4'-diyl)bis(azandiyl))bis(carbonyl))bis(pyrrolidine-1-carboxylate), the target compound, was obtained as a solid (2.75 g, yield: 96%).

The compound (292 mg, 0.509 mmol) obtained above was loaded in the mixed solvent of CF$_3$CO$_2$H (2 mL) and CH$_2$Cl$_2$ (2 mL), followed by stirring at room temperature for 5 hours. The volatile components were eliminated under reduced pressure and CH$_2$Cl$_2$ (2 mL) solution containing i-Pr$_2$NEt (443 µl, 2.54 mmol) dissolved in there was loaded thereto for 4 minutes. EDC (253 mg, 1.32 mmol) and the compound (256 mg, 1.22 mmol) prepared in Preparative Example 9 were additionally added to the reaction mixture, followed by stirring at room temperature for 75 minutes. The residue was fractionated with CH$_2$Cl$_2$ and H$_2$O. The organic layer was washed with H$_2$O and brine, dried over MgSO$_4$, filtered, and concentrated under reduced pressure. The residue proceeded to silica gel mesh, followed by flash chromatography (eluent: EtOAc/hexane mixture) to give the target compound as a white solid (292 mg, yield: 73%).

$^1$H NMR (DMSO-d$_6$, δ=2.5 ppm, 400 MHz): 9.84 (s, 2H), 7.73 (d, 2H), 7.59 (s, 2H), 7.48-7.14 (m, 12H), 6.87 (d, 2H), 5.51 (d, 2H), 4.42 (m, 2H), 3.84 (m, 2H), 3.55 (s, 6H), 3.20 (m, 2H), 1.98 (s, 6H), 1.97-1.78 (m, 8H);

$^{13}$C NMR (DMSO-d$_6$, δ=39.52 ppm, 100 MHz): 170.2, 168.4, 156.1, 137.9, 137.1, 135.8, 135.8, 129.58, 128.62, 128.1, 127.9, 120.5, 116.7, 60.7, 56.8, 51.7, 47.0, 29.4, 24.3, 19.8;

LC/MS: Anal. Calcd. For [M+H]$^+$ C$_{44}$H$_{48}$N$_6$O$_8$: 789.3606. found 789.3605.

Example 4

Preparation of dimethyl((1R,1'R)-((2S,2'S)-2,2'-(((9H-fluorene-2,7-diyl)bis(azandiyl))bis(carbonyl))bis(pyrrolidine-2,1-diyl))bis(2-oxo-1-phenylethane-2,1-diyl))dicarbamate N-Boc-L-proline (323 mg, 1.5 mmol), EDC (312 mg, 1.63 mmol), and 2,7-diaminofluorene (123 mg, 0.63 mmol) were mixed in CH$_2$Cl$_2$ (2 mL), followed by stirring at room temperature for 2 hours.

Then, the compound obtained above was fractionated with CH$_2$Cl$_2$ and H$_2$O. The organic layer was washed with 1 N HCl aqueous solution and brine, dried over MgSO$_4$, filtered, and concentrated under reduced pressure. Without any additional purification process, (2S,2'S)-di-tert-butyl 2,2'-(((9H-fluorene-2,7-diyl)bis(azandiyl))bis(carbonyl))bis(pyrrolidine-1-carboxylate), the target compound, was obtained as a solid (359 mg, yield: 97%).

The compound (300 mg, 0.51 mmol) obtained above was loaded in the mixed solvent of CF$_3$CO$_2$H (2 mL) and CH$_2$Cl$_2$ (2 mL), followed by stirring at room temperature for 5 hours. The volatile components were eliminated under reduced pressure and CH$_2$Cl$_2$ (2 mL) solution containing i-Pr$_2$NEt (441 µl, 2.5 mmol) dissolved in there was loaded thereto for 4 minutes. EDC (253 mg, 1.3 mmol) and the compound (255 mg, 1.3 mmol) prepared in Preparative Example 9 were additionally added to the reaction mixture, followed by stirring at room temperature for 75 minutes. The residue was fractionated with CH$_2$Cl$_2$ and H$_2$O. The organic layer was washed with H$_2$O and brine, dried over MgSO$_4$, filtered, and concentrated under reduced pressure. The residue proceeded to silica gel mesh, followed by flash chromatography (eluent: EtOAc/hexane mixture) to give the target compound as a white solid (198 mg, yield: 50%).

$^1$H NMR (DMSO-d$_6$, δ=2.5 ppm, 400 MHz): 9.92 (s, 2H), 7.91 (s, 2H), 7.75-7.69 (m, 4H), 7.56 (d, 2H), 7.44-7.13 (m, 10H), 5.52 (d, 2H), 4.43 (m, 2H), 3.88-3.83 (m, 2H), 3.55 (s, 6H), 3.21 (m, 2H), 2.04-1.78 (m, 8H);

$^{13}$C NMR (DMSO-d$_6$, δ=39.52 ppm, 100 MHz): 170.2, 168.5, 156.2, 143.6, 137.5, 137.2, 136.4, 128.7, 128.1, 127.9, 119.6, 118.1, 116.2, 60.8, 56.8, 51.7, 47.0, 36.7, 29.4, 24.3;

LC/MS: Anal. Calcd. For [M+H]$^+$ C$_{43}$H$_{44}$N$_6$O$_8$: 773.3293. found 773.3296.

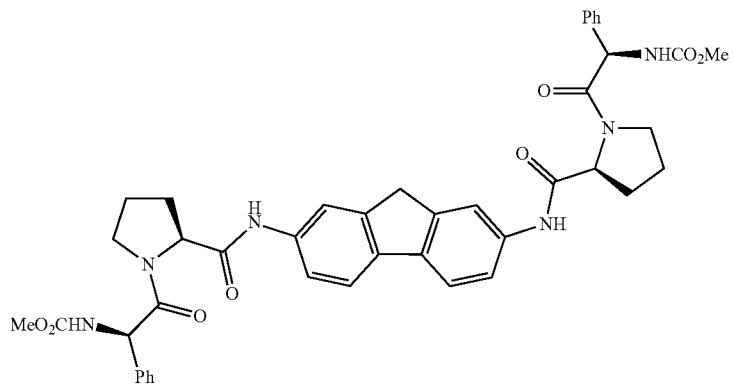

Example 5

Preparation of dimethyl((1R,1'R)-((2S,2'S)-2,2'-(((2,2'-difluoro-[1,1'-biphenyl]-4,4'-diyl)bis(azandiyl))bis(carbonyl))bis(pyrrolidine-2,1-diyl))bis(2-oxo-1-phenylethane-2,1-diyl))dicarbamate

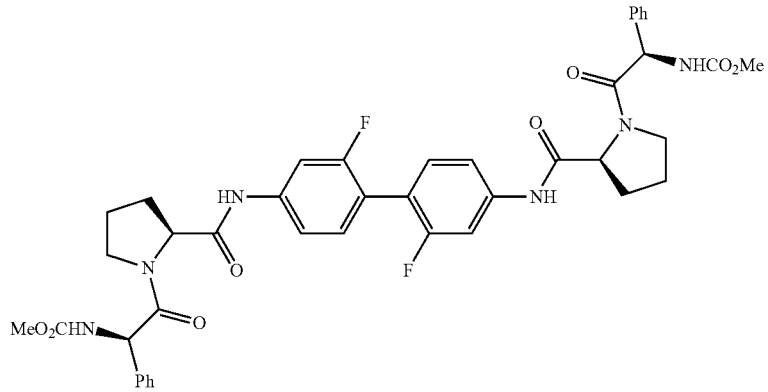

N-Boc-L-proline (2.4 g, 10.9 mmol), EDC (2.3 g, 11.8 mmol), and 4,4'-diamino-2,2'-difluorobiphenyl (1.0 g, 4.5 mmol) were mixed in $CH_2Cl_2$ (15 mL), followed by stirring at room temperature for 2 hours.

Then, the compound obtained above was fractionated with $CH_2Cl_2$ and $H_2O$. The organic layer was washed with 1 N HCl aqueous solution and brine, dried over $MgSO_4$, filtered, and concentrated under reduced pressure. Without any additional purification process, (2S,2'S)-di-tert-butyl 2,2'-(((2,2'-difluoro-[1,1'-biphenyl]-4,4'-diyl)bis(azandiyl))bis(carbonyl))bis(pyrrolidine-1-carboxylate), the target compound, was obtained as a solid (2.6 g, yield: 93%).

The compound (245 mg, 0.42 mmol) obtained above was loaded in the mixed solvent of $CF_3CO_2H$ (2 mL) and $CH_2Cl_2$ (2 mL), followed by stirring at room temperature for 5 hours. The volatile components were eliminated under reduced pressure and $CH_2Cl_2$ (2 mL) solution containing i-$Pr_2$NEt (370 μl, 2.1 mmol) dissolved in there was loaded thereto for 4 minutes. EDC (210 mg, 1.1 mmol) and the compound (212 mg, 1.0 mmol) prepared in Preparative Example 9 were additionally added to the reaction mixture, followed by stirring at room temperature for 75 minutes. The residue was fractionated with $CH_2Cl_2$ and $H_2O$. The organic layer was washed with $H_2O$ and brine, dried over $MgSO_4$, filtered, and concentrated under reduced pressure. The residue proceeded to silica gel mesh, followed by flash chromatography (eluent: EtOAc/hexane mixture) to give the target compound as a white solid (134 mg, yield: 40%).

$^1$H NMR (DMSO-$d_6$, δ=2.5 ppm, 400 MHz): 10.43 (s, 2H), 7.74-7.71 (m, 3H), 7.46-7.11 (m, 15H), 5.51 (d, 2H), 4.43 (m, 2H), 3.83 (m, 2H), 3.54 (s, 6H), 3.19 (m, 2H), 2.05-1.77 (m, 8H);

$^{13}$C NMR (DMSO-$d_6$, δ=39.52 ppm, 100 MHz): 170.8, 168.4, 160.0, 158.0, 156.1, 140.5, 137.2, 131.6, 128.6, 128.5, 128.1, 127.9, 127.6, 117.1, 115.1, 106.3, 106.1, 60.8, 56.7, 51.7, 47.0, 29.3, 24.3;

$^{19}$F NMR (DMSO-$d_6$, 377 MHz,): δ–73.45;

LC/MS: Anal. Calcd. For [M+H]$^+$ $C_{42}H_{42}F_2N_6O_8$: 797.3105. found 797.3112.

Example 6

Preparation of dimethyl((1R,1'R)-((2S,2'S)-2,2'-(((2,2'-dichloro-[1,1'-biphenyl]-4,4'-diyl)bis(azandiyl))bis(carbonyl))bis(pyrrolidine-2,1-diyl))bis(2-oxo-1-phenylethane-2,1-diyl))dicarbamate

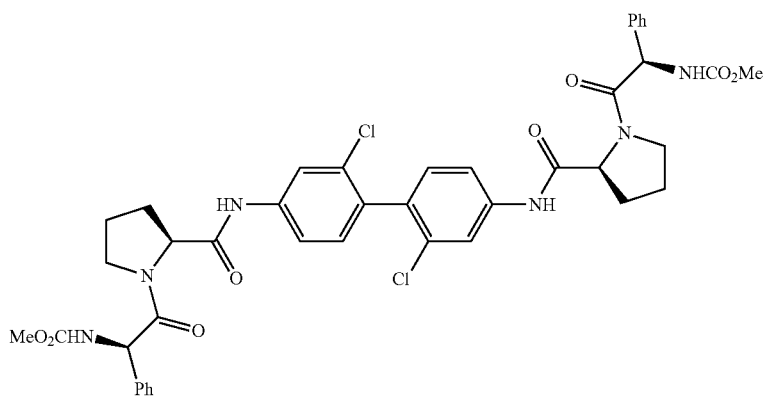

N-Boc-L-proline (2.4 g, 10.9 mmol), EDC (2.3 g, 11.8 mmol), and 4,4'-diamino-2,2'-dichlorobiphenyl (1.15 g, 4.5 mmol) were mixed in $CH_2Cl_2$ (15 mL), followed by stirring at room temperature for 2 hours.

Then, the compound obtained above was fractionated with $CH_2Cl_2$ and $H_2O$. The organic layer was washed with 1 N HCl aqueous solution and brine, dried over $MgSO_4$, filtered, and concentrated under reduced pressure. Without any additional purification process, (2S,2'S)-di-tert-butyl 2,2'-(((2,2'-dichloro-[1,1'-biphenyl]-4,4'-diyl)bis(azandiyl))bis(carbonyl))bis(pyrrolidine-1-carboxylate), the target compound, was obtained as a solid (2.8 g, yield: 95%).

The compound (245 mg, 0.4 mmol) obtained above was loaded in the mixed solvent of $CF_3CO_2H$ (4 mL) and $CH_2Cl_2$ (4 mL), followed by stirring at room temperature for 5 hours. The volatile components were eliminated under reduced pressure and $CH_2Cl_2$ (4 mL) solution containing i-$Pr_2NEt$ (347 µl, 2.0 mmol) dissolved in there was loaded thereto for 4 minutes. EDC (199 mg, 1.04 mmol) and the compound (200 mg, 0.96 mmol) prepared in Preparative Example 9 were additionally added to the reaction mixture, followed by stirring at room temperature for 75 minutes. The residue was fractionated with $CH_2Cl_2$ and $H_2O$. The organic layer was washed with $H_2O$ and brine, dried over $MgSO_4$, filtered, and concentrated under reduced pressure. The residue proceeded to silica gel mesh, followed by flash chromatography (eluent: EtOAc/hexane mixture) to give the target compound as a white solid (146 mg, yield: 44%).

$^1$H NMR (DMSO-$d_6$, δ=2.5 ppm, 400 MHz): 10.14 (s, 2H), 7.97-7.91 (m, 2H), 7.75 (d, 2H), 7.65-7.55 (m, 2H), 7.43-7.12 (m, 12H), 5.51 (d, 2H), 4.39 (m, 2H), 3.84 (m, 2H), 3.55 (s, 6H), 3.20 (m, 2H), 2.06-1.79 (m, 8H);

$^{13}$C NMR (DMSO-$d_6$, δ=39.52 ppm, 100 MHz): 170.8, 168.5, 156.2, 139.9, 137.1, 132.6, 132.1, 131.7, 128.6, 128.1, 127.9, 119.3, 117.7, 60.8, 56.73, 51.68, 47.0, 29.3, 24.3;

LC/MS: Anal. Calcd. For [M+H]$^+$ $C_{42}H_{42}Cl_2N_6O_8$: 829.2514. found 829.2518.

Example 7

Preparation of dimethyl((1R,1'R)-((2S,2'S)-2,2'-(((2,2'-dibromo-[1,1'-biphenyl]-4,4'-diyl)bis(azandiyl))bis(carbonyl))bis(pyrrolidine-2,1-diyl))bis(2-oxo-1-phenylethane-2,1-diyl))dicarbamate N-Boc-L-proline (755 mg, 3.5 mmol), EDC (729 mg, 3.8 mmol), and 4,4'-diamino-2,2'-dibromobiphenyl (500 mg, 1.46 mmol) were mixed in $CH_2Cl_2$ (5 mL), followed by stirring at room temperature for 2 hours.

Then, the compound obtained above was fractionated with $CH_2Cl_2$ and $H_2O$. The organic layer was washed with 1 N HCl aqueous solution and brine, dried over $MgSO_4$, filtered, and concentrated under reduced pressure. Without any additional purification process, (2S,2'S)-di-tert-butyl 2,2'-(((2,2'-dibromo-[1,1'-biphenyl]-4,4'-diyl)bis(azandiyl))bis(carbonyl))bis(pyrrolidine-1-carboxylate), the target compound, was obtained as a solid (991 mg, yield: 92%).

The compound (260 mg, 0.353 mmol) obtained above was loaded in the mixed solvent of $CF_3CO_2H$ (2 mL) and $CH_2Cl_2$ (2 mL), followed by stirring at room temperature for 5 hours. The volatile components were eliminated under reduced pressure and $CH_2Cl_2$ (4 mL) solution containing i-$Pr_2NEt$ (3078 µl, 1.77 mmol) dissolved in there was loaded thereto for 4 minutes. EDC (176 mg, 0.92 mmol) and the compound (177 mg, 0.85 mmol) prepared in Preparative Example 9 were additionally added to the reaction mixture, followed by stirring at room temperature for 75 minutes. The residue was fractionated with $CH_2Cl_2$ and $H_2O$. The organic layer was washed with $H_2O$ and brine, dried over $MgSO_4$, filtered, and concentrated under reduced pressure. The residue proceeded to silica gel mesh, followed by flash chromatography (eluent: EtOAc/hexane mixture) to give the target compound as a white solid (110 mg, yield: 42%).

$^1$H NMR (DMSO-$d_6$, δ=2.5 ppm, 400 MHz): 10.13 (s, 2H), 8.32-8.12 (m, 2H), 7.92-7.61 (m, 4H), 7.41-7.13 (m, 12H), 5.51 (d, 2H), 4.39 (m, 2H), 3.84 (m, 2H), 3.55 (s, 6H), 3.52 (m, 2H), 3.19 (m, 2H), 2.05-1.81 (m, 8H);

$^{13}$C NMR (DMSO-$d_6$, δ=39.52 ppm, 100 MHz): 170.7, 168.5, 156.2, 139.8, 137.1, 135.9, 131.3, 128.6, 128.1, 127.9, 123.0, 122.3, 118.1, 60.8, 56.7, 51.7, 47.0, 29.3, 24.3;

LC/MS: Anal. Calcd. For [M+H]$^+$ $C_{42}H_{42}Br_2N_6O_8$: 917.1504. found 917.1521.

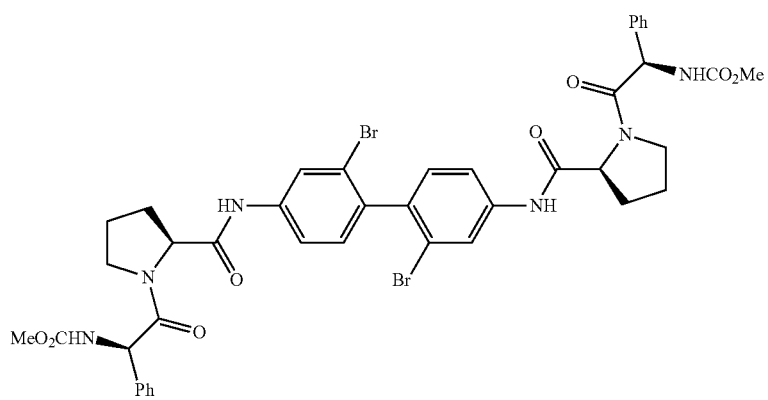

Example 8

Preparation of dimethyl((1R,1'R)-((2R,2'R)-2,2'-(([1,1'-biphenyl]-4,4'-diylbis(azandiyl))bis(carbonyl))bis(pyrrolidine-2,1-diyl))bis(2-oxo-1-phenylethane-2,1-diyl))dicarbamate

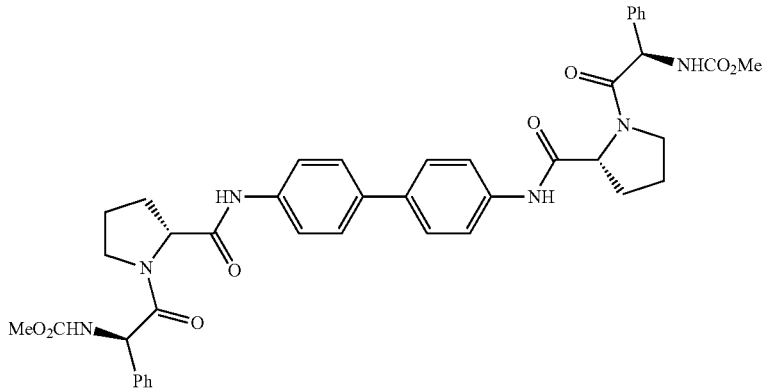

N-Boc-D-proline (771 mg, 3.6 mmol), EDC (812 mg, 4.2 mmol), and benzidine (300 mg, 1.63 mmol) were mixed in CH$_2$Cl$_2$ (4 mL), followed by stirring at room temperature for 2 hours.

Then, the compound obtained above was fractionated with CH$_2$Cl$_2$ and H$_2$O. The organic layer was washed with 1 N HCl aqueous solution and brine, dried over MgSO$_4$, filtered, and concentrated under reduced pressure. Without any additional purification process, (2R,2'R)-di-tert-butyl 2,2'-(([1,1'-biphenyl]-4,4'-diylbis(azandiyl))bis(carbonyl)) bis(pyrrolidine-1-carboxylate), the target compound, was obtained as a solid (930 mg, yield: 99%).

The compound (300 mg, 0.52 mmol) obtained above was loaded in the mixed solvent of CF$_3$CO$_2$H (2 mL) and CH$_2$Cl$_2$ (2 mL), followed by stirring at room temperature for 5 hours. The volatile components were eliminated under reduced pressure and CH$_2$Cl$_2$ (3 mL) solution containing i-Pr$_2$NEt (455 µl, 2.6 mmol) dissolved in there was loaded thereto for 4 minutes. EDC (258 mg, 0.620 mmol) and the compound (260 mg, 1.24 mmol) prepared in Preparative Example 9 were additionally added to the reaction mixture, followed by stirring at room temperature for 75 minutes. The residue was fractionated with CH$_2$Cl$_2$ and H$_2$O. The organic layer was washed with H$_2$O and brine, dried over MgSO$_4$, filtered, and concentrated under reduced pressure. The residue proceeded to silica gel mesh, followed by flash chromatography (eluent: EtOAc/hexane mixture) to give the target compound as a white solid (171 mg, yield: 57%).

$^1$H NMR (DMSO-d$_6$, δ=2.5 ppm, 400 MHz): 10.14 (s, 2H), 7.68-7.60 (m, 9H), 7.46-7.30 (m, 11H), 5.49 (d, 2H), 4.53 (m, 2H), 3.68 (m, 2H), 3.54 (s, 6H), 3.12 (m, 2H), 2.00-2.13 (m, 2H), 1.89-1.82 (m, 6H);

$^{13}$C NMR (DMSO-d$_6$, δ=39.52 ppm, 100 MHz): 170.2, 168.1, 156.4, 138.2, 136.9, 134.4, 128.4, 128.4, 127.8, 126.4, 119.4, 60.6, 56.6, 51.6, 46.9, 29.4, 24.7;

LC/MS: Anal. Calcd. For [M+H]$^+$ C$_{42}$H$_{44}$N$_6$O$_8$: 761.3293. found 761.3281.

Example 9

Preparation of dimethyl((1R,1'R)-((5S,5'S)-5,5'-(([1,1'-biphenyl]-4,4'-diylbis(azandiyl))bis(carbonyl))bis(3-oxopyrrolidine-5,1-diyl))bis(2-oxo-1-phenylethane-2,1-diyl))dicarbamate

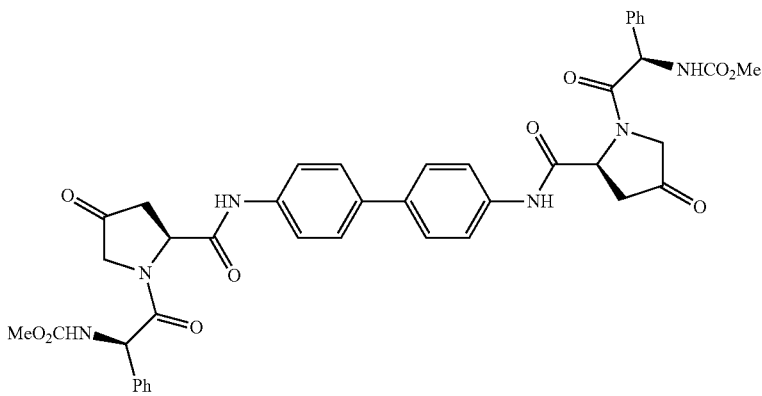

N-Boc-4-oxo-L-proline (335 mg, 1.5 mmol), EDC (303 mg, 1.6 mmol), and benzidine (112 mg, 0.61 mmol) were mixed in CH$_2$Cl$_2$ (2 mL), followed by stirring at room temperature for 2 hours.

Then, the compound obtained above was fractionated with CH$_2$Cl$_2$ and H$_2$O. The organic layer was washed with 1 N HCl aqueous solution and brine, dried over MgSO$_4$, filtered, and concentrated under reduced pressure. Without any additional purification process, (5S,5'S)-di-tert-butyl 5,5'-(([1,1'-biphenyl]-4,4'-diylbis(azandiyl))bis(carbonyl))bis(3-oxopyrrolidine-1-carboxylate), the target compound, was obtained as a solid (320 mg, yield: 87%).

The compound (161 mg, 0.27 mmol) obtained above was loaded in the mixed solvent of CF$_3$CO$_2$H (2 mL) and CH$_2$Cl$_2$ (2 mL), followed by stirring at room temperature for 5 hours. The volatile components were eliminated under reduced pressure and CH$_2$Cl$_2$ (2 mL) solution containing i-Pr$_2$NEt (232 μl, 1.3 mmol) dissolved in there was loaded thereto for 4 minutes. EDC (132 mg, 0.69 mmol) and the compound (133 mg, 0.64 mmol) prepared in Preparative Example 9 were additionally added to the reaction mixture, followed by stirring at room temperature for 75 minutes. The residue was fractionated with CH$_2$Cl$_2$ and H$_2$O. The organic layer was washed with H$_2$O and brine, dried over MgSO$_4$, filtered, and concentrated under reduced pressure. The residue proceeded to silica gel mesh, followed by flash chromatography (eluent: EtOAc/hexane mixture) to give the target compound as a white solid (48 mg, yield: 23%).

$^1$H NMR (DMSO-d$_6$, δ=2.5 ppm, 400 MHz): 10.38 (s, 2H), 7.92 (d, 2H), 7.70-7.10 (m, 18H), 5.46 (d, 2H), 4.94 (d, 2H), 4.25 (d, 2H) 3.89 (d, 2H), 3.54 (s, 6H), 3.06 (m, 2H), 2.54 (m, 2H);

$^{13}$C NMR (DMSO-d$_6$, δ=39.52 ppm, 100 MHz): 208.5, 170.1, 169.4, 156.1, 137.8, 136.8, 134.7, 128.6, 128.2, 128.1, 126.5, 119.7, 57.4, 56.9, 53.1, 51.7, 40.4;

LC/MS: Anal. Calcd. For [M+H]$^+$ C$_{42}$H$_{40}$N$_6$O$_{10}$: 789.2879. found 789.2877.

Example 10

Preparation of dimethyl((1R,1'R)-((2S,2'S)-2,2'-(([1,1'-biphenyl]-4,4'-diylbis(azandiyl))bis(carbonyl))bis(piperidine-2,1-diyl))bis(2-oxo-1-phenylethane-2,1-diyl))dicarbamate N-Boc-L-pipecolic acid (400 mg, 1.75 mmol), EDC (363 mg, 1.9 mmol), and benzidine (134 mg, 0.73 mmol) were mixed in CH$_2$Cl$_2$ (7 mL), followed by stirring at room temperature for 2 hours.

Then, the compound obtained above was fractionated with CH$_2$Cl$_2$ and H$_2$O. The organic layer was washed with 1 N HCl aqueous solution and brine, dried over MgSO$_4$, filtered, and concentrated under reduced pressure. The residue proceeded to silica gel mesh, followed by flash chromatography (eluent: EtOAc/hexane mixture) to give the target compound (2S,2'S)-di-tert-butyl 2,2'-(([1,1'-biphenyl]-4,4'-diylbis(azandiyl))bis(carbonyl))bis(piperidine-1-carboxylate) as a solid (186 mg, yield: 42%).

The compound (73 mg, 0.12 mmol) obtained above was loaded in the mixed solvent of CF$_3$CO$_2$H (1 mL) and CH$_2$Cl$_2$ (1 mL), followed by stirring at room temperature for 5 hours. The volatile components were eliminated under reduced pressure and DMF (1 mL) solution containing i-Pr$_2$NEt (105 μl, 0.60 mmol) dissolved in there was loaded thereto for 4 minutes. EDC (60 mg, 0.31 mmol) and the compound (60 mg, 0.29 mmol) prepared in Preparative Example 9 were additionally added to the reaction mixture, followed by stirring at room temperature for 75 minutes. The residue was fractionated with CH$_2$Cl$_2$ and H$_2$O. The organic layer was washed with H$_2$O and brine, dried over MgSO$_4$, filtered, and concentrated under reduced pressure. The residue proceeded to silica gel mesh, followed by flash chromatography (eluent: EtOAc/hexane mixture) to give the target compound as a solid (12 mg, yield: 13%).

$^1$H NMR (DMSO-d$_6$, δ=2.5 ppm, 400 MHz): 9.99-9.84 (s, 2H), 7.85-7.30 (m, 20H), 5.73-5.64 (m, 2H), 5.17/4.85 (m, 2H), 4.45/3.77 (m, 2H), 3.55 (app br s, 6H), 3.18/2.83 (m, 2H), 2.15 (m, 2H), 1.76 (m, 2H), 1.63-1.24 (m, 8H);

$^{13}$C NMR (DMSO-d$_6$, δ=39.52 ppm, 100 MHz): 170.0, 169.3, 168.5, 156.2, 138.0, 137.2, 134.5, 128.6, 128.4, 128.2, 127.7, 126.5, 120.2, 119.7, 67.0, 55.5, 52.8, 51.6, 43.2, 27.5, 25.1, 24.6, 19.7;

LC/MS: Anal. Calcd. For [M+H]$^+$ C$_{44}$H$_{48}$N$_6$O$_8$: 789.3606. found 789.3605.

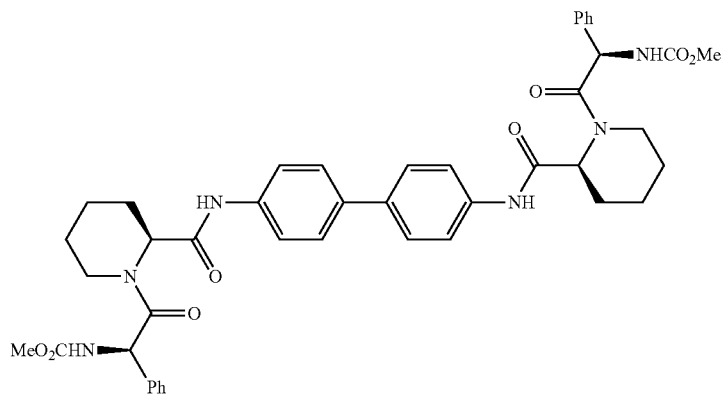

Example 11

Preparation of dimethyl dimethyl ((1R,1'R)-((2R,2'R)-2,2'-(([1,1'-biphenyl]-4,4'-diylbis(azandiyl))bis(carbonyl))bis(piperidine-2,1-diyl))bis(2-oxo-1-phenylethane-2,1-diyl))dicarbamate

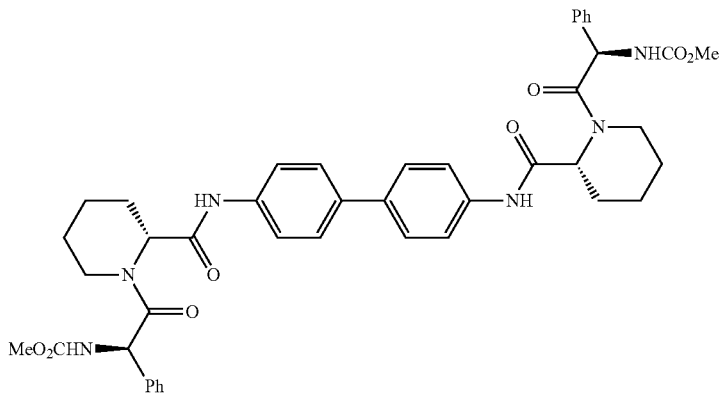

N-Boc-D-pipecolic acid (500 mg, 2.2 mmol), EDC (452 mg, 2.4 mmol), and benzidine (167 mg, 0.91 mmol) were mixed in CH$_2$Cl$_2$ (4 mL), followed by stirring at room temperature for 2 hours.

Then, the compound obtained above was fractionated with CH$_2$Cl$_2$ and H$_2$O. The organic layer was washed with 1 N HCl aqueous solution and brine, dried over MgSO$_4$, filtered, and concentrated under reduced pressure. The residue proceeded to silica gel mesh, followed by flash chromatography (eluent: EtOAc/hexane mixture) to give the target compound (2R,2'R)-di-tert-butyl 2,2'-(([1,1'-biphenyl]-4,4'-diylbis(azandiyl))bis(carbonyl))bis(piperidine-1-carboxylate) as a solid (190 mg, yield: 35%).

The compound (122 mg, 0.2 mmol) obtained above was loaded in the mixed solvent of CF$_3$CO$_2$H (1 mL) and CH$_2$Cl$_2$ (1 mL), followed by stirring at room temperature for 5 hours. The volatile components were eliminated under reduced pressure and DMF (1 mL) solution containing i-Pr$_2$NEt (195 μl, 1.0 mmol) dissolved in there was loaded thereto for 4 minutes. EDC (100 mg, 0.52 mmol) and the compound (101 mg, 0.48 mmol) prepared in Preparative Example 9 were additionally added to the reaction mixture, followed by stirring at room temperature for 75 minutes. The residue was fractionated with CH$_2$Cl$_2$ and H$_2$O. The organic layer was washed with H$_2$O and brine, dried over MgSO$_4$, filtered, and concentrated under reduced pressure. The residue proceeded to silica gel mesh, followed by flash chromatography (eluent: EtOAc/hexane mixture) to give the target compound as a white solid (23 mg, yield: 15%).

$^1$H NMR (DMSO-d$_6$, δ=2.5 ppm, 400 MHz): 9.98-9.84 (s, 2H), 7.84-7.28 (m, 20H), 5.72-5.64 (m, 2H), 5.16/4.85 (m, 2H), 4.45/3.75 (m, 2H), 3.55 (app br s, 6H), 3.17/2.83 (m, 2H), 2.15 (m, 2H), 1.76 (m, 2H), 1.63-1.23 (m, 8H);
$^{13}$C NMR (DMSO-d$_6$, δ=39.52 ppm, 100 MHz): 170.0, 169.3, 168.5, 156.2, 138.0, 137.2, 134.5, 128.6, 128.4, 128.2, 127.7, 126.5, 120.2, 119.7, 67.0, 55.5, 52.8, 51.6, 43.2, 27.5, 25.1, 24.6, 19.7;
LC/MS: Anal. Calcd. For [M+H]$^+$ C$_{44}$H$_{48}$N$_6$O$_8$: 789.3606. found 789.3605.

Example 12

Preparation of dimethyl((1R,1'R)-((2S,2'S)-2,2'-(([1,1'-biphenyl]-4,4'-diylbis(azandiyl))bis(carbonyl))bis(2-methylpyrrolidine-2,1-diyl))bis(2-oxo-1-phenylethane-2,1-diyl))dicarbamate

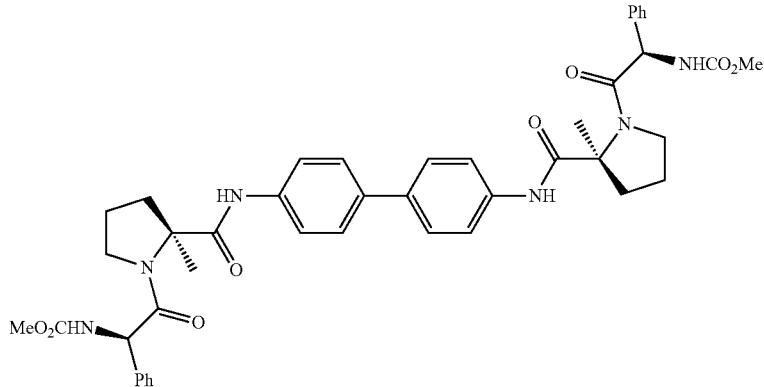

N-Boc-a-methyl-L-proline (200 mg, 0.87 mmol), EDC (181 mg, 0.95 mmol), and benzidine (67 mg, 0.36 mmol) were mixed in CH$_2$Cl$_2$ (2 mL), followed by stirring at room temperature for 2 hours.

Then, the compound obtained above was fractionated with CH$_2$Cl$_2$ and H$_2$O. The organic layer was washed with 1 N HCl aqueous solution and brine, dried over MgSO$_4$, filtered, and concentrated under reduced pressure. The residue proceeded to silica gel mesh, followed by flash chromatography (eluent: EtOAc/hexane mixture) to give the target compound (2S,2'S)-di-tert-butyl 2,2'-(([1,1'-biphenyl]-4,4'-diylbis(azandiyl))bis(carbonyl))bis(2-methylpyrrolidine-1-carboxylate) as a solid (86 mg, yield: 31%).

The compound (144 mg, 0.238 mmol) obtained above was loaded in the mixed solvent of CF$_3$CO$_2$H (1 mL) and CH$_2$Cl$_2$ (1 mL), followed by stirring at room temperature for 5 hours. The volatile components were eliminated under reduced pressure and CH$_2$Cl$_2$ (1 mL) solution containing i-Pr$_2$NEt (208 μl, 1.192 mmol) dissolved in there was loaded thereto for 4 minutes. EDC (119 mg, 0.620 mmol) and the compound (100 mg, 0.572 mmol) prepared in Preparative Example 9 were additionally added to the reaction mixture, followed by stirring at room temperature for 75 minutes. The residue was fractionated with CH$_2$Cl$_2$ and H$_2$O. The organic layer was washed with H$_2$O and brine, dried over MgSO$_4$, filtered, and concentrated under reduced pressure. The residue proceeded to silica gel mesh, followed by flash chromatography (eluent: EtOAc/hexane mixture) to give the target compound as a white solid (77 mg, yield: 41%).

$^1$H NMR (DMSO-d$_6$, δ=2.5 ppm, 400 MHz): 9.03 (s, 1H), 8.89 (s, 1H), 7.77-7.57 (m, 10H), 7.40-7.32 (m, 10H), 5.46 (m, 2H), 3.99 (m, 1H), 3.76 (m, 1H), 3.56 (s, 3H), 3.54 (s, 3H), 3.48 (m, 1H), 3.21 (m, 1H), 2.18-2.08 (m, 2H), 1.91-1.80 (m, 6H), 1.55 (s, 3H), 1.43 (s, 3H);

$^{13}$C NMR (DMSO-d$_6$, δ=39.52 ppm, 100 MHz): 171.8, 171.7, 168.2, 167.7, 156.4, 156.2, 138.2, 138.0, 137.2, 136.5, 134.7, 134.3, 128.7, 128.4, 128.22, 128.17, 127.70, 127.68, 126.09, 126.05, 120.9, 120.3, 67.6, 67.5, 57.2, 57.0, 51.7, 51.6, 47.7, 47.5, 23.5, 23.1, 20.6, 20.5;

LC/MS: Anal. Calcd. For [M+H]$^+$ C$_{44}$H$_{48}$N$_6$O$_8$: 789.3606. found 789.3600.

Example 13

Preparation of dimethyl(2R,2'R)-1,1'-((2S,2'S)-2,2'-(biphenyl-4,4'-diylbis(azandiyl))bis(oxomethylene)bis(pyrrolidine-2,1-diyl))bis(3-methyl-1-oxobutane-2,1-diyl)dicarbamate Step 1: Preparation of (2S,2'S)-di-tert-butyl 2,2'-(biphenyl-4,4'-diylbis(azandiyl))bis(oxomethylene)dipyrrolidine-1-carboxylate N-Boc-L-proline (8 g, 86.3 mmol), 1-ethyl-3-(3-dimethylaminopropyl)carbodiimide (EDC, 19 g, 99 mmol), and benzidine (7 g, 38 mmol) were dissolved in methylenechloride (38 ml), followed by stirring at room temperature for 2 hours. Then, layer separation was performed with the reaction product by using methylenechloride and water. The separated organic layer was washed with 1 N HCl and brine, and dried over MgSO$_4$. The dried organic layer was filtered and distilled under reduced pressure to give the target compound as a brown solid without any additional purification process (20.7 g, yield: 94%).

[a]$_d$=−93.1° (c=10 mg/mL in MeOH);

$^1$H NMR (300 MHz, DMSO-d$_6$, δ=2.5 ppm): 10.06 (s, 2H), 7.69-7.59 (dd, 8H), 4.24 (m, 2H), 3.39 (m, 4H), 2.21 (m, 2H), 1.85 (m, 6H), 1.41-1.28 (app br s, 18H) 1;

$^{13}$C NMR (300 MHz, DMSO-d$_6$, δ=39.52 ppm): 171.53, 153.17, 138.23, 134.45, 126.39, 119.58, 78.45, 60.39, 46.58, 31.04, 28.13, 27.95, 23.43;

LC/MS: Anal. Calcd. For [M+H]$^+$ C$_{32}$H$_{42}$N$_4$O$_6$: 579.3177. found 579.3152.

Step 2: Preparation of dimethyl(2R,2'R)-1,1'-((2S,2'S)-2,2'-(biphenyl-4,4'-diylbis(azandiyl))bis(oxomethylene)bis(pyrrolidine-2,1-diyl))bis(3-methyl-1-oxobutane-2,1-diyl)dicarbamate The compound (138 mg, 0.238 mmol) prepared in step 1 was dissolved in the mixed solvent comprising methylenechloride (1 ml) and trifluoroacetic acid (1 ml), followed by stirring at room temperature for 5 hours. The reaction mixture was distilled under reduced pressure to eliminate volatile components. 1-ethyl-3-(3-dimethylaminopropyl)carbodiimide (EDC, 119 mg, 0.62 mmol), the compound (100 mg, 0.572 mmol) prepared in Preparative Example 1, diisopropylethylamine (DIPEA, 208 μl, 1.192 mmol), and methylenechloride (1 ml) were added to the reaction vessel containing the above reaction mixture for 4 minutes, followed by stirring at room temperature for 75 minutes. Then, layer separation was performed with the reaction product by using methylenechloride and water. The separated organic layer was washed with water. The organic layer was dried over MgSO$_4$, filtered, and dried under reduced pressure. The

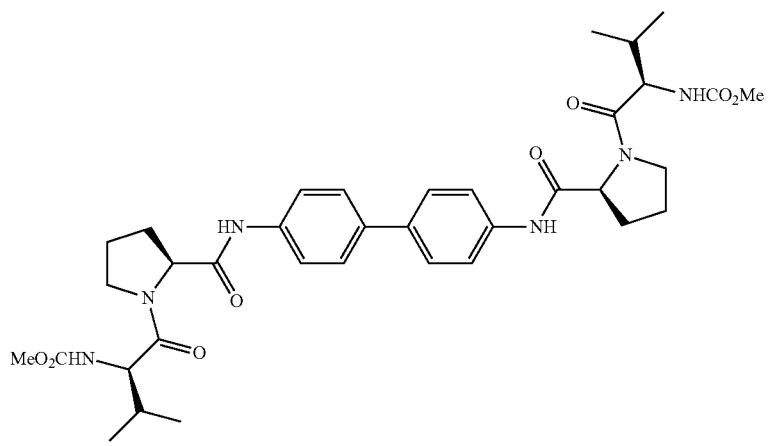

dried reaction product was purified by column chromatography (silica gel, ethylacetate/n-hexane) to give the target compound as a white solid (60 mg, yield: 36%).

[a]$_d$=−167.2° (c=10 mg/mL in MeOH);

$^1$H NMR (400 MHz, DMSO-d$_6$, δ=2.5 ppm): 10.07 (s, 2H), 7.63-7.54 (dd, 8H), 7.31 (d, 2H), 4.43 (m, 2H), 4.01 (t, 2H), 3.80 (m, 2H), 3.61 (m, 2H), 3.5 (s, 6H), 2.13 (m, 2H), 1.89 (m, 8H), 0.92 (d, 6H), 0.86 (d, 6H);

$^{13}$C NMR (400 MHz, DMSO-d$_6$, δ=39.52 ppm): 170.39, 170.37, 156.79, 138.25, 134.32, 126.39, 119.34, 60.21, 57.95, 51.43, 47.23, 29.87, 29.47, 24.67, 18.91, 18.63;

LC/MS: Anal. Calcd. For [M+H]$^+$ C$_{36}$H$_{48}$N$_6$O$_8$: 699.3306. found 693.3572.

Example 14

Preparation of (S,2S,2'S)—N,N'-(biphenyl-4,4'-diyl) bis(1-((S)-2-(dimethylamino)-2-phenylacetyl)pyrrolidine-2-carboxamide)

The target compound was obtained (40 mg, yield: 25%) by the same manner as described in Example 13 except that the compound (100 mg, 0.56 mmol) prepared in Preparative Example 3 was used instead of the compound (138 mg, 0.238 mmol) prepared in Preparative Example 1 in step 2 of Example 13.

[a]$_d$=−201.3° (c=19 mg/mL in MeOH);

$^1$H NMR (400 MHz, DMSO-d$_6$, δ=2.5 ppm): 10.09 (s, 2H), 7.68-7.60 (dd, 8H), 7.46-7.29 (m, 10H), 4.37 (m, 2H), 4.21 (s, 2H), 3.87 (m, 2H), 3.45 (m, 2H), 2.16 (s, 12H), 2.16-1.97 (m, 2H), 1.90-1.80 (m, 2H);

$^{13}$C NMR (400 MHz, DMSO-d$_6$, δ=39.52 ppm): 170.51, 169.14, 138.32, 134.32, 129.07, 129.01, 128.23, 127.86, 126.40, 119.39, 71.44, 60.57, 47.19, 42.93, 29.23, 24.51;

LC/MS: Anal. Calcd. For [M+H]$^+$ C$_{42}$H$_{48}$N$_6$O$_4$: 701.3810. found 701.3774.

Example 15

Preparation of (S,2S,2'S)—N,N-(biphenyl-4,4'-diyl) bis(1-((S)-2-(diethylamino)-2-phenylacetyl)pyrrolidine-2-carboxamide)

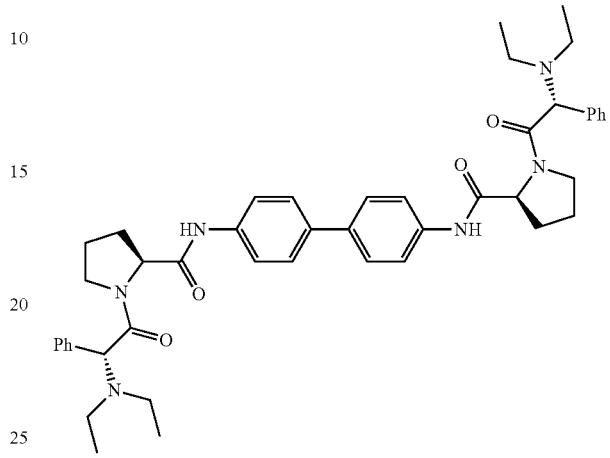

Step 1: Preparation of (2S,2'S)-di-tert-butyl 2,2'-(biphenyl-4,4'-diylbis(azandiyl))bis(oxomethylene) dipyrrolidine-1-carboxylate N-Boc-L-proline (8 g, 86.3 mmol), 1-ethyl-3-(3-dimethylaminopropyl)carbodiimide (EDC, 19 g, 99 mmol), and benzidine (7 g, 38 mmol) were dissolved in methylenechloride (38 ml), followed by stirring at room temperature for 2 hours. Then, layer separation was performed with the reaction product by using methylenechloride and water. The separated organic layer was washed with 1 N HCl and brine, and dried over MgSO$_4$. The dried organic layer was filtered and distilled under reduced pressure to give the target compound as a brown solid without any additional purification process (20.7 g, yield: 94%).

[a]$_d$=−93.1° (c=10 mg/mL in MeOH);

$^1$H NMR (300 MHz, DMSO-d$_6$, δ=2.5 ppm): 10.06 (s, 2H), 7.69-7.59 (dd, 8H), 4.24 (m, 2H), 3.39 (m, 4H), 2.21 (m, 2H), 1.85 (m, 6H), 1.41-1.28 (app br s, 18H) 1;

$^{13}$C NMR (300 MHz, DMSO-d$_6$, δ=39.52 ppm): 171.53, 153.17, 138.23, 134.45, 126.39, 119.58, 78.45, 60.39, 46.58, 31.04, 28.13, 27.95, 23.43;

LC/MS: Anal. Calcd. For [M+H]$^+$ C$_{32}$H$_{42}$N$_4$O$_6$: 578.31044. found 579.3152.

Step 2: Preparation of dimethyl(2R,2'S)-1,1'-((2R,2'R)-2,2'-(biphenyl-4,4'-diylbis(azandiyl))bis(oxomethylene)bis(pyrrolidine-2,1-diyl))bis(3-methyl-1-oxobutane-2,1-diyl)dicarbamate The compound (138 mg, 0.238 mmol) prepared in step 1 was dissolved in the mixed solvent comprising methylenechloride (1 ml) and trifluoroacetic acid (1 ml), followed by stirring at room temperature for 5 hours. The reaction mixture was distilled under reduced pressure to eliminate volatile components. 1-ethyl-3-(3-dimethylaminopropyl) carbodiimide (EDC, 119 mg, 0.62 mmol), the compound (100 mg, 0.485 mmol) prepared in Preparative Example 4, diisopropylethylamine (DIPEA, 208 µl, 1.192 mmol), and methylenechloride (1 ml) were added to the reaction vessel containing the above reaction mixture for 4 minutes, followed by stirring at room temperature for 75 minutes. Then, layer separation was performed with the reaction product by using methylenechloride and water. The separated organic layer was washed with water. The organic layer was dried over $MgSO_4$, filtered, and dried under reduced pressure. The dried reaction product was purified by column chromatography (silica gel, ethylacetate/n-hexane) to give the target compound as a white solid (34 mg, yield: 22%).

$[\alpha]_d$=181.3° (c=23 mg/mL in MeOH);

$^1$H NMR (400 MHz, DMSO-$d_6$, δ=2.5 ppm): 10.08 (s, 2H), 7.68-7.60 (dd, 8H), 7.43-7.26 (m, 10H), 4.70 (s, 2H), 4.43 (m, 2H), 3.81 (m, 2H), 3.39 (q, 2H), 2.67-2.59 (m, 4H), 2.54-2.45 (m, 4H), 2.11-1.97 (m, 4H), 1.89-1.78 (m, 4H), 0.91 (t, 12H);

$^{13}$C NMR (400 MHz, DMSO-$d_6$, δ=39.52 ppm): 170.51, 169.84, 138.29, 137.54, 134.31, 129.09, 128.07, 127.47, 126.38, 119.38, 66.20, 60.45, 47.07, 43.17, 29.22, 24.58, 12.60;

LC/MS: Anal. Calcd. For $[M+H]^+$ $C_{46}H_{56}N_6O_4$: 757.4436. found 757.4392.

Example 16

Preparation of dimethyl(1S,1'S)-2,2'-((2S,2'S)-2,2'-(biphenyl-4,4'-diylbis(azandiyl))bis(oxomethylene)bis(pyrrolidine-2,1-diyl))bis(2-oxo-1-phenylethane-2,1-diyl)dicarbamate

Example 17

Preparation of (R,2S,2'S)—N,N'-(biphenyl-4,4'-diyl)bis(1-((R)-tetrahydrofuran-2-carbonyl)pyrrolidine-2-carboxamide

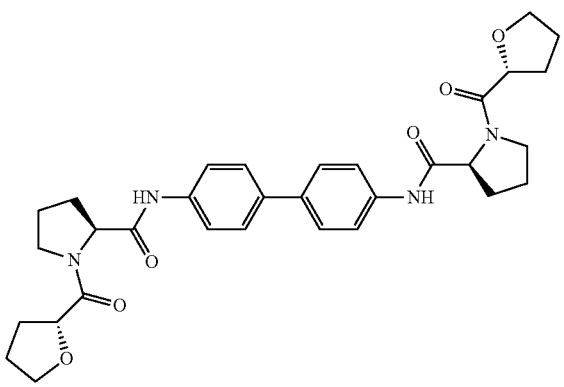

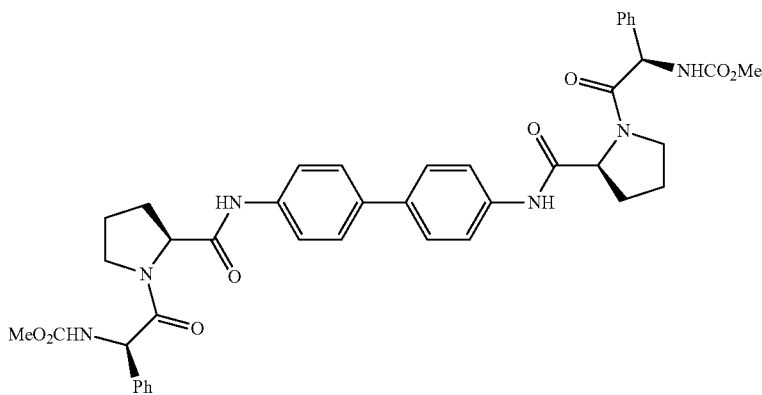

The target compound was obtained (53 mg, yield: 46%) by the same manner as described in Example 13 except that the compound (100 mg, 0.485 mmol) prepared in Preparative Example 5 was used instead of the compound (138 mg, 0.238 mmol) prepared in Preparative Example 1.

$[\alpha]_d$=-226.3° (c=30 mg/mL in MeOH);

$^1$H NMR (400 MHz, DMSO-$d_6$, δ=2.5 ppm): 9.95 (s, 2H), 7.74-7.58 (m, 9H), 7.51-7.30 (m, 10H), 7.14 (app br s, 1H), 5.51 (d, 2H), 4.42 (app br d, 2H), 3.83 (app br s, 2H), 3.55 (s, 6H), 3.20 (app br d, 2H), 2.04-1.79 (m, 8H);

$^{13}$C NMR (400 MHz, DMSO-$d_6$, δ=39.52 ppm): 170.22, 168.35, 156.07, 138.09, 137.17, 134.43, 128.58, 128.03, 127.84, 126.36, 119.57, 60.69, 56.68, 51.63, 46.94, 29.33, 24.25;

LC/MS: Anal. Calcd. For $[M+H]^+$ $C_{42}H_{44}N_6O_8$: 761.3293. found 761.3263.

The target compound was obtained (101 mg, yield: 49%) by the same manner as described in Example 13 except that (R)-(+)-tetrahydrofuran-2-carboxylic acid (83 μl, 0.863 mmol) was used instead of the compound (138 mg, 0.238 mmol) prepared in Preparative Example 1 in step 2 of Example 13.

$[\alpha]_d$=-152.9° (c=26 mg/mL in MeOH);

$^1$H NMR (400 MHz, DMSO-$d_6$, δ=2.5 ppm): 10.21 (s, 2H$^{trans}$ or 2H$^{cis}$), 10.05 (s, 2H$^{trans}$ or 2H$^{cis}$), 7.67-7.59 (dd, 8H), 4.79 (d, 2H$^{trans}$ or 2H$^{cis}$), 4.58 (t, 2H$^{trans}$ or 2H$^{cis}$), 4.42 (d, 2H$^{trans}$ or 2H$^{cis}$), 4.30 (t, 2H$^{trans}$ or 2H$^{cis}$), 3.83-3.68 (m, 5H$^{trans}$/5H$^{cis}$), 3.58-3.37 (m, 3H$^{trans}$/3H$^{cis}$), 2.13-1.75 (m, 16H$^{trans}$/16H$^{cis}$);

$^{13}$C NMR (400 MHz, DMSO-$d_6$, δ=39.52 ppm): 170.78, 170.52, 170.29, 170.13, 138.21, 134.31, 126.50, 126.43, 126.38, 126.31, 119.77, 119.44, 76.22, 76.08, 68.38, 68.18, 60.37, 59.77, 46.99, 46.62, 32.09, 29.16, 28.22, 25.32, 25.05, 24.62, 21.80;

LC/MS: Anal. Calcd. For $[M+H]^+$ $C_{36}H_{38}N_4O_6$: 575.2864. found 575.2839.

Example 18

Preparation of dimethyl(2S,2'S)-1,1'-((2S,2'R)-2,2'-(biphenyl-4,4'-diylbis(azandiyl))bis(oxomethylene)bis(pyrrolidine-2,1-diyl))bis(1-oxopropane-2,1-diyl)dicarbamate

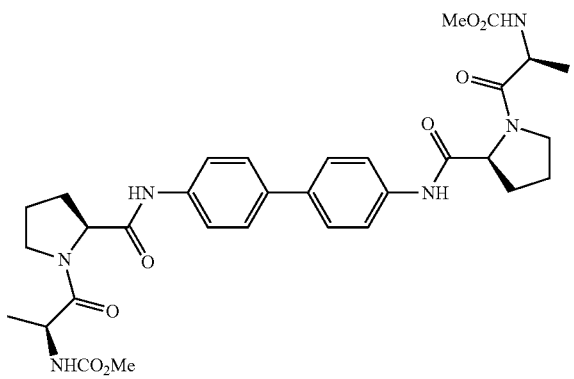

The target compound was obtained (69 mg, yield: 47%) by the same manner as described in Example 13 except that the compound (100 mg, 0.514 mmol) prepared in Preparative Example 6 was used instead of the compound (138 mg, 0.238 mmol) prepared in Preparative Example 1 in step 2 of Example 13.

$[a]_d$=+19.7° (c=23 mg/mL in CHCl$_3$);

$^1$H NMR (400 MHz, DMSO-d$_6$, δ=2.5 ppm): 10.00 (s, 2H), 7.63-7.55 (dd, 8H), 7.32 (d, 2H), 4.43 (m, 2H), 4.30 (t, 2H), 3.65 (m, 2H), 3.58 (m, 2H), 3.49 (s, 6H), 2.14 (m, 2H), 1.96 (m, 6H), 1.18 (d, 6H);

$^{13}$C NMR (400 MHz, DMSO-d$_6$, δ=39.52 ppm): 171.30, 170.80, 156.65, 138.59, 134.73, 126.73, 119.81, 60.62, 51.74, 48.36, 47.11, 29.70, 25.08, 17.19;

LC/MS: Anal. Calcd. For [M+H]$^+$ C$_{32}$H$_{40}$N$_6$O$_8$: 637.2980. found 637.2949.

Example 19

Preparation of dimethyl(2S,2'S)-1,1'-((2S,2'R)-2,2'-(biphenyl-4,4'-diylbis(azandiyl))bis(oxomethylene)bis(pyrrolidine-2,1-diyl))bis(3,3-dimethyl-1-oxobutane-2,1-diyl)dicarbamate

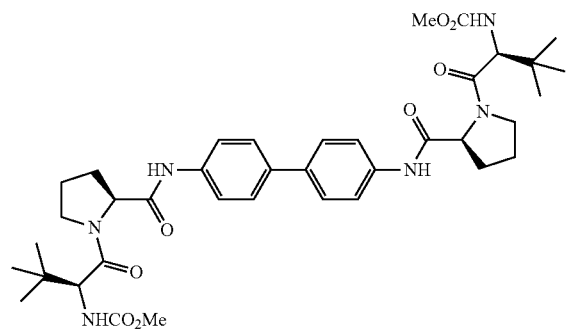

The target compound was obtained (38 mg, yield: 24%) by the same manner as described in Example 13 except that the compound (100 mg, 0.531 mmol) prepared in Preparative Example 7 was used instead of the compound (138 mg, 0.238 mmol) prepared in Preparative Example 1 in step 2 of Example 13.

$[a]_d$=−116.3° (c=33 mg/mL in MeOH);

$^1$H NMR (400 MHz, DMSO-d$_6$, δ=2.5 ppm): 10.11 (s, 2H), 7.66-7.57 (dd, 8H), 7.09 (d, 2H), 4.48 (m, 2H), 4.23 (d, 2H), 3.79 (m, 2H), 3.63 (m, 2H), 3.54 (s, 6H), 2.18 (m, 2H), 2.00 (m, 2H), 1.89 (m, 4H), 0.98 (s, 18H);

$^{13}$C NMR (400 MHz, DMSO-d$_6$, δ=39.52 ppm): 170.38, 169.58, 156.87, 138.27, 134.34, 126.41, 119.34, 60.24, 59.12, 51.48, 47.94, 34.46, 29.50, 26.37, 24.81;

LC/MS: Anal. Calcd. For [M+H]$^+$ C$_{38}$H$_{52}$N$_6$O$_8$: 721.3919. found 721.3882.

Example 20

Preparation of dimethyl(2S,2'S)-1,1'-((2S,2'R)-2,2'-(biphenyl-4,4'-diylbis(azandiyl))bis(oxomethylene)bis(pyrrolidine-2,1-diyl))bis(3-methyl-1-oxobutane-2,1-diyl)dicarbamate

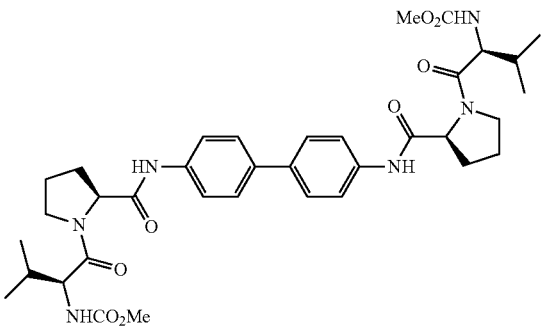

The target compound was obtained (69 mg, yield: 42%) by the same manner as described in Example 13 except that the compound (100 mg, 0.572 mmol) prepared in Preparative Example 2 was used instead of the compound (138 mg, 0.238 mmol) prepared in Preparative Example 1 in step 2 of Example 13.

$[a]_d$=−164.4° (c=47 mg/mL in MeOH);

$^1$H NMR (400 MHz, DMSO-d$_6$, δ=2.5 ppm): 10.11 (s, 2H), 7.67-7.58 (dd, 8H), 7.32 (d, 2H), 4.48 (m, 2H), 4.05 (t, 2H), 3.83 (m, 2H), 3.64 (m, 2H), 3.54 (s, 6H), 2.18 (m, 2H), 1.94 (m, 8H), 0.96 (d, 6H), 0.90 (d, 6H);

$^{13}$C NMR (400 MHz, DMSO-d$_6$, δ=39.52 ppm): 170.39, 170.37, 156.79, 138.26, 134.33, 126.38, 119.36, 60.22, 57.95, 51.42 47.24, 29.88, 29.46, 24.67, 18.92, 18.61;

LC/MS: Anal. Calcd. For [M+H]$^+$ C$_{36}$H$_{48}$N$_6$O$_8$: 693.3606. found 693.3577.

Example 21

Preparation of dimethyl(1S,1S')-2,2'-((4R,4R)-4,4'-(biphenyl-4,4'-diylbis(azandiyl))bis(oxomethylene)bis(thiazolidine-4,3-diyl))bis(2-oxo-1-phenylethane-2,1-diyl)bicarbamate

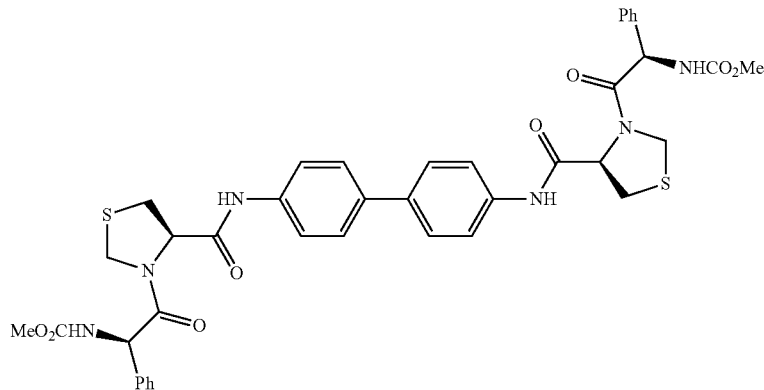

The target compound was obtained (25 mg, yield: 14%) by the same manner as described in Example 13 except that L-thioproline (5 g, 37.5 mmol) was used in step 1 of Example 15 instead of N-Boc-L-proline (8 g, 86.3 mmol).

$^1$H NMR (400 MHz, DMSO-$d_6$, δ=2.5 ppm): 9.89 (s, 2H), 7.93 (d, 2H), 7.73-7.16 (m, 18H), 5.64 (d, 2H), 4.87 (m, 4H), 4.53 (d, 2H), 3.58 (s, 6H), 3.31 (s, 2H), 3.20-3.16 (m, 2H);

$^{13}$C NMR (400 MHz, DMSO-$d_6$, δ=39.52 ppm): 168.32, 167.90, 156.36, 137.76, 136.26, 134.68, 128.66, 128.25, 128.11, 126.42, 119.78, 63.18, 56.81, 51.76, 48.98, 33.08.

Example 22

Preparation of dimethyl((1R,1'R)-((2S,2'S)-2,2'-(((9,9-difluoro-9H-fluorene-2,7-diyl)bis(azandiyl))bis(carbonyl))bis(pyrrolidine-2,1-diyl))bis(2-oxo-1-phenylethane-2,1-diyl))dicarbamate

Step 1: Preparation of (2S,2'S)-di-tert-butyl 2,2'-(((9,9-difluoro-9H-fluorene-2,7-diyl)bis(azandiyl))bis(carbonyl))bis(pyrrolidine-1-carboxylate)

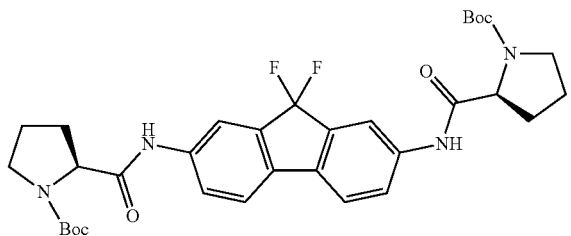 [SMILES: CC(C)(C)OC(=O)N1CCC[C@H]1C(=O)Nc1ccc2c(c1)C(F)(F)c1cc(NC(=O)[C@@H]3CCCN3C(=O)OC(C)(C)C)ccc1-2]

N-Boc-L-proline (24 mg, 0.11 mmol), EDC (24 mg, 0.12 mmol), and 9,9-difluoro-9H-fluorene-2,7-amine (11 mg, 0.047 mmol) obtained in Preparative Example 11 were mixed in CH$_2$Cl$_2$ (1 mL), followed by stirring at ambient temperature for 2 hours. Then, layer separation was performed with the reaction product by using CH$_2$Cl$_2$ and H$_2$O. The organic layer was washed with 1 N aq HCl solution and brine, and dried over MgSO$_4$. The dried organic layer was filtered and concentrated under reduced pressure to give the target compound as a solid without any additional purification process (28 mg, yield: 95%).

$^1$H NMR (DMSO-$d_6$, δ=2.5 ppm, 400 MHz): 10.29 (app br s, 2H), 8.06 (s, 1H), 8.02 (s, 1H), 7.69-7.66 (m, 4H), 4.30-4.25 (m, 1H), 4.21-4.18 (m, 1H), 3.45-3.41 (m, 2H), 3.37-3.34 (m, 2H), 2.23-2.16 (m, 2H), 1.92-1.80 (m, 6H), 1.40 (app br s, 9H), 1.27 (app br s, 9H).

$^{13}$C NMR (DMSO-$d_6$, δ=39.52 ppm, 100 MHz): 174.3, 173.9, 171.9, 171.5, 153.6, 153.1, 139.4, 133.56, 133.49, 122.8, 122.7, 121.2, 114.5, 114.4, 78.8, 78.6, 60.5, 59.3, 58.6, 46.6, 46.2, 46.1, 31.0, 30.3, 28.2, 28.0, 27.9, 27.7, 24.0, 23.4.

$^{19}$F NMR (DMSO-$d_6$, 377 MHz,): δ −108.9, −109.0.

LC/MS: Anal. Calcd. For [M+H]$^+$ C$_{33}$H$_{40}$F$_2$N$_4$O$_6$: 627.2989. found 627.2997.

Step 2: Preparation of dimethyl((1R,1'R)-((2S,2'S)-2,2'-(((9,9-difluoro-9H-fluorene-2,7-diyl)bis(azandiyl))bis(carbonyl))bis(pyrrolidine-2,1-diyl))bis(2-oxo-1-phenylethane-2,1-diyl))dicarbamate

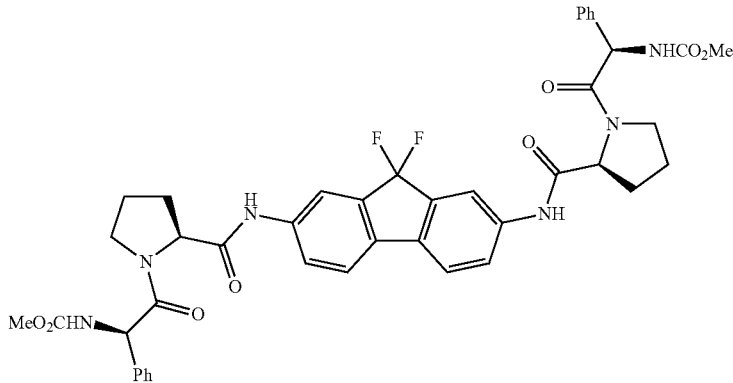

(2S,2'S)-di-tert-butyl 2,2'-(((9,9-difluoro-9H-fluorene-2,7-diyl)bis(azandiyl))bis(carbonyl))bis(pyrrolidine-1-carboxylate) (27 mg, 0.043 mmol) obtained in step 1 was dissolved in the mixed solvent comprising $CF_3CO_2H$ (1 mL) and $CH_2Cl_2$ (1 mL), followed by stirring at room temperature for 5 hours. The volatile components were eliminated under vacuum condition. EDC (21 mg, 0.11 mmol) and Cap (22 mg, 0.10 mmol) were added to $CH_2Cl_2$ (1 mL) solution containing i-$Pr_2NEt$ (28 mL, 0.22 mmol) dissolved therein for 4 minutes/batch, followed by stirring at room temperature for 75 minutes. Then, layer separation was performed with the reaction product by using $CH_2Cl_2$ and $H_2O$. The separated organic layer was washed with $H_2O$ and brine. The organic layer was dried over $MgSO_4$, filtered, and vacuum-concentrated. The residue proceeded to silica gel mesh, followed by flash chromatography (silica gel: EtOAc/hexane as eluent) to give the target compound as a solid (18 mg, yield: 52%).

$^1$H NMR (DMSO-$d_6$, δ 2.5 ppm, 400 MHz): 10.14 (s, 2H), 8.05 (s, 2H), 7.77 (d, 2H), 7.71 (s, 4H), 7.43-7.10 (m, 10H), 5.51 (d, 2H), 4.39 (m, 2H), 3.85 (m, 2H), 3.55 (s, 6H), 3.21 (m, 2H), 2.06-1.79 (m, 8H).

$^{13}$C NMR (DMSO-$d_6$, δ 39.52 ppm, 100 MHz): 170.6, 168.5, 156.2, 139.3, 137.3, 137.0, 128.6, 128.4, 128.1, 127.9, 127.6, 122.8, 121.2, 114.5, 60.8, 56.7, 51.6, 47.0, 29.3, 24.3.

LC/MS: Anal. Calcd. For $[M+H]^+$ $C_{43}H_{42}F_2N_6O_8$: 809.3105. found 809.3109.

Example 23

Preparation of dimethyl((1R,1'R)-((2S,2'S)-2,2'-(((9,9-dimethyl-9H-fluorene-2,7-diyl)bis(azandiyl))bis(carbonyl))bis(pyrrolidine-2,1-diyl))bis(2-oxo-1-phenylethane-2,1-diyl))dicarbamate Step 1: Preparation of (2S,2'S)-di-tert-butyl 2,2'-(((9,9-dimethyl-9H-fluorene-2,7-diyl)bis(azandiyl))bis(carbonyl))bis(pyrrolidine-1-carboxylate)

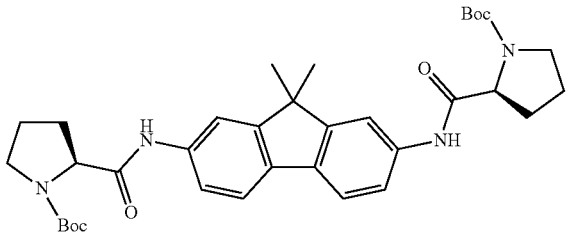 [SMILES: CC(C)(C)OC(=O)N1CCC[C@H]1C(=O)Nc1ccc2c(c1)C(C)(C)c1cc(NC(=O)[C@@H]3CCCN3C(=O)OC(C)(C)C)ccc1-2]

N-Boc-L-proline (173 mg, 0.80 mmol), EDC (167 mg, 0.87 mmol), and 9,9-dimethyl-9H-fluorene-2,7-diamine (75 mg, 0.33 mmol) were mixed in $CH_2Cl_2$ (1 mL), followed by stirring at ambient temperature for 2 hours. Then, layer separation was performed with the reaction product by using $CH_2Cl_2$ and $H_2O$. The organic layer was washed with 1 N aq HCl and brine, and dried over $MgSO_4$. The dried organic layer was filtered and concentrated under reduced pressure to give the target compound as a solid without any additional purification process (201 mg, yield: 97%).

$^1$H NMR (DMSO-$d_6$, δ 2.5 ppm, 400 MHz): 10.10 (app br s, 2H), 7.84 (s, 1H), 7.79 (s, 1H), 7.66 (d, 2H), 7.51 (t, 2H), 4.31-4.28 (m, 1H), 4.24-4.21 (m, 1H), 3.44-3.40 (m, 2H), 3.37-3.31 (m, 2H), 2.21-2.16 (m, 2H), 1.95-1.80 (m, 6H), 1.40 (app br s, 9H), 1.34 (s, 6H), 1.28 (app br s, 9H).

$^{13}$C NMR (DMSO-$d_6$, δ 39.52 ppm, 100 MHz): 174.3, 173.9, 171.4, 171.0, 153.6, 153.2, 138.1, 138.0, 133.7, 133.6, 119.7, 118.4, 118.2, 113.8, 113.6, 78.6, 78.5, 60.4, 60.0, 46.6, 46.1, 42.2, 42.1, 31.0, 30.3, 28.2, 28.1, 27.9, 27.1, 24.0, 23.4.

LC/MS: Anal. Calcd. For $[M+H]^+$ $C_{35}H_{42}N_4O_6$: 619.3490. found 619.3496.

Step 2: Preparation of dimethyl((1R,1'R)-((2S,2'S)-2,2'-(((9,9-dimethyl-9H-fluorene-2,7-diyl)bis(azandiyl))bis(carbonyl))bis(pyrrolidine-2,1-diyl))bis(2-oxo-1-phenylethane-2,1-diyl))dicarbamate

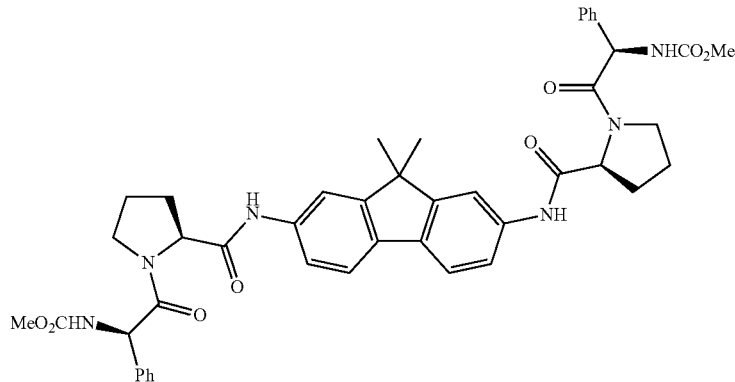

The target compound was obtained as a solid (135 mg, yield: 53%) by the same manner as described in step 2 of Example 22 except that (2S,2'S)-di-tert-butyl 2,2'-(((9,9-dimethyl-9H-fluorene-2,7-diyl)bis(azandiyl))bis(carbonyl))bis(pyrrolidine-1-carboxylate) (200 mg, 0.32 mmol) obtained in step 1 was used instead of (2S,2'S)-di-tert-butyl 2,2'-(((9,9-difluoro-9H-fluorene-2,7-diyl)bis(azandiyl))bis(carbonyl))bis(pyrrolidine-1-carboxylate).

$^1$H NMR (DMSO-$d_6$, δ 2.5 ppm, 400 MHz): 9.96 (s, 2H), 7.86 (s, 2H), 7.74 (d, 2H), 7.69 (d, 2H), 7.51 (dd, 2H), 7.43-7.10 (m, 10H), 5.52 (d, 2H), 4.43 (m, 2H), 3.83 (m, 2H), 3.55 (s, 6H), 3.20 (m, 2H), 2.05-1.78 (m, 8H), 1.41 (s, 6H).

$^{13}$C NMR (DMSO-$d_6$, δ 39.52 ppm, 100 MHz): 170.1, 168.3, 156.1, 153.7, 138.0, 137.2, 133.7, 128.6, 128.1, 127.8, 119.8, 118.3, 113.7, 60.7, 56.7, 51.6, 47.0, 46.5, 29.3, 27.2, 24.3.

LC/MS: Anal. Calcd. For [M+H]$^+$ $C_{45}H_{48}N_6O_8$: 801.3606. found 801.3611.

Example 24

Preparation of dimethyl((1R,1'R)-((2S,2'S)-2,2'-(((9-oxo-9H-fluorene-2,7-diyl)bis(azandiyl))bis(carbonyl))bis(pyrrolidine-2,1-diyl))bis(2-oxo-1-phenylethane-2,1-diyl))dicarbamate Step 1: Preparation of (2S,2'S)-di-tert-butyl 2,2'-(((9-oxo-9H-fluorene-2,7-diyl)bis(azandiyl))bis(carbonyl))bis(pyrrolidine-1-carboxylate)

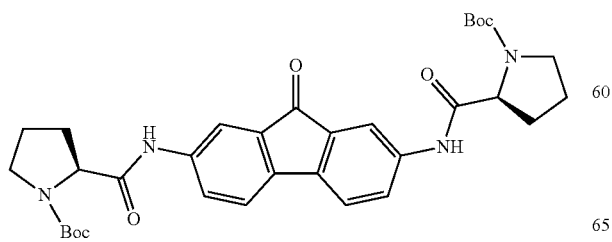

N-Boc-L-proline (123 mg, 0.57 mmol), EDC (119 mg, 0.62 mmol), and 2,7-diamino-9H-fluoren-9-one (50 mg, 0.24 mmol) obtained in Preparative Example 12 were mixed in CH$_2$Cl$_2$ (1 mL), followed by stirring at ambient temperature for 2 hours. Then, layer separation was performed with the reaction product by using CH$_2$Cl$_2$ and H$_2$O. The organic layer was washed with 1 N aq HCl solution and brine, and dried over MgSO$_4$. The dried organic layer was filtered and vacuum-concentrated to give the target compound as a solid without any additional purification process (131 mg, yield: 91%).

$^1$H NMR (DMSO-d$_6$, δ 2.5 ppm, 400 MHz): 10.24 (s, 2H), 7.91 (m, 2H), 7.91 (m, 2H), 7.62 (m, 2H), 4.26-4.16 (m, 2H), 3.46-3.40 (m, 2H), 3.37-3.31 (m, 2H), 2.24-2.16 (m, 2H), 1.94-1.76 (m, 6H), 1.40 (app br s, 9H), 1.27 (app br s, 9H).

$^{13}$C NMR (DMSO-d$_6$, δ 39.52 ppm, 100 MHz): 192.9, 171.9, 171.4, 153.6, 153.1, 139.6, 138.8, 134.2, 125.0, 121.1, 115.0, 78.8, 78.6, 60.5, 60.1, 46.6, 46.1, 31.0, 30.2, 28.2, 28.0, 24.0, 23.4.

LC/MS: Anal. Calcd. For [M+H]$^+$ C$_{33}$H$_{40}$N$_4$O$_7$: 605.2970. found 605.2980.

Step 2: Preparation of dimethyl((1R,1'R)-((2S,2'S)-2,2'-(((9-oxo-9H-fluorene-2,7-diyl)bis(azandiyl))bis(carbonyl))bis(pyrrolidine-2,1-diyl))bis(2-oxo-1-phenylethane-2,1-diyl))dicarbamate

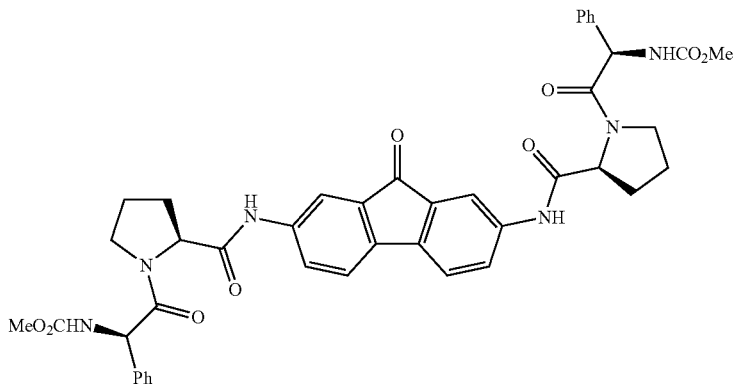

The target compound was obtained as a solid (12 mg, yield: 66%) by the same manner as described in step 2 of Example 22 except that 2,2'-(((9-oxo-9H-fluorene-2,7-diyl)bis(azandiyl))bis(carbonyl))bis(pyrrolidine-1-carboxylate) (14 mg, 0.023 mmol) obtained in step 1 was used instead of (2S,2'S)-di-tert-butyl 2,2'-(((9,9-difluoro-9H-fluorene-2,7-diyl)bis(azandiyl))bis(carbonyl))bis(pyrrolidine-1-carboxylate).

$^1$H NMR (DMSO-d$_6$, δ 2.5 ppm, 400 MHz): 10.10 (s, 2H), 7.91 (s, 2H), 7.76 (t, 4H), 7.64 (d, 2H), 7.43-7.10 (m, 10H), 5.51 (d, 2H), 4.39 (m, 2H), 3.85 (m, 2H), 3.55 (s, 6H), 3.20 (m, 2H), 2.05-1.79 (m, 8H).

$^{13}$C NMR (DMSO-d$_6$, δ 39.52 ppm, 100 MHz): 192.8, 170.6, 168.5, 156.2, 139.5, 138.8, 137.1, 134.2, 128.6, 128.1, 127.9, 125.0, 121.1, 115.0, 60.8, 56.7, 51.7, 47.0, 29.3, 24.3.

LC/MS: Anal. Calcd. For [M+H]$^+$ C$_{43}$H$_{42}$N$_6$O$_9$: 787.3086. found 787.3089.

Structural formulas of the compounds prepared in Examples 1~24 are presented in Table 1.

TABLE 1
| Example | Structural Formula |
|---|---|
| 1 | 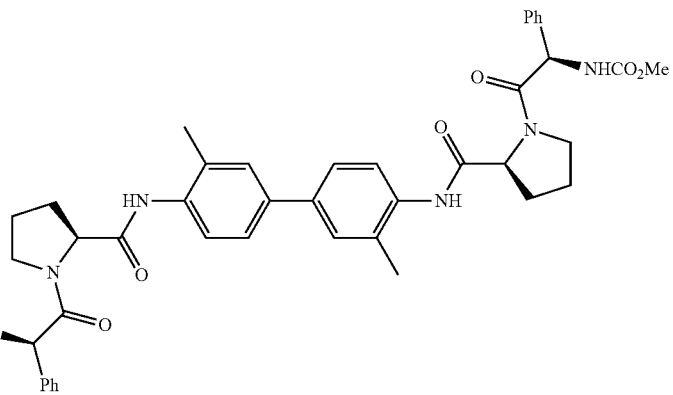 |
| 2 | 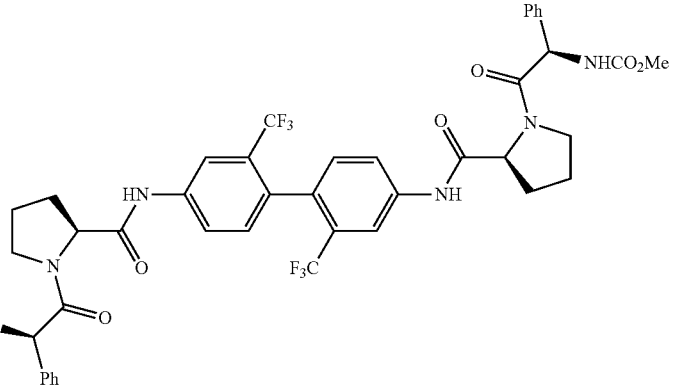 |
| 3 | 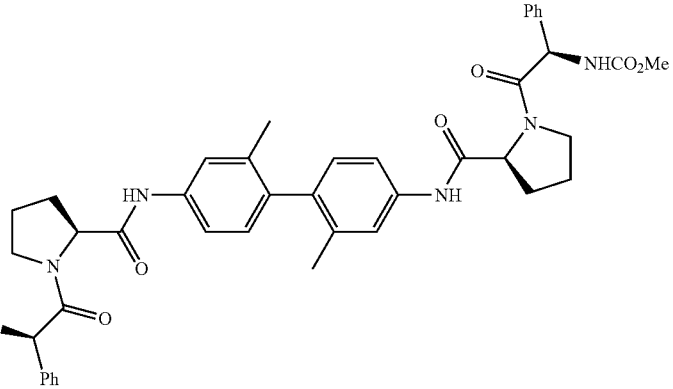 |
| 4 | 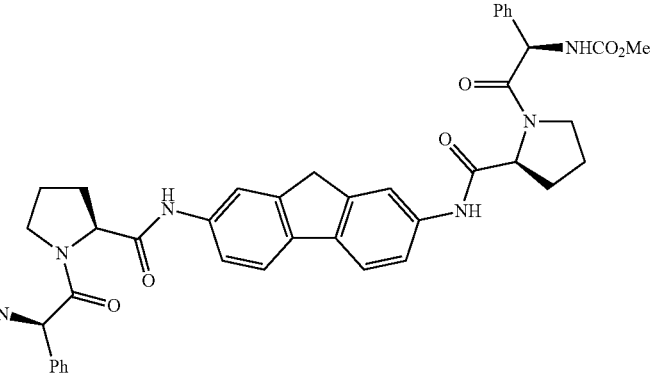 |

TABLE 1-continued

| Example | Structural Formula |
|---|---|
| 5 | (structure: 2,2'-difluoro-biphenyl-4,4'-diyl bis-amide with two (S)-prolyl units, each N-acylated by (S)-2-(methoxycarbonylamino)-2-phenylacetyl groups) |
| 6 | (structure: 2,2'-dichloro-biphenyl-4,4'-diyl bis-amide with two (S)-prolyl units, each N-acylated by (S)-2-(methoxycarbonylamino)-2-phenylacetyl groups) |
| 7 | (structure: 2,2'-dibromo-biphenyl-4,4'-diyl bis-amide with two (S)-prolyl units, each N-acylated by (S)-2-(methoxycarbonylamino)-2-phenylacetyl groups) |
| 8 | (structure: biphenyl-4,4'-diyl bis-amide with two (S)-prolyl units, each N-acylated by (S)-2-(methoxycarbonylamino)-2-phenylacetyl groups) |

TABLE 1-continued

| Example | Structural Formula |
|---|---|
| 9 | |
| 10 | |
| 11 | |
| 12 | |

TABLE 1-continued

| Example | Structural Formula |
|---|---|
| 13 | |
| 14 | |
| 15 | |

TABLE 1-continued
| Example | Structural Formula |
| --- | --- |
| 16 | 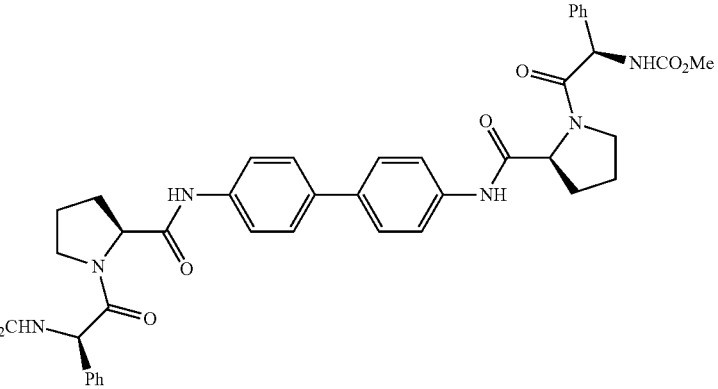 |
| 17 | 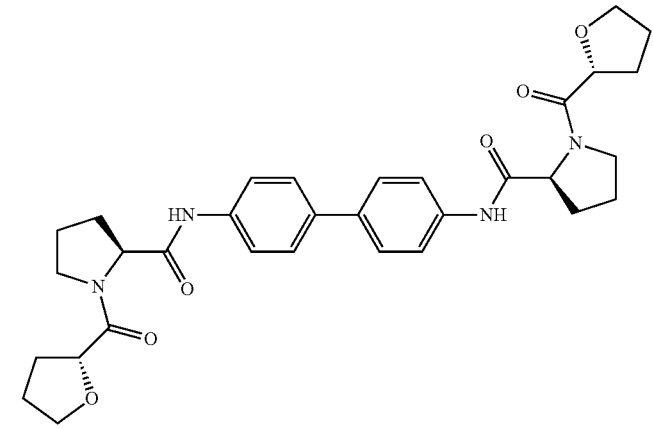 [SMILES: O=C(Nc1ccc(-c2ccc(NC(=O)[C@@H]3CCCN3C(=O)[C@H]3CCCO3)cc2)cc1)[C@@H]1CCCN1C(=O)[C@H]1CCCO1] |
| 18 | 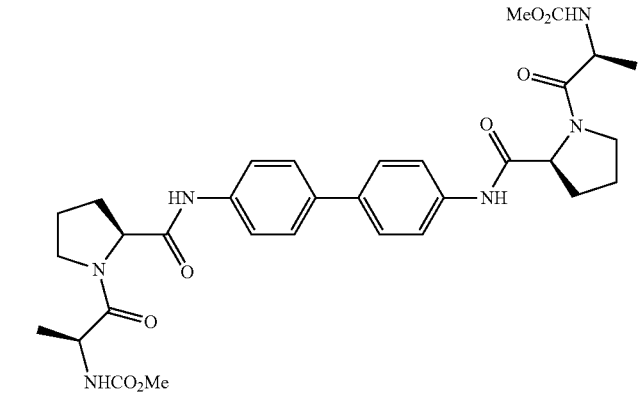 |

TABLE 1-continued

| Example | Structural Formula |
|---|---|
| 19 | |
| 20 | |
| 21 | |
| 22 | |

TABLE 1-continued

| Example | Structural Formula |
|---|---|
| 23 | |
| 24 | |

Experimental Example 1

Evaluation of Anti-HCV Activity 1

To evaluate the anti-HCV activity of the compound represented by formula 1 of the present invention, the following experiment was performed.

The hepatoma cell line huh7.5.1 was distributed in a 12-well cell culture plate at the density of 50,000 cells/well. The cells were cultured in DMEM (Dulbecco's Modified Eagle's Medium 12800-017, GIBCO Co.) supplemented with 10% (v/v) FBS (Fetal Bovine Serum SH30406.02, Hyclone Co.) and 1% (v/v) antibiotics (penicillin/streptomycin solution SV30010, Hyclone Co.) in a 37° C. 6.0% $CO_2$ incubator ($CO_2$ Incubator 311, Forma Scientific Co, Lnc. USA) for 24 hours to lead cell attachment on the plate. Then, the cells were inoculated with HCV (JFH-5aFlucm4, PLoS One. 2011; 6(8):e228808.) having renilla luciferase gene as a reporter for 3 hours. Upon completion of the virus inoculation, the cell culture medium was replaced with the medium containing the compounds prepared in Examples 1~24 at the concentration of 1 µM each. The cells were cultured in a 37° C. 6.0% $CO_2$ incubator ($CO_2$ Incubator 311, Forma Scientific Co, Lnc. USA) for 3 days. Three days after the infection, the cell culture medium was collected to measure the cytotoxicity in the following Experimental Example 3. The cells attached on the plate were washed with PBS (phosphate buffered saline) and then lysed by treating 100 µl of 1× passive lysis buffer (Promega, E1941). The cell lysate (10 µl) was added to renilla luciferase assay reagent (50 µl) in renilla luciferase assay system (Promega, E2820), followed by measurement of luminescence for 10 seconds using the luciferase measure program with Luminometer (GLOMAX 20/20 Luminometer, Promega). At this time, the measurement of luminescence was performed in triplicate with the groups treated with the compounds of Examples 1~24 and the non-treated control group. The mean value was calculated and compared. The luminescence of each compound over the concentration was converted into $EC_{50}$ (half maximal effective concentration) by using sigma plot program, and the results are shown in Table 2.

TABLE 2

| Example | $EC_{50}$ grade |
|---|---|
| 1 | C |
| 2 | A |
| 3 | A |
| 4 | B |
| 5 | A |
| 6 | A |
| 7 | A |
| 8 | C |
| 9 | A |
| 10 | C |
| 11 | C |
| 12 | C |
| 13 | C |
| 14 | B |
| 15 | B |
| 16 | A |
| 17 | C |
| 18 | C |
| 19 | B |
| 20 | C |
| 21 | B |
| 22 | A |

TABLE 2-continued

| Example | EC$_{50}$ grade |
|---------|-----------------|
| 23 | A |
| 24 | B |

In Table 2,
A indicates that EC$_{50}$ is under 1 nM;
B indicates that EC$_{50}$ is 1 nM~100 nM; and
C indicates that EC$_{50}$ is over 100 nM.

As shown in Table 2, the compounds of Examples of the present invention were confirmed to have antiviral activity against HCV residing in hepatoma cells. In particular, EC$_{50}$ of those compounds of Examples 2, 3, 5, 6, 7, 9, 16, 22, and 23 was all under 1 nM, indicating their antiviral activity was excellent.

Therefore, since the compounds of Examples of the present invention have excellent anti-HCV activity, they can be efficiently used as a pharmaceutical composition for the prevention or treatment of liver disease caused by HCV such as acute hepatitis C, chronic hepatitis C, liver cirrhosis, and hepatocellular carcinoma.

Experimental Example 2

Evaluation of Anti-HCV Activity 2

To evaluate the anti-HCV activity, that is the activity to inhibit HCV replication, of the compound represented by formula 1 of the present invention, the following experiment was performed.

The hepatoma cell line huh7.5.1 having NK/R2AN, the replicon with which the replication and translation of HCV could be measured, was distributed in a 12-well cell culture plate at the density of 50,000 cells/well. The cells were cultured in DMEM (Dulbecco's Modified Eagle's Medium 12800-017, GIBCO Co.) supplemented with 10% (v/v) FBS (Fetal Bovine Serum SH30406.02, Hyclone Co.), 1% (v/v) antibiotics (penicillin/streptomycin solution SV30010, Hyclone Co.), and G418 (600 μg/mL, Calbiochem) in a 37° C. 6.0% $CO_2$ incubator ($CO_2$ Incubator 311, Forma Scientific Co, Lnc. USA) for 24 hours to lead cell attachment on the plate. Then, the cells were inoculated with HCV having renilla luciferase gene as a reporter for 3 hours. Upon completion of the virus inoculation, the cell culture medium was replaced with the medium containing the compounds prepared in Examples 1~24 were added to the culture medium at the concentrations of 40 pM~1 μM each. The cells were cultured in a 37° C. 6.0% $CO_2$ incubator ($CO_2$ Incubator 311, Forma Scientific Co, Lnc. USA) for 3 days. Three days after the infection, the cell culture medium was collected to measure the cytotoxicity in the following Experimental Example 3. The cells attached on the plate were washed with PBS (phosphate buffered saline) and then lysed by treating 100 μl of 1× passive lysis buffer (Promega, E1941). The cell lysate (10 μl) was added to renilla luciferase assay reagent (50 μl) in renilla luciferase assay system (Promega, E2820), followed by measurement of luminescence for 10 seconds using the luciferase measure program with Luminometer (GLOMAX 20/20 Luminometer, Promega). At this time, the measurement of luminescence was performed in triplicate with the groups treated with the compounds of Examples 1~24 and the non-treated control group. The mean value was calculated and compared. The luminescence of each compound over the concentration was converted into EC$_{50}$ (half maximal effective concentration) by using sigma plot program, and the results are shown in Table 3. At this time, when EC$_{50}$ was under 100 pM, it was marked as A; when EC$_{50}$ was in the range of 100 pM 1 nM, it was marked as B; when EC$_{50}$ was in the range of 1 nM~100 nM, it was marked as C; and when EC$_{50}$ was over 100 nM, it was marked as D. The results are shown in Table 3.

TABLE 3

| Example | EC$_{50}$ grade |
|---------|-----------------|
| 1 | C |
| 2 | A |
| 3 | A |
| 4 | A |
| 5 | A |
| 6 | A |
| 7 | A |
| 8 | C |
| 9 | A |
| 10 | C |
| 11 | D |
| 12 | C |
| 13 | — |
| 14 | B |
| 15 | B |
| 16 | A |
| 17 | — |
| 18 | — |
| 19 | — |
| 20 | — |
| 21 | A |
| 22 | A |
| 23 | A |
| 24 | A |

In Table 3,
- indicates that experiment was not performed.

As shown in Table 3, the compounds of Examples of the present invention were confirmed to have excellent antiviral activity against HCV. In particular, EC$_{50}$ of those compounds of Examples 2, 3, 4, 5, 6, 7, 9, 16, 21, 22, 23, and 24 was all under 100 pM, indicating that they had excellent anti-HCV activity.

Therefore, since the compounds of Examples of the present invention have excellent anti-HCV activity at a significantly low concentration, they can be efficiently used as a pharmaceutical composition for the prevention or treatment of liver disease caused by HCV such as acute hepatitis C, chronic hepatitis C, liver cirrhosis, and hepatocellular carcinoma.

Experimental Example 3

Evaluation of Cytotoxicity

To evaluate cytotoxicity of the compound represented by formula 1 of the present invention, the following experiment was performed.

According to the manual of cytotoxicity assay kit (Lonza, LT07-117), 20 μl of the culture medium was taken from each well, to which AK detection reagent (ToxiLight Non-destructive Cytotoxicity Bio Assay Kit LT07-117, Lonza Co., 100 μl) was added. The mixture stood for 5 minutes, followed by measurement of the amount of luminescence at 565 nm for 1 second with (VICTOR$^3$™ wallac 1420-051 Multiabel plate Counter (PerkinElmer Inc. Boston, Mass., USA) using Wallac 1420 workstation program. The amount of luminescence was compared among the experimental groups treated with the compounds of Examples 1~21 and the control group non-treated with any of those. As a result, the compound hardly showed cytotoxicity at the concentration of but the fluorescence from the cytotoxicity detection kit was detected at 565 nm when the compound was treated at the concentration of 25 µM, suggesting that the compound showed cytotoxicity at the concentration of 25 µM. Therefore, the compound represented by formula 1 of the present invention was confirmed to be free from cytotoxicity mediated side effects.

Experimental Example 4

Evaluation of Physiological Activity

The following experiment was performed to evaluate physiological activity of the compound prepared in Example 16 by observing the pharmacokinetic changes.

Particularly, the compound of Example 16 was orally or intravenously administered to male mouse, followed by observation of the pharmacokinetic changes. For the oral administration, the compound of Example 16 was dissolved to make the concentration 2.5 mg/ml. The prepared compound solution was orally administered at the dose of 5 mg/kg, followed by drawing blood from the jugular vein of the mouse at regular intervals. For the intravenous administration, tubes were inserted in the jugular vein and the femoral vein of male mouse. The compound solution was intravenously injected through the femoral vein at the dose of 5 mg/kg, followed by drawing blood from the mouse at regular intervals. The drawed blood was centrifuged to separate plasma. The plasma and urine samples were pre-treated with a proper organic solvent, followed by investigation by LC-MS/MS. At this time, LC-MS/MS was performed by using mass spectrometry (Agilent 6460 QQQ, Agilent), LC lamp (Agilent 1260, Agilent), autosampler (Agilent 1260, Agilent), and data analysis system (Peak Sample Data System, Analyst 1.4.2, Applied Biosystems), and the conditions for LC-MS/MS were as follows; sample injection amount: 10 µl, flow rate: 0.3 ml/min, column: 3 µM C18 column (50 mm×2.0 mm, 12 nm, YMC), elution buffer: acetonitrile: 10 mM ammoniumformate buffer=90:10 (v/v), and MS/MS condition: MPM mode: HCV (m/z 761.8170.1), IS (imipramine, m/z 281.286.2). The blood concentration over the administration period of the compound treated via oral or intravenous administration was analyzed, from which the noncompartmental pharmacokinetic parameter was calculated by using WinNonlin (Pharsight, USA). The results are presented in Table 4, FIG. 1, and FIG. 2.

TABLE 4

| Parameter | Intravenous Injection | Oral Administration |
| --- | --- | --- |
| $T_{max}$ (time) | — | 2 ± 1.73 |
| $C_{max}$ (µg/ml) | — | 0.188 ± 0.0518 |
| $T_{1/2}$ (time) | 4.09 ± 3.06 | 15 ± 9.5 |
| $AUC_{0-t}$ (µg · hr/ml) | 9.16 ± 1.03 | 1.83 ± 0.565 |
| $AUC_{0-\infty}$ (µg · hr/ml) | 9.37 ± 1.06 | 2.5 ± 0.498 |
| CL (L/kg/hr) | 0.538 ± 0.0595 | — |
| $V_{ss}$ (L/kg) | 1.31 ± 0.144 | — |
| $F_t$ (%) | 20 | — |

Figure 2:
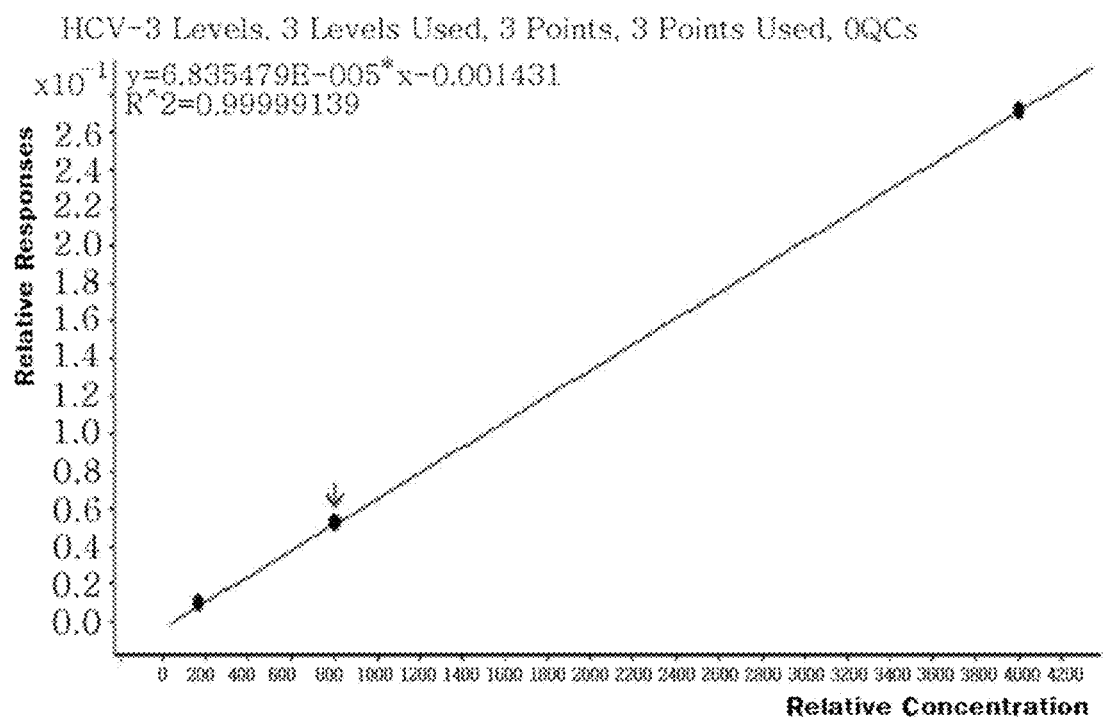
FIG. 2 is a graph illustrating the noncompartmental pharmacokinetic parameter using the concentration of the composition of the invention in blood plasma over the treatment time measured in Experimental Example 4.

As shown in Table 4, FIG. 1, and FIG. 2, the compound of Example 16 of the present invention demonstrated excellent physiological effect in vivo. More precisely, the compound of Example 16 displayed $AUC_{0-24}$, which is the value up to 24 hours from the administration, of 9.16 µg/ml when intravenously injected, and of 1.83 µg/ml when orally administered, and $AUC_{0-\infty}$, which is the value up to infinite time from the administration, of 9.37 µg/ml when intravenously injected, and of 2.5 µg/ml when orally administered. The maximum concentration ($C_{max}$) in plasma was 0.188 µg/ml when orally administered, and the time to reach the maximum concentration of the compound ($T_{max}$) was 2 hours. In addition, bioavailability ($F_t$) of the compound of Example 16 of the present invention was 20%. That is, when the compound of Example 16 of the invention is administered in vivo, it reaches the maximum concentration 2 hours after the administration and the bioavailability thereof reaches 20%, suggesting that the compound has excellent physiological effect.

The compound of Example 16 of the present invention is fast absorbed in vivo and displays high bioavailability with demonstrating excellent physiological activity, so that the compound can be efficiently used as a pharmaceutical composition for the prevention or treatment of liver disease caused by HCV such as acute hepatitis C, chronic hepatitis C, liver cirrhosis, and hepatocellular carcinoma.

Experimental Example 5

Investigation of hERG (Human Ether-a-go-go-Related Gene) Ligand Binding

The following experiment was performed to investigate the side effects caused by the heart toxicity of the compound prepared in Example 16 of the present invention.

One of the major ion channel protein elements playing a role in releasing potassium ions ($K^+$) in cardiomyocytes, hERG is known to be involved in electroactivity of the heart to regulate heart beat. When current that flows through the cell membrane of hERG is inhibited by any drug or inner gene mutation, a lethal symptom can be caused. So, in the development of a drug, the test for hERG inhibition is one of the clinically important tests.

Sudden death is caused by the heart toxicity (TdPa, cardiac ventricular arrhythmia) induced by the increase of electrocardiogram (ECG) QT interval attributed to the inhibition of hERG potassium channel by a drug absorbed in vivo. Thus, the present inventors evaluated the hERG inhibition activity of the compound of Example 16 by measuring fluorescence polarization using a red fluorescent hERG channel ligand detector showing a high affinity to hERG. At this time, the hERG inhibitor astemizole was used as the control and the hERG inhibition activity thereof was also measured by the same manner as the above. The results of the comparison of the hERG inhibition activity between these groups are presented in Table 5.

TABLE 5

| Example | Inhibition Conc. (µM) |
| --- | --- |
| 16 | 9.8 |
| Control | 0.0019 |

As shown in Table 5, the compound of Example 16 of the present invention showed a low hERG inhibitory effect. Particularly, when the compound of Example 16 was treated to hERG, the compound of Example 16 did not bind to the cell membrane of hERG because the red fluorescent hERG channel ligand detector having as high affinity to hERG as to competitively bind to the cell membrane of hERG with displaying a high polarization degree. The hERG inhibiting effective concentration of the compound of Example 16 measured by the polarization degree was 9.8 µM. In the meantime, the hERG inhibiting effective concentration of the control compound, astemizole, was 0.0019 μM. This result indicates that the control compound demonstrated 5160 times as high hERG inhibiting activity as the compound of Example 16. So, since the compound of Example 16 of the present invention has a significantly low hERG inhibitory activity, it can hardly show side effects accompanied by heart toxicity that could cause sudden death.

The benzidine derivatives of the present invention have a significantly low hERG inhibitory effect, so that they are free from worry to cause side effects such as heart toxicity mediated by the inhibition of hERG. Therefore, the benzidine derivatives of the present invention can be efficiently used as a pharmaceutical composition for the prevention or treatment of liver disease caused by HCV such as acute hepatitis C, chronic hepatitis C, liver cirrhosis, and hepatocellular carcinoma.

Experimental Example 6

Evaluation of Plasma Stability

To investigate in vivo cytotoxicity of the compound prepared in Example 16 of the present invention, the following experiment was performed Particularly, the compound of Example 16 was dissolved in dimethylsulfoxide at the concentration of 5 μM, resulting in the preparation of the sample solution. The plasma solution (495 μl) was prepared by mixing phosphate buffer (pH 7.4) and plasma at the ratio of 1:1, which was loaded in each well of a 96-well plate. The sample solution prepared above was added to each well (5 μl) of the plate. Then, the plate was covered with a lid, followed by shaking-culture at 100 rpm at 37° C. for 0.5, 1, and 4 hours in the orbital shaker. The reaction was terminated by adding 0-5° C. acetonitrile. At this time, in the case when the process time was 0 after the sample treatment, the reaction was terminated with acetonitrile at the same time as the sample solution was loaded in the plate containing the plasma solution. Upon completion of the reaction, the plate was kept frozen. Then, the plate was centrifuged at 3000 rpm for 10 minutes. Upon completion of the centrifugation, the supernatant (100 μl) was loaded in each well of a 96-well plate, followed by LC-MS/MS. The result obtained by measuring the plasma survival rate at the process time 0 was considered as the standard, based on which each time-dependent plasma survival rate was calculated by considering the concentration over the time of each sample. The results are presented in Tale 6.

TABLE 6

| Example | Survival rate after 0.5 h (%) | Survival rate after 1 h (%) | Survival rate after 4 h (%) |
| --- | --- | --- | --- |
| 16 | >99 | >99 | >99 |

As shown in Table 6, the compound of Example 16 of the present invention was confirmed not to have in vivo cytotoxicity. Particularly, the plasma survival rate in the mouse treated with the compound of Example 16 was at least 99% even 4 hours after the treatment. Therefore, the compound of Example 16 of the present invention was confirmed not to have in vivo cytotoxicity.

The compound of Example 16 of the present invention is safe in human body since it does not show in vivo cytotoxicity, so that the compound can be efficiently used as a pharmaceutical composition for the prevention or treatment of liver disease caused by HCV such as acute hepatitis C, chronic hepatitis C, liver cirrhosis, and hepatocellular carcinoma.

The compound represented by formula 1 of the present invention can be formulated in various forms according to the purpose of use. The followings are the examples of the formulation of the compositions containing the benzidine derivative of the invention as an active ingredient, but the present invention is not limited thereto.

Manufacturing Example 1

Preparation of Powders

| | |
| --- | --- |
| Compound of formula 1 | 2 g |
| Lactose | 1 g |

Powders were prepared by mixing all the above components, which were filled in airtight packs according to the conventional method for preparing powders.

Manufacturing Example 2

Preparation of Tablets

| | |
| --- | --- |
| Compound of formula 1 | 100 mg |
| Corn starch | 100 mg |
| Lactose | 100 mg |
| Magnesium stearate | 2 mg |

Tablets were prepared by mixing all the above components by the conventional method for preparing tablets.

Manufacturing Example 3

Preparation of Capsules

| | |
| --- | --- |
| Compound of formula 1 | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

Manufacturing Example 4

Preparation of Injectable Solutions

| | |
| --- | --- |
| Compound of formula 1 | 100 mg |
| Mannitol | 100 mg |
| Na$_2$HPO$_4$2H$_2$O | 26 mg |
| Magnesium stearate | 2 mg |
| DW | 2974 ml |

Injectable solutions were prepared by mixing all the above components by the conventional method for preparing injectable solutions.

Manufacturing Example 5

Preparation of Health Functional Food

| Compound of formula 1 | 1000 mg |
|---|---|
| Vitamin complex | proper amount |
| Vitamin A acetate | 70 μg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 μg |
| Vitamin C | 10 mg |
| Biotin | 10 μg |
| Nicotinic acid amide | 1.7 mg |
| Folic acid | 50 μg |
| Calcium pantothenate | 0.5 mg |
| Minerals | proper amount |
| Ferrous sulfate | 1.75 mg |
| Zinc oxide | 0.82 mg |
| Magnesium carbonate | 25.3 mg |
| Potassium phosphate monobasic | 15 mg |
| Potassium phosphate dibasic | 55 mg |
| Potassium citrate | 90 mg |
| Calcium carbonate | 100 mg |
| Magnesium chloride | 24.8 mg |

Vitamins and minerals were mixed according to the preferable composition rate for health food. However, the composition rate can be adjusted. The constituents were mixed according to the conventional method for preparing health food and then the composition for health food was prepared according to the conventional method.

Manufacturing Example 6

Preparation of Health Beverages

| Compound of formula 1 | 1000 mg |
|---|---|
| Citric acid | 1000 mg |
| Oligosaccharide | 100 g |
| Maesil (*Prunus mume*) Extract | 2 g |
| Taurine | 1 g |
| Purified water | up to 900 ml |

The above constituents were mixed according to the conventional method for preparing health beverages. The mixture was heated at 85° C. for 1 hour with stirring and then filtered. The filtrate was loaded in 2 liter sterilized containers, which were sealed and sterilized again, stored in a refrigerator until they would be used for the preparation of a composition for health beverages.

The constituents appropriate for favorite beverages were mixed according to the preferred mixing ratio but the composition ratio can be adjusted according to regional and national preferences, etc.

Manufacturing Example 7

Preparation of Other Health Foods

<7-1> Preparation of Beverage

| Honey | 522 mg |
|---|---|
| Thioctic acid amide | 5 mg |
| Nicotinic acid amide | 10 mg |
| Hydrochloric acid riboflavin natrium | 3 mg |
| Hydrochloric acid pyridoxine | 2 mg |
| Inositol | 30 mg |
| Ortho acid | 50 mg |
| Compound of formula 1 | 0.48~1.28 mg |
| Water | 200 ml |

Beverages were prepared based on the above compositions and contents by following the conventional method.

<7-2> Preparation of Chewing Gum

| Gum base | 20% |
|---|---|
| Sugar | 76.36~76.76% |
| Compound of formula 1 | 0.24~0.64% |
| Fruit flavor | 1% |
| Water | 2% |

Chewing gums were prepared based on the above compositions and contents by following the conventional method.

<7-3> Preparation of Candy

| Sugar | 50~60% |
|---|---|
| Starch syrup | 39.26~49.66% |
| Compound of formula 1 | 0.24~0.64% |
| Orange flavor | 0.1% |

Candies were prepared based on the above compositions and contents by following the conventional method.

<7-4> Preparation of Flour Food 0.5~5.0 weight part of the benzidine derivative represented by formula 1 was added to flour. Health enhancing foods such as bread, cake, cookies, crackers and noodles were prepared with the flour mixture according to the conventional method.

<7-5> Preparation of Dairy Products

5~10 weight part of the benzidine derivative represented by formula 1 was added to 100 weight part of milk. Health enhancing dairy products such as butter and ice cream were prepared with the milk mixture according to the conventional method.

<7-6> Preparation of Sun-Sik

| Brown rice | 30% |
|---|---|
| Yulmu (Job's tears) | 15% |
| Barley | 20% |
| Wild sesame | 7% |
| Black soybean | 7% |
| Black sesame | 7% |
| Compound of formula 1 | 3% |
| Ganoderma lucidum | 0.5% |
| Rehmannia glutinosa | 0.5% |

Brown rice, barley, glutinous rice and Yulmu (Job's tears) were gelatinized according to the conventional method, dried and pulverized to obtain 60-mesh powders. Black soybean, black sesame and wild sesame were steamed and dried according to the conventional method and pulverized to obtain 60-mesh powders. Sun-Sik was prepared by mixing the dry powders of the grains, seeds and the benzidine derivative represented by formula 1 according to the above ratio.

INDUSTRIAL APPLICABILITY

The benzidine derivative of the present invention has excellent antiviral activity against hepatitis C virus, so that the pharmaceutical composition containing the same as an active ingredient can be efficiently used as a pharmaceutical composition for the prevention or treatment of liver disease caused by HCV such as acute hepatitis C, chronic hepatitis C, liver cirrhosis, and hepatocellular carcinoma.

What is claimed is:

1. A compound represented by the following formula 1, an optical isomer thereof, or a pharmaceutically acceptable salt thereof,

[Formula 1]

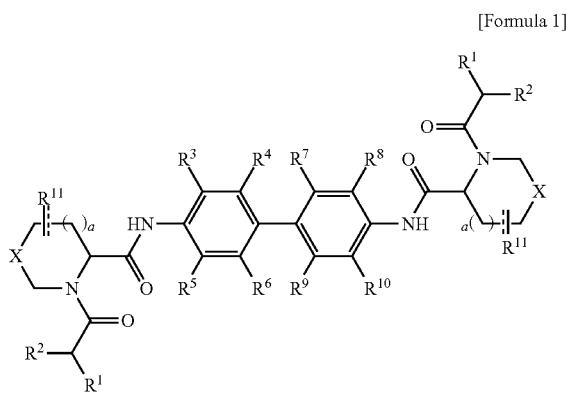

wherein, $R^1$ and $R^2$ are independently —H, —OH, halogen, $C_{1-10}$ straight or branched alkyl, $C_{1-10}$ straight or branched alkoxy, unsubstituted or substituted $C_{6-10}$ aryl, —$NR^{12}R^{13}$, or —NHC(=O)$R^{14}$, wherein the said substituted $C_{6-10}$ aryl is substituted with one or more substituents selected from the group consisting of $C_{1-5}$ straight or branched alkyl, $C_{1-5}$ straight or branched alkoxy, and halogen, or $R^1$ and $R^2$ form a $C_{5-10}$ heterocycloalkyl containing one or more hetero atoms selected from the group consisting of N, O and S along with carbon atoms which are conjugated to the same;
$R^{12}$ and $R^{13}$ are —H, or $C_{1-5}$ straight or branched alkyl;
$R^{14}$ is —H, or $C_{1-5}$ straight or branched alkoxy;
$R^3$, $R^4$, $R^5$, $R^6$, $R^7$, $R^8$, $R^9$, and $R^{10}$ are independently —H, halogen, or unsubstituted or substituted $C_{1-5}$ straight or branched alkyl in which one or more halogens are substituted,
wherein, $R^4$ and $R^7$, or $R^6$ and $R^9$ can form a $C_{5-6}$ ring along with carbon atoms which are conjugated to the same, and the $C_{5-6}$ ring can contain one or more substituents selected from the group consisting of halogen, $C_{1-5}$ straight or branched alkyl, and =O;
X is —O—, —S—, or —CH$_2$—;
$R^{11}$ is —H, —OH, halogen, $C_{1-10}$ straight or branched alkyl, $C_{1-10}$ straight or branched alkyl alkoxy, or =O;
═ is single bond or double bond; and
a is an integer of 0-3.

2. The compound represented by formula 1, the optical isomer thereof, or the pharmaceutically acceptable salt thereof according to claim 1, wherein:
$R^1$ and $R^2$ are independently —H, —OH, halogen, $C_{1-5}$ straight or branched alkyl, $C_{1-5}$ straight or branched alkoxy, unsubstituted or substituted $C_{6-8}$ aryl, —$NR^{12}R^{13}$, or —NHC(=O)$R^{14}$, wherein the said substituted $C_{6-8}$ aryl is substituted with one or more substituents selected from the group consisting of $C_{1-5}$ straight or branched alkyl, $C_{1-5}$ straight or branched alkoxy, and halogen, or $R^1$ and $R^2$ form a $C_{5-8}$ heterocycloalkyl containing one or more hetero atoms selected from the group consisting of N, O and S along with carbon atoms which are conjugated to the same;
$R^{12}$ and $R^{13}$ are —H, or $C_{1-3}$ straight or branched alkyl;
$R^{14}$ is —H, or $C_{1-3}$ straight or branched alkoxy;
$R^3$, $R^4$, $R^5$, $R^6$, $R^7$, $R^8$, $R^9$, and $R^{10}$ are independently —H, halogen, or unsubstituted or substituted $C_{1-5}$ straight or branched alkyl in which one or more halogens are substituted,
wherein, $R^4$ and $R^7$, or $R^6$ and $R^9$ can form a $C_{5-6}$ ring along with carbon atoms which are conjugated to the same, and the $C_{5-6}$ ring can contain one or more substituents selected from the group consisting of halogen, $C_{1-5}$ straight or branched alkyl, and =O;
X is —S—, or —CH$_2$—;
$R^{11}$ is —H, —OH, $C_{1-5}$ straight or branched alkyl, $C_{1-5}$ straight or branched alkyl alkoxy, or =O;
═ is single bond or double bond;
a is an integer of 0-2.

3. The compound represented by formula 1, the optical isomer thereof, or the pharmaceutically acceptable salt thereof according to claim 1, wherein:
$R^1$ and $R^2$ are independently methyl, isopropyl, tert-butyl, phenyl, dimethylamino, diethylamino, or methoxycarbonylamino, or $R^1$ and $R^2$ form tetrahydrofuran along with carbon atoms which are conjugated to the same;
$R^3$, $R^4$, $R^5$, $R^6$, $R^7$, $R^8$, $R^9$, and $R^{10}$ are independently —H, —F, —Cl, —Br, —CF$_3$, or methyl,
wherein, $R^4$ and $R^7$, or $R^6$ and $R^9$ can form $C_5$ ring along with carbon atoms which are conjugated to the same, and the $C_5$ ring can contain one or more substituents selected from the group consisting of —F, =O, and methyl;
X is —S—, or —CH$_2$—;
$R^{11}$ is —H, or =O;
═ is single bond or double bond; and
a is an integer of 0-1.

4. The compound represented by formula 1, the optical isomer thereof, or the pharmaceutically acceptable salt thereof according to claim 1, wherein the compound represented by formula 1 is selected from the group consisting of the below compounds:

(1) dimethyl ((1R,1'R)-((2S,2'S)-2,2'-(((3,3'-dimethyl-[1,1'-biphenyl]-4,4'-diyl)bis(azandiyl))bis(carbonyl))bis(pyrrolidine-2,1-diyl))bis(2-oxo-1-phenylethane-2,1-diyl))dicarbamate;

(2) dimethyl ((1R,1'R)-((2S,2'S)-2,2'-(((2,2'-bis(trifluoromethyl)-[1,1'-biphenyl]-4,4'-diyl)bis(azandiyl))bis(carbonyl))bis(pyrrolidine-2,1-diyl))bis(2-oxo-1-phenylethane-2,1-diyl))dicarbamate;

(3) dimethyl ((1R,1'R)-((2S,2'S)-2,2'-(((2,2'-dimethyl-[1,1'-biphenyl]-4,4'-diyl)bis(azandiyl))bis(carbonyl))bis(pyrrolidine-2,1-diyl))bis(2-oxo-1-phenylethane-2,1-diyl))dicarbamate;

(4) dimethyl ((1R,1'R)-((2S,2'S)-2,2'-(((9H-fluorene-2,7-diyl)bis(azandiyl))bis(carbonyl))bis(pyrrolidine-2,1-diyl))bis(2-oxo-1-phenylethane-2,1-diyl))dicarbamate;

(5) dimethyl ((1R,1'R)-((2S,2'S)-2,2'-(((2,2'-difluoro-[1,1'-biphenyl]-4,4'-diyl)bis(azandiyl))bis(carbonyl))bis(pyrrolidine-2,1-diyl))bis(2-oxo-1-phenylethane-2,1-diyl))dicarbamate;

(6) dimethyl ((1R,1'R)-((2S,2'S)-2,2'-(((2,2'-dichloro-[1,1'-biphenyl]-4,4'-diyl)bis(azandiyl))bis(carbonyl))bis(pyrrolidine-2,1-diyl))bis(2-oxo-1-phenylethane-2,1-diyl))dicarbamate;

(7) dimethyl ((1R,1'R)-((2S,2'S)-2,2'-(((2,2'-dibromo-[1,1'-biphenyl]-4,4'-diyl)bis(azandiyl))bis(carbonyl))bis(pyrrolidine-2,1-diyl))bis(2-oxo-1-phenylethane-2,1-diyl))dicarbamate;

(8) dimethyl ((1R,1'R)-((2R,2'R)-2,2'-(([1,1'-biphenyl]-4,4'-diylbis(azandiyl))bis(carbonyl))bis(pyrrolidine-2,1-diyl))bis(2-oxo-1-phenylethane-2,1-diyl))dicarbamate;

(9) dimethyl ((1R,1'R)-((5S,5'S)-5,5'-(([1,1'-biphenyl]-4,4'-diylbis(azandiyl))bis(carbonyl))bis(3-oxopyrrolidine-5,1-diyl))bis(2-oxo-1-phenylethane-2,1-diyl))dicarbamate;

(10) dimethyl ((1R,1'R)-((2S,2'S)-2,2'-(([1,1'-biphenyl]-4,4'-diylbis(azandiyl))bis(carbonyl))bis(piperidine-2,1-diyl))bis(2-oxo-1-phenylethane-2,1-diyl))dicarbamate;

(11) dimethyl ((1R,1'R)-((2R,2'R)-2,2'-(([1,1'-biphenyl]-4,4'-diylbis(azandiyl))bis(carbonyl))bis(piperidine-2,1-diyl))bis(2-oxo-1-phenylethane-2,1-diyl))dicarbamate;

(12) dimethyl ((1R,1'R)-((2S,2'S)-2,2'-(([1,1'-biphenyl]-4,4'-diylbis(azandiyl))bis(carbonyl))bis(2-methylpyrrolidine-2,1-diyl))bis(2-oxo-1-phenylethane-2,1-diyl))dicarbamate;

(13) dimethyl (2R,2'R)-1,1'-((2S, 2'S)-2,2'-(biphenyl-4,4'-diylbis(azandiyl))bis(oxomethylene)bis(pyrrolidine-2,1-diyl))bis(3-methyl-1-oxobutane-2,1-diyl)dicarbamate;

(14) (S,2S,2'S)—N,N'-(biphenyl-4,4'-diyl)bis(1-((S)-2-(dimethylamino)-2-phenylacetyl)pyrrolidine-2-carboxamide);

(15) (S,2S,2'S)—N,N'-(biphenyl-4,4'-diyl)bis(1-((S)-2-(diethylamino)-2-phenylacetyl)pyrrolidine-2-carboxamide);

(16) dimethyl (1S,1'S)-2,2'-((2S, 2S')-2,2'-(biphenyl-4,4'-diylbis(azandiyl))bis(oxomethylene)bis(pyrrolidine-2,1-diyl))bis(2-oxo-1-phenylethane-2,1-diyl)dicarbamate;

(17) (R,2S,2'S)—N,N'-(biphenyl-4,4'-diyl)bis(1-((R)-tetrahydrofuran-2-carbonyl)pyrrolidine-2-carboxamide;

(18) dimethyl (2S, 2'S)-1,1'-((2S,2R')-2,2'-(biphenyl-4,4'-diylbis(azandiyl))bis(oxomethylene)bis(pyrrolidine-2,1-diyl))bis(1-oxopropane-2,1-diyl)dicarbamate;

(19) dimethyl (2S,2S')-1,1'-((2S,2R')-2,2'-(biphenyl-4,4'-diylbis(azandiyl))bis(oxomethylene)bis(pyrrolidine-2,1-diyl))bis(3,3-dimethyl-1-oxobutane-2,1-diyl)dicarbamate;

(20) dimethyl (2S,2'S)-1,1'-((2S, 2'R)-2,2'-(biphenyl-4,4'-diylbis(azandiyl))bis(oxomethylene)bis(pyrrolidine-2,1-diyl))bis(3-methyl-1-oxobutane-2,1-diyl)dicarbamate;

(21) dimethyl (1S,1S')-2,2'-((4R,4'R)-4,4'-(biphenyl-4,4'-diylbis(azandiyl))bis(oxomethylene)bis(thiazolidine-4,3-diyl))bis(2-oxo-1-phenylethane-2,1-diyl)bicarbamate;

(22) dimethyl ((1R,1'R)-((2S,2'S)-2,2'-(((9,9-difluoro-9H-fluorene-2,7-diyl)bis(azandiyl))bis(carbonyl))bis(pyrrolidine-2,1-diyl))bis(2-oxo-1-phenylethane-2,1-diyl))dicarbamate;

(23) dimethyl ((1R,1'R)-((2S,2'S)-2,2'-(((9,9-dimethyl-9H-fluorene-2,7-diyl)bis(azandiyl))bis(carbonyl))bis(pyrrolidine-2,1-diyl))bis(2-oxo-1-phenylethane-2,1-diyl))dicarbamate; and

(24) dimethyl ((1R,1'R)-((2S,2'S)-2,2'-(((9-oxo-9H-fluorene-2,7-diyl)bis(azandiyl))bis(carbonyl))bis(pyrrolidine-2,1-diyl))bis(2-oxo-1-phenylethane-2,1-diyl))dicarbamate.

5. A method for preparing the compound represented by formula 1 comprising the following steps as presented in the following reaction formula 1:

preparing the compound represented by formula 4 by reacting the compound represented by formula 2 and the compound represented by formula 3 in an organic solvent (step 1);

preparing the compound represented by formula 5 by eliminating the protection group from the compound represented by formula 4 prepared in step 1 (step 2); and preparing the compound represented by formula 1 by reacting the compound represented by formula 5 prepared in step 2 and the compound represented by formula 6 (step 3),

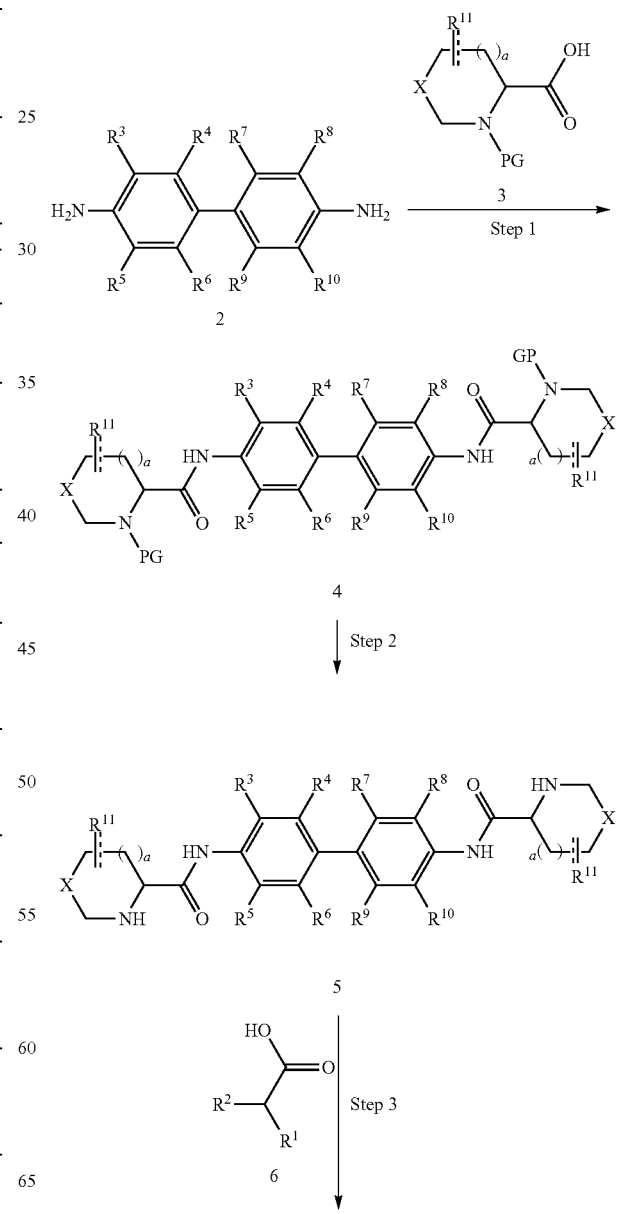

-continued

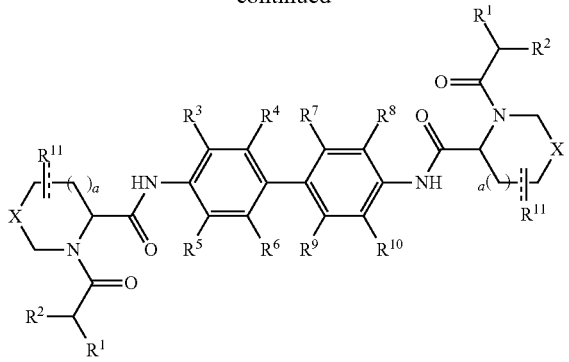

1 wherein $R^1$, $R^2$, $R^3$, $R^4$, $R^5$, $R^6$, $R^7$, $R^8$, $R^9$, $R^{10}$, $R^{11}$, X, a, and ═ are as defined in formula 1; and PG indicates a protecting group.

6. The method for preparing the compound represented by formula 1 according to claim 5, wherein the organic solvent of step 1 is one or more solvents selected from the group consisting of methanol, dimethylformamide, tetrahydrofuran, dichloromethane, and toluene.

7. A pharmaceutical composition comprising the compound represented by formula 1, the optical isomer thereof, or the pharmaceutically acceptable salt thereof, as an active ingredient for preventing or treating liver disease caused by hepatitis C virus.

8. The pharmaceutical composition according to claim 7, wherein the liver disease caused by hepatitis C virus is selected from the group consisting of acute hepatitis C, chronic hepatitis C, liver cirrhosis, and hepatocellular carcinoma.

9. A health food composition comprising the compound represented by formula 1, the optical isomer thereof, or the pharmaceutically acceptable salt thereof of claim 1 as an active ingredient for preventing or improving liver disease caused by hepatitis C virus.

10. The health food composition according to claim 9, wherein the liver disease caused by hepatitis C virus is selected from the group consisting of acute hepatitis C, chronic hepatitis C, liver cirrhosis, and hepatocellular carcinoma.

* * * * *